US010415057B2

(12) United States Patent
Buchholz et al.

(10) Patent No.: US 10,415,057 B2
(45) Date of Patent: Sep. 17, 2019

(54) PSEUDOTYPING OF RETROVIRAL VECTORS, METHODS FOR PRODUCTION AND USE THEREOF FOR TARGETED GENE TRANSFER AND HIGH THROUGHPUT SCREENING

(71) Applicant: BUNDESREPUBLIK DEUTSCHLAND, LETZTVERTRETEN DURCH, Langen (DE)

(72) Inventors: Christian Buchholz, Frankfurt (DE); Sabrina Kneissl, Darmstadt (DE); Klaus Cichutek, Langen (DE); Roberto Cattaneo, Rochester, MN (US)

(73) Assignee: BUNDERSREPUBLIK DEUTSCHLAND, LETZVERTRETEN DURCH DEN PRÄSIDENTEN DES PAUL-EHRLICH-INSTITUTS, Langen (DE)

( * ) Notice: Subject to any disclaimer, the term of this patent is extended or adjusted under 35 U.S.C. 154(b) by 0 days.

(21) Appl. No.: 15/853,004

(22) Filed: Dec. 22, 2017

(65) Prior Publication Data
US 2018/0201954 A1    Jul. 19, 2018

Related U.S. Application Data

(63) Continuation of application No. 12/443,153, filed as application No. PCT/EP2007/008384 on Sep. 26, 2007, now Pat. No. 9,862,971.

(30) Foreign Application Priority Data

Sep. 27, 2006  (EP) .................................. 06020257

(51) Int. Cl.
| C12N 15/63 | (2006.01) |
| C07H 21/04 | (2006.01) |
| A61K 48/00 | (2006.01) |
| C12N 15/86 | (2006.01) |
| C07K 14/005 | (2006.01) |
| A01K 67/00 | (2006.01) |

(52) U.S. Cl.
CPC ............ *C12N 15/86* (2013.01); *C07K 14/005* (2013.01); *C07K 2319/035* (2013.01); *C07K 2319/30* (2013.01); *C12N 2740/16043* (2013.01); *C12N 2740/16045* (2013.01); *C12N 2760/18422* (2013.01); *C12N 2810/6072* (2013.01); *C12N 2810/854* (2013.01); *C12N 2810/859* (2013.01)

(58) Field of Classification Search
CPC .......... C12N 15/86; C12N 2740/16043; C12N 2740/16045; C12N 2760/18422; C12N 2810/6072; C12N 2810/854; C12N 2810/859; C07K 14/005; C07K 2319/035; C07K 2319/30
See application file for complete search history.

(56) References Cited

U.S. PATENT DOCUMENTS

| 6,896,881 | B1 | 5/2005 | Russell et al. |
| 7,510,706 | B2 | 3/2009 | Yonemitsu et al. |
| 9,862,971 | B2* | 1/2018 | Buchholz ............... C12N 15/86 |
| 2005/0048030 | A1 | 3/2005 | Pickles et al. |
| 2008/0227736 | A1 | 9/2008 | Chen et al. |
| 2010/0189690 | A1 | 7/2010 | Buchholz |

OTHER PUBLICATIONS

Yanagi et al. Minireview: Measles virus receptor SLAM (CD150). Virology 299:155-161 (Year: 2002).*
Funke et al. Targeted cell entry of lentiviral vectors. Molecular Therapy 16:1427-1436, (Year: 2008).*
Plumet et al. Dynamics of viral RNA synthesis during measles virus infection. J. Virol. 79:6900-6908, (Year: 2005).*
Calma et al, "Domains in the Simian Immunodeficiency Virus gp41 Cytoplasmic Tail Required for Envelope Incorporation into Particles," Virology, 283: 253-261 (2001).
Cathomen T et al. Measles viruses with altered envelope protein cytoplasmic tails gain cell fusion competence. J. Virol. 72:1224-1234, 1998.
Cattaneo R et al. Altered transcription of a defective measles virus genome derived from a diseased human brain. EMBO J. 6:691-688, 1987.
Gerlier et al., "CD46-mediated Measles virus entry: a first key to host-range specificity," Trends in Microbiology, 3 (9): 338-345 (1995).
Moll et al., "Importance of the Cytoplasmic Tails of the Measles Virus Glycoproteins for Fusogenic Activity and the Generation of Recombinant Measles Viruses," Journal of Virology, 76 (14):7174-7186 (2002).

(Continued)

*Primary Examiner* — Quang Nguyen
(74) *Attorney, Agent, or Firm* — Barnes & Thornburg LLP; Alice O. Martin

(57) ABSTRACT

The invention relates to the pseudotyping of retroviral vectors with heterologous envelope proteins derived from the Paramyxoviridae family, genus *Morbillivirus*, and various uses of the resulting vector particles. The present invention is based on the unexpected and surprising finding that the incorporation of *morbillivirus* F and H proteins having truncated cytoplasmic tails into lentiviral vector particles, and the complex interaction of these two proteins during cellular fusion, allows for a superior and more effective transduction of cells. Moreover, these pseudotyped vector particles allow the targeted gene transfer into a given cell type of interest by modifying a mutated and truncated H protein with a single-chain antibody or ligand directed against a cell surface marker of the target cell.

6 Claims, 30 Drawing Sheets
Specification includes a Sequence Listing.

(56) References Cited

OTHER PUBLICATIONS

Sandrin et al, Intracellular Trafficking of gag and Env Proteins and Their Interactions Modulate Pseudotyping of Retroviruses, J. Virology, 78(13): 7153-7164 (2004).
U.S. Appl. No. 12/443,153, filed Mar. 29, 2010.

* cited by examiner

Fig. 1A

ATGTCACCACAACGAGACCGGATAAATGCCTTCTACAAAGATAACCCCCATCCCAAGGGAAGTAGGATAGTCATTAA
CAGAGAACATCTTATGATTGATAGACCTTATGTTTTGCTGGCTGTTCTGTTTGTCATGTTTCTGAGCTTGATCGGGT
TGCTAGCCATTGCAGGAATTCGACTTCATCGGGCAGCCATCTACACCGCAGAGATCCATAAAAGCCTCAGCACCAAT
CTAGATGTAACTAACTCAATCGAGCATCAGGTCAAGGACGTGCTGACACCACTCTTCAAAATCATCGGTGATGAAGT
GGGCCTGAGGACACCTCAGAGATTCACTGACCTAGTGAAATTCATCTCTGACAAGATTAAATTCCTTAATCCGGATA
GGGAGTACGACTTCAGAGATCTCACTTGGTGTATCAACCCGCCAGAGAGAATCAAATTGGATTATGATCAATACTGT
GCAGATGTGGCTGCTGAAGAGCTCATGAATGCATTGGTGAACTCAACTCTACTGGAGACCAGAACAACCAATCAGTT
CCTAGCTGTCTCAAAGGGAAACTGCTCAGGGCCCACTACAATCAGAGGTCAATTCTCAAACATGTCGCTGTCCCTGT
TAGACTTGTATTTAGGTCGAGGTTACAATGTGTCATCTATAGTCACTATGACATCCCAGGGAATGTATGGGGGAACT
TACCTAGTGGAAAAGCCTAATCTGAGCAGCAAAAGGTCAGAGTTGTCACAACTGAGCATGTACCGAGTGTTTGAAGT
AGGTGTTATCAGAAATCCGGGTTTGGGGGCTCCGGTGTTCCATATGACAAACTATCTTGAGCAACCAGTCAGTAATG
ATCTCAGCAACTGTATGGTGGCTTTGGGGGAGCTCAAACTCGCAGCCCTTTGTCACGGGGAAGATTCTATCACAATT
CCCTATCAGGGATCAGGGAAAGGTGTCAGCTTCCAGCTCGTCAAGCTAGGTGTCTGGAAATCCCCAACCGACATGCA
ATCCTGGGTCCCCTTATCAACGGATGATCCAGTGATAGACAGGCTTTACCTCTCATCTCACAGAGGTGTTATCGCTG
ACAACCAAGCAAAATGGGCTGTCCCGACAACACGAACAGATGACAAGTTGCGAATGGAGACATGCTTCCAACAGGCG
TGTAAGGGTAAAATCCAAGCACTCTGCGAGAATCCCGAGTGGGCACCATTGAAGGATAACAGGATTCCTTCATACGG
GGTCTTGTCTGTTGATCTGAGTCTGACAGTTGAGCTTAAAATCAAAATTGCTTCGGGATTCGGGCCATTGATCACAC
ACGGTTCAGGGATGGACCTATACAAATCCAACCACAACAATGTGTATTGGCTGACTATCCCGCCAATGAAGAACCTA
GCCTTAGGTGTAATCAACACATTGGAGTGGATACCGAGATTCAAGGTTAGTCCCTACCTCTTCACTGTCCCAATTAA
GGAAGCAGGCGGAGACTGCCATGCCCCAACATACCTACCTGCGGAGGTGGATGGTGATGTCAAACTCAGTTCCAATC
TGGTGATTCTACCTGGTCAAGATCTCCAATATGTTTTGGCAACCTACGATACTTCCAGGGTTGAACATGCTGTGGTT
TATTACGTTTACAGCCCAAGCCGCTCATTTTCTTACTTTTATCCTTTTAGGTTGCCTATAAAGGGGGTCCCCATCGA
ATTACAAGTGGAATGCTTCACATGGGACCAAAAACTCTGGTGCCGTCACTTCTGTGTGCTTGCGGACTCAGAATCTG
GTGGACATATCACTCACTCTGGGATGGTGGGCATGGGAGTCAGCTGCACAGTCACCCGGGAAGATGGAACCAATCGC
AGA

Fig. 1B

MSPQRDRINAFYKDNPHPKGSRIVINREHLMIDRPYVLLAVLFVMFLSLIGLLAIAGIRLHRAAIYTAEIHKSLSTN
LDVTNSIEHQVKDVLTPLFKIIGDEVGLRTPQRFTDLVKFISDKIKFLNPDREYDFRDLTWCINPPERIKLDYDQYC
ADVAAEELMNALVNSTLLETRTTNQFLAVSKGNCSGPTTIRGQFSNMSLSLLDLYLGRGYNVSSIVTMTSQGMYGGT
YLVEKPNLSSKRSELSQLSMYRVFEVGVIRNPGLGAPVFHMTNYLEQPVSNDLSNCMVALGELKLAALCHGEDSITI
PYQGSGKGVSFQLVKLGVWKSPTDMQSWVPLSTDDPVIDRLYLSSHRGVIADNQAKWAVPTTRTDDKLRMETCFQQA
CKGKIQALCENPEWAPLKDNRIPSYGVLSVDLSLTVELKIKIASGFGPLITHGSGMDLYKSNHNNVYWLTIPPMKNL
ALGVINTLEWIPRFKVSPYLFTVPIKEAGGDCHAPTYLPAEVDGDVKLSSNLVILPGQDLQYVLATYDTSRVEHAVV
YYVYSPSRSFSYFYPFRLPIKGVPIELQVECFTWDQKLWCRHFCVLADSESGGHITHSGMVGMGVSCTVTREDGTNR
R

Fig. 2A

```
ATGTCCATCATGGGTCTCAAGGTGAACGTCTCTGCCATATTCATGGCAGTACTGTTAACTCTCCAAACACCCACCGG
TCAAATCCATTGGGGCAATCTCTCTAAGATAGGGGTGGTAGGAATAGGAAGTGCAAGCTACAAAGTTATGACTCGTT
CCAGCCATCAATCATTAGTCATAAAATTAATGCCCAATATAACTCTCCTCAATAACTGCACGAGGGTAGAGATTGCA
GAATACAGGAGACTACTGAGAACTGTTTTGGAACCAATTAGAGATGCACTTAATGCAATGACCCAGAATATAAGACC
GGTTCAGAGTGTAGCTTCAAGTAGGAGACACAAGAGATTTGCGGGAGTAGTCCTGGCAGGTGCGGCCCTAGGCGTTG
CCACAGCTGCTCAGATAACAGCCGGCATTGCACTTCACCAGTCCATGCTGAACTCTCAAGCCATCGACAATCTGAGA
GCGAGCCTGGAAACTACTAATCAGGCAATTGAGGCAATCAGACAAGCAGGGCAGGAGATGATATTGGCTGTTCAGGG
TGTCCAAGACTACATCAATAATGAGCTGATACCGTCTATGAACCAACTATCTTGTGATTTAATCGGCCAGAAGCTCG
GGCTCAAATTGCTCAGATACTATACAGAAATCCTGTCATTATTTGGCCCCAGCTTACGGGACCCCATATCTGCGGAG
ATATCTATCCAGGCTTTGAGCTATGCGCTTGGAGGAGACATCAATAAGGTGTTAGAAAAGCTCGGATACAGTGGAGG
TGATTTACTGGGCATCTTAGAGAGCAGAGGAATAAAGGCCCGGATAACTCACGTCGACACAGAGTCCTACTTCATTG
TCCTCAGTATAGCCTATCCGACGCTGTCCGAGATTAAGGGGGTGATTGTCCACCGGCTAGAGGGGGTCTCGTACAAC
ATAGGCTCTCAAGAGTGGTATACCACTGTGCCCAAGTATGTCGCAACCCAAGGGTACCTTATCTCGAATTTTGATGA
GTCATCGTGTACTTTCATGCCAGAGGGAACTGTGTGCAGCCAAAATGCCTTGTACCCGATGAGTCCTCTGCTCCAAG
AATGCCTCCGGGGGTCCACTAAGTCCTGTGCTCGTACACTCGTATCCGGGTCTTTTGGGAACCGGTTCATTTTATCA
CAAGGGAACCTAATAGCCAATTGTGCATCAATCCTTTGCAAGTGTTACACAACAGGAACGATCATTAATCAAGACCC
TGACAAGATCCTAACATACATTGCTGCCGATCACTGCCCGGTAGTCGAGGTGAACGGCGTGACCATCCAAGTCGGGA
GCAGGAGGTATCCAGACGCTGTGTACTTGCACAGAATTGACCTCGGTCCTCCCATATCATTGGAGAGGTTGGACGTA
GGGACAAATCTGGGGAATGCAATTGCTAAGTTGGAGGATGCCAAGGAATTGTTGGAGTCATCGGACCAGATATTGAG
GAGTATGAAAGGTTTATCGAGCACTAGCATAGTCTACATCCTGATTGCAGTGTGTCTTGGAGGGTTGATAGGGATCC
CCGCTTTAATATGTTGCTGCAGGGGGCGTTGTAATAAAAAGGGAGAACAAGTTGGTATGTCAAGACCAGGCCTAAAG
CCTGATCTTACGGGAACATCAAAATCCTATGTAAGGTCGCTCTGA
```

Fig. 2B

```
MSIMGLKVNVSAIFMAVLLTLQTPTGQIHWGNLSKIGVVGIGSASYKVMTRSSHQSLVIKLMPNITLLNNCTRVEIA
EYRRLLRTVLEPIRDALNAMTQNIRPVQSVASSRRHKRFAGVVLAGAALGVATAAQITAGIALHQSMLNSQAIDNLR
ASLETTNQAIEAIRQAGQEMILAVQGVQDYINNELIPSMNQLSCDLIGQKLGLKLLRYYTEILSLFGPSLRDPISAE
ISIQALSYALGGDINKVLEKLGYSGGDLLGILESRGIKARITHVDTESYFIVLSIAYPTLSEIKGVIVHRLEGVSYN
IGSQEWYTTVPKYVATQGYLISNFDESSCTFMPEGTVCSQNALYPMSPLLQECLRGSTKSCARTLVSGSFGNRFILS
QGNLIANCASILCKCYTTGTIINQDPDKILTYIAADHCPVVEVNGVTIQVGSRRYPDAVYLHRIDLGPPISLERLDV
GTNLGNAIAKLEDAKELLESSDQILRSMKGLSSTSIVYILIAVCLGGLIGIPALICCCRGRCNKKGEQVGMSRPGLK
PDLTGTSKSYVRSL
```

Fig. 3A

ATGGGAAGTAGGATAGTCATTAACAGAGAACATCTTATGATTGATAGACCTTATGTTTTGCTGGCTGTTCTGTTTGT
CATGTTTCTGAGCTTGATCGGGTTGCTAGCCATTGCAGGAATTCGACTTCATCGGGCAGCCATCTACACCGCAGAGA
TCCATAAAAGCCTCAGCACCAATCTAGATGTAACTAACTCAATCGAGCATCAGGTCAAGGACGTGCTGACACCACTC
TTCAAAATCATCGGTGATGAAGTGGGCCTGAGGACACCTCAGAGATTCACTGACCTAGTGAAATTCATCTCTGACAA
GATTAAATTCCTTAATCCGGATAGGGAGTACGACTTCAGAGATCTCACTTGGTGTATCAACCCGCCAGAGAGAATCA
AATTGGATTATGATCAATACTGTGCAGATGTGGCTGCTGAAGAGCTCATGAATGCATTGGTGAACTCAACTCTACTG
GAGACCAGAACAACCAATCAGTTCCTAGCTGTCTCAAAGGGAAACTGCTCAGGGCCCACTACAATCAGAGGTCAATT
CTCAAACATGTCGCTGTCCCTGTTAGACTTGTATTTAGGTCGAGGTTACAATGTGTCATCTATAGTCACTATGACAT
CCCAGGGAATGTATGGGGGAACTTACCTAGTGGAAAAGCCTAATCTGAGCAGCAAAAGGTCAGAGTTGTCACAACTG
AGCATGTACCGAGTGTTTGAAGTAGGTGTTATCAGAAATCGGGTTTGGGGCTCCGGTGTTCCATATGACAAACTA
TCTTGAGCAACCAGTCAGTAATGATCTCAGCAACTGTATGGTGGCTTTGGGGGAGCTCAAACTCGCAGCCCTTTGTC
ACGGGGAAGATTCTATCACAATTCCCTATCAGGGATCAGGGAAAGGTGTCAGCTTCCAGCTCGTCAAGCTAGGTGTC
TGGAAATCCCCAACCGACATGCAATCCTGGGTCCCCTTATCAACGGATGATCCAGTGATAGACAGGCTTTACCTCTC
ATCTCACAGAGGTGTTATCGCTGACAACCAAGCAAAATGGGCTGTCCCGACAACACGAACAGATGACAAGTTGCGAA
TGGAGACATGCTTCCAACAGGCGTGTAAGGGTAAAATCCAAGCACTCTGCGAGAATCCCGAGTGGGCACCATTGAAG
GATAACAGGATTCCTTCATACGGGGTCTTGTCTGTTGATCTGAGTCTGACAGTTGAGCTTAAAATCAAAATTGCTTC
GGGATTCGGGCCATTGATCACACACGGTTCAGGGATGGACCTATACAAATCCAACCACAACAATGTGTATTGGCTGA
CTATCCCGCCAATGAAGAACCTAGCCTTAGGTGTAATCAACACATTGGAGTGGATACCGAGATTCAAGGTTAGTCCC
TACCTCTTCACTGTCCCAATTAAGGAAGCAGGCGGAGACTGCCATGCCCCAACATACCTACCTGCGGAGGTGGATGG
TGATGTCAAACTCAGTTCCAATCTGGTGATTCTACCTGGTCAAGATCTCCAATATGTTTTGGCAACCTACGATACTT
CCAGGGTTGAACATGCTGTGGTTTATTACGTTTACAGCCCAAGCCGCTCATTTTCTTACTTTTATCCTTTTAGGTTG
CCTATAAAGGGGGTCCCCATCGAATTACAAGTGGAATGCTTCACATGGGACCAAAAACTCTGGTGCCGTCACTTCTG
TGTGCTTGCGGACTCAGAATCTGGTGGACATATCACTCACTCTGGGATGGTGGGCATGGGAGTCAGCTGCACAGTCA
CCCGGGAAGATGGAACCAATCGCAGA

Fig. 3B

ATGAGTAGGATAGTCATTAACAGAGAACATCTTATGATTGATAGACCTTATGTTTTGCTGGCTGTTCTGTTTGTCAT
GTTTCTGAGCTTGATCGGGTTGCTAGCCATTGCAGGAATTCGACTTCATCGGGCAGCCATCTACACCGCAGAGATCC
ATAAAAGCCTCAGCACCAATCTAGATGTAACTAACTCAATCGAGCATCAGGTCAAGGACGTGCTGACACCACTCTTC
AAAATCATCGGTGATGAAGTGGGCCTGAGGACACCTCAGAGATTCACTGACCTAGTGAAATTCATCTCTGACAAGAT
TAAATTCCTTAATCCGGATAGGGAGTACGACTTCAGAGATCTCACTTGGTGTATCAACCCGCCAGAGAGAATCAAAT
TGGATTATGATCAATACTGTGCAGATGTGGCTGCTGAAGAGCTCATGAATGCATTGGTGAACTCAACTCTACTGGAG
ACCAGAACAACCAATCAGTTCCTAGCTGTCTCAAAGGGAAACTGCTCAGGGCCCACTACAATCAGAGGTCAATTCTC
AAACATGTCGCTGTCCCTGTTAGACTTGTATTTAGGTCGAGGTTACAATGTGTCATCTATAGTCACTATGACATCCC
AGGGAATGTATGGGGGAACTTACCTAGTGGAAAAGCCTAATCTGAGCAGCAAAAGGTCAGAGTTGTCACAACTGAGC
ATGTACCGAGTGTTTGAAGTAGGTGTTATCAGAAATCGGGTTTGGGGCTCCGGTGTTCCATATGACAAACTATCT
TGAGCAACCAGTCAGTAATGATCTCAGCAACTGTATGGTGGCTTTGGGGGAGCTCAAACTCGCAGCCCTTTGTCACG
GGGAAGATTCTATCACAATTCCCTATCAGGGATCAGGGAAAGGTGTCAGCTTCCAGCTCGTCAAGCTAGGTGTCTGG
AAATCCCCAACCGACATGCAATCCTGGGTCCCCTTATCAACGGATGATCCAGTGATAGACAGGCTTTACCTCTCATC
TCACAGAGGTGTTATCGCTGACAACCAAGCAAAATGGGCTGTCCCGACAACACGAACAGATGACAAGTTGCGAATGG
AGACATGCTTCCAACAGGCGTGTAAGGGTAAAATCCAAGCACTCTGCGAGAATCCCGAGTGGGCACCATTGAAGGAT
AACAGGATTCCTTCATACGGGGTCTTGTCTGTTGATCTGAGTCTGACAGTTGAGCTTAAAATCAAAATTGCTTCGGG
ATTCGGGCCATTGATCACACACGGTTCAGGGATGGACCTATACAAATCCAACCACAACAATGTGTATTGGCTGACTA
TCCCGCCAATGAAGAACCTAGCCTTAGGTGTAATCAACACATTGGAGTGGATACCGAGATTCAAGGTTAGTCCCTAC
CTCTTCACTGTCCCAATTAAGGAAGCAGGCGGAGACTGCCATGCCCCAACATACCTACCTGCGGAGGTGGATGGTGA
TGTCAAACTCAGTTCCAATCTGGTGATTCTACCTGGTCAAGATCTCCAATATGTTTTGGCAACCTACGATACTTCCA
GGGTTGAACATGCTGTGGTTTATTACGTTTACAGCCCAAGCCGCTCATTTTCTTACTTTTATCCTTTTAGGTTGCCT
ATAAAGGGGGTCCCCATCGAATTACAAGTGGAATGCTTCACATGGGACCAAAAACTCTGGTGCCGTCACTTCTGTGT
GCTTGCGGACTCAGAATCTGGTGGACATATCACTCACTCTGGGATGGTGGGCATGGGAGTCAGCTGCACAGTCACCC
GGGAAGATGGAACCAATCGCAGA

Fig. 3C

ATGGCTGCCGCAGCGAACAGAGAACATCTTATGATTGATAGACCTTATGTTTTGCTGGCTGTTCTGTTTGTCATGTT
TCTGAGCTTGATCGGGTTGCTAGCCATTGCAGGAATTCGACTTCATCGGGCAGCCATCTACACCGCAGAGATCCATA
AAAGCCTCAGCACCAATCTAGATGTAACTAACTCAATCGAGCATCAGGTCAAGGACGTGCTGACACCACTCTTCAAA
ATCATCGGTGATGAAGTGGGCCTGAGGACACCTCAGAGATTCACTGACCTAGTGAAATTCATCTCTGACAAGATTAA
ATTCCTTAATCCGGATAGGGAGTACGACTTCAGAGATCTCACTTGGTGTATCAACCCGCCAGAGAGAATCAAATTGG
ATTATGATCAATACTGTGCAGATGTGGCTGCTGAAGAGCTCATGAATGCATTGGTGAACTCAACTCTACTGGAGACC
AGAACAACCAATCAGTTCCTAGCTGTCTCAAAGGGAAACTGCTCAGGGCCCACTACAATCAGAGGTCAATTCTCAAA
CATGTCGCTGTCCCTGTTAGACTTGTATTTAGGTCGAGGTTACAATGTGTCATCTATAGTCACTATGACATCCCAGG
GAATGTATGGGGAACTTACCTAGTGGAAAAGCCTAATCTGAGCAGCAAAAGGTCAGAGTTGTCACAACTGAGCATG
TACCGAGTGTTTGAAGTAGGTGTTATCAGAAATCCGGGTTTGGGGGCTCCGGTGTTCCATATGACAAACTATCTTGA
GCAACCAGTCAGTAATGATCTCAGCAACTGTATGGTGGCTTTGGGGGAGCTCAAACTCGCAGCCCTTTGTCACGGGG
AAGATTCTATCACAATTCCCTATCAGGGATCAGGGAAAGGTGTCAGCTTCCAGCTCGTCAAGCTAGGTGTCTGGAAA
TCCCCAACCGACATGCAATCCTGGGTCCCCTTATCAACGGATGATCCAGTGATAGACAGGCTTTACCTCTCATCTCA
CAGAGGTGTTATCGCTGACAACCAAGCAAAATGGGCTGTCCCGACAACACGAACAGATGACAAGTTGCGAATGGAGA
CATGCTTCCAACAGGCGTGTAAGGGTAAAATCCAAGCACTCTGCGAGAATCCCGAGTGGGCACCATTGAAGGATAAC
AGGATTCCTTCATACGGGGTCTTGTCTGTTGATCTGAGTCTGACAGTTGAGCTTAAAATCAAAATTGCTTCGGATT
CGGGCCATTGATCACACACGGTTCAGGGATGGACCTATACAAATCCAACCACAACAATGTGTATTGGCTGACTATCC
CGCCAATGAAGAACCTAGCCTTAGGTGTAATCAACACATTGGAGTGGATACCGAGATTCAAGGTTAGTCCCTACCTC
TTCACTGTCCCAATTAAGGAAGCAGGCGGAGACTGCCATGCCCCAACATACCTACCTGCGGAGGTGGATGGTGATGT
CAAACTCAGTTCCAATCTGGTGATTCTACCTGGTCAAGATCTCCAATATGTTTTGGCAACCTACGATACTTCCAGGG
TTGAACATGCTGTGGTTTATTACGTTTACAGCCCAAGCCGCTCATTTTCTTACTTTTATCCTTTTAGGTTGCCTATA
AAGGGGGTCCCCATCGAATTACAAGTGGAATGCTTCACATGGGACCAAAAACTCTGGTGCCGTCACTTCTGTGTGCT
TGCGGACTCAGAATCTGGTGGACATATCACTCACTCTGGGATGGTGGGCATGGGAGTCAGCTGCACAGTCACCCGGG
AAGATGGAACCAATCGCAGA

Fig. 3D

MGSRIVINREHLMIDRPYVLLAVLFVMFLSLIGLLAIAGIRLHRAAIYTAEIHKSLSTNLDVTNSIEHQVKDVLTPL
FKIIGDEVGLRTPQRFTDLVKFISDKIKFLNPDREYDFRDLTWCINPPERIKLDYDQYCADVAAEELMNALVNSTLL
ETRTTNQFLAVSKGNCSGPTTIRGQFSNMSLSLLDLYLGRGYNVSSIVTMTSQGMYGGTYLVEKPNLSSKRSELSQL
SMYRVFEVGVIRNPGLGAPVFHMTNYLEQPVSNDLSNCMVALGELKLAALCHGEDSITIPYQGSGKGVSFQLVKLGV
WKSPTDMQSWVPLSTDDPVIDRLYLSSHRGVIADNQAKWAVPTTRTDDKLRMETCFQQACKGKIQALCENPEWAPLK
DNRIPSYGVLSVDLSLTVELKIKIASGFGPLITHGSGMDLYKSNHNNVYWLTIPPMKNLALGVINTLEWIPRFKVSP
YLFTVPIKEAGGDCHAPTYLPAEVDGDVKLSSNLVILPGQDLQYVLATYDTSRVEHAVVYYVYSPSRSFSYFYPFRL
PIKGVPIELQVECFTWDQKLWCRHFCVLADSESGGHITHSGMVGMGVSCTVTREDGTNRR

Fig. 3E

ATGTCCATCATGGGTCTCAAGGTGAACGTCTCTGCCATATTCATGGCAGTACTGTTAACTCTCCAAACACCCACCGG
TCAAATCCATTGGGGCAATCTCTCTAAGATAGGGGTGGTAGGAATAGGAAGTGCAAGCTACAAAGTTATGACTCGTT
CCAGCCATCAATCATTAGTCATAAAATTAATGCCCAATATAACTCTCCTCAATAACTGCACGAGGGTAGAGATTGCA
GAATACAGGAGACTACTGAGAACTGTTTTGGAACCAATTAGAGATGCACTTAATGCAATGACCCAGAATATAAGACC
GGTTCAGAGTGTAGCTTCAAGTAGGAGACACAAGAGATTTGCGGGAGTAGTCCTGGCAGGTGCGGCCCTAGGCGTTG
CCACAGCTGCTCAGATAACAGCCGGCATTGCACTTCACCAGTCCATGCTGAACTCTCAAGCCATCGACAATCTGAGA
GCGAGCCTGGAAACTACTAATCAGGCAATTGAGGCAATCAGACAAGCAGGGCAGGAGATGATATTGGCTGTTCAGGG
TGTCCAAGACTACATCAATAATGAGCTGATACCGTCTATGAACCAACTATCTTGTGATTTAATCGGCCAGAAGCTCG
GGCTCAAATTGCTCAGATACTATACAGAAATCCTGTCATTATTTGGCCCCAGCTTACGGGACCCCATATCTGCGGAG
ATATCTATCCAGGCTTTGAGCTATGCGCTTGGAGGAGACATCAATAAGGTGTTAGAAAAGCTCGGATACAGTGGAGG
TGATTTACTGGGCATCTTAGAGAGCAGAGGAATAAAGGCCCGGATAACTCACGTCGACACAGAGTCCTACTTCATTG
TCCTCAGTATAGCCTATCCGACGCTGTCCGAGATTAAGGGGGTGATTGTCCACCGGCTAGAGGGGTCTCGTACAAC
ATAGGCTCTCAAGAGTGGTATACCACTGTGCCCAAGTATGTCGCAACCCAAGGGTACCTTATCTCGAATTTTGATGA
GTCATCGTGTACTTTCATGCCAGAGGGAACTGTGTGCAGCCAAAATGCCTTGTACCCGATGAGTCCTCTGCTCCAAG
AATGCCTCCGGGGGTCCACTAAGTCCTGTGCTCGTACACTCGTATCCGGGTCTTTTGGGAACCGGTTCATTTTATCA
CAAGGGAACCTAATAGCCAATTGTGCATCAATCCTTTGCAAGTGTTACACAACAGGAACGATCATTAATCAAGACCC
TGACAAGATCCTAACATACATTGCTGCCGATCACTGCCCGGTAGTCGAGGTGAACGGCGTGACCATCCAAGTCGGGA
GCAGGAGGTATCCAGACGCTGTGTACTTGCACAGAATTGACCTCGGTCCTCCCATATCATTGGAGAGGTTGGACGTA
GGGACAAATCTGGGGAATGCAATTGCTAAGTTGGAGGATGCCAAGGAATTGTTGGAGTCATCGGACCAGATATTGAG
GAGTATGAAAGGTTTATCGAGCACTAGCATAGTCTACATCCTGATTGCAGTGTGTCTTGGAGGGTTGATAGGGATCC
CCGCTTTAATATGTTGCTGCAGGGGGCGTTGA

Fig. 3F

MSIMGLKVNVSAIFMAVLLTLQTPTGQIHWGNLSKIGVVGIGSASYKVMTRSSHQSLVIKLMPNITLLNNCTRVEIA
EYRRLLRTVLEPIRDALNAMTQNIRPVQSVASSRRHKRFAGVVLAGAALGVATAAQITAGIALHQSMLNSQAIDNLR
ASLETTNQAIEAIRQAGQEMILAVQGVQDYINNELIPSMNQLSCDLIGQKLGLKLLRYYTEILSLFGPSLRDPISAE
ISIQALSYALGGDINKVLEKLGYSGGDLLGILESRGIKARITHVDTESYFIVLSIAYPTLSEIKGVIVHRLEGVSYN
IGSQEWYTTVPKYVATQGYLISNFDESSCTFMPEGTVCSQNALYPMSPLLQECLRGSTKSCARTLVSGSFGNRFILS
QGNLIANCASILCKCYTTGTIINQDPDKILTYIAADHCPVVEVNGVTIQVGSRRYPDAVYLHRIDLGPPISLERLDV
GTNLGNAIAKLEDAKELLESSDQILRSMKGLSSTSIVYILIAVCLGGLIGIPALICCCRGR

Fig. 3G

ATGGCTGCCGCAGCGAACAGAGAACATCTTATGATTGATAGACCTTATGTTTTGCTGGCTGTTCTGTTTGTCATGTT
TCTGAGCTTGATCGGGTTGCTAGCCATTGCAGGAATTCGACTTCATCGGGCAGCCATCTACACCGCAGAGATCCATA
AAAGCCTCAGCACCAATCTAGATGTAACTAACTCAATCGAGCATCAGGTCAAGGACGTGCTGACACCACTCTTCAAA
ATCATCGGTGATGAAGTGGGCCTGAGGACACCTCAGAGATTCACTGACCTAGTGAAATTCATCTCTGACAAGATTAA
ATTCCTTAATCCGGATAGGGAGTACGACTTCAGAGATCTCACTTGGTGTATCAACCCGCCAGAGAGAATCAAATTGG
ATTATGATCAATACTGTGCAGATGTGGCTGCTGAAGAGCTCATGAATGCATTGGTGAACTCAACTCTACTGGAGACC
AGAACAACCAATCAGTTCCTAGCTGTCTCAAAGGGAAACTGCTCAGGGCCCACTACAATCAGAGGTCAATTCTCAAA
CATGTCGCTGTCCCTGTTAGACTTGTATTTAGGTCGAGGTTACAATGTGTCATCTATAGTCACTATGACATCCCAGG
GAATGTATGGGGAACTTACCTAGTGGAAAAGCCTAATCTGAGCAGCAAAAGGTCAGAGTTGTCACAACTGAGCATG
TACCGAGTGTTTGAAGTAGGTGTTATCAGAAATCCGGGTTTGGGGGCTCCGGTGTTCCATATGACAAACTATCTTGA
GCAACCAGTCAGTAATGATCTCAGCAACTGTATGGTGGCTTTGGGGGAGCTCAAACTCGCAGCCCTTTGTCACGGGG
AAGATTCTATCACAATTCCCTATCAGGGATCAGGGAAAGGTGTCAGCTTCCAGCTCGTCAAGCTAGGTGTCTGGAAA
TCCCCAACCGACATGCAATCCTGGGTCCCCTTATCAACGGATGATCCAGTGATAGACAGGCTTTACCTCTCATCTCA
CAGAGGTGTTATCGCTGACAACCAAGCAAAATGGGCTGTCCCGACAACACGAACAGATGACAAGTTGCGAATGGAGA
CATGCTTCCAACAGGCGTGTAAGGGTAAAATCCAAGCACTCTGCGAGAATCCCGAGTGGGCACCATTGAAGGATAAC
AGGATTCCTTCATACGGGGTCTTGTCTGTTGATCTGAGTCTGACAGTTGAGCTTAAAATCAAAATTGCTTCGGGATT
CGGGCCATTGATCACACACGGTTCAGGGATGGACCTATACAAATCCAACCACAACAATGTGTATTGGCTGACTATCC
CGCCAATGAAGAACCTAGCCTTAGGTGTAATCAACACATTGGAGTGGATACCGAGATTCAAGGTTAGTCCCTACCTC
TTCACTGTCCCAATTAAGGAAGCAGGCGGAGACTGCCATGCCCCAACATACCTACCTGCGGAGGTGGATGGTGATGT
CAAACTCAGTTCCAATCTGGTGATTCTACCTGGTCAAGATCTCCAATATGTTTTGGCAACCTACGATACTTCCAGGG
TTGAACATGCTGTGGTTTATTACGTTTACAGCCCAAGCCGCTCATTTTCTTACTTTTATCCTTTTAGGTTGCCTATA
AAGGGGGTCCCCATCGAATTACAAGTGGAATGCTTCACATGGGACCAAAAACTCTGGTGCCGTCACTTCTGTGTGCT
TGCGGACTCAGAATCTGGTGGACATATCACTCACTCTGGGATGGTGGGCATGGGAGTCAGCTGCACAGTCACCCGGG
AAGATGGAACCAATCGCAGA

Fig. 4A

| | TM | CD |
|---|---|---|
| F$_{Edm}$ wt | LICCC | RGRCNKKGEQVGMSRPGLKPDLTGTSKSYVRSL |
| FcΔ30 | LICCC | RGR |

Fig. 4B

| | CD | TM |
|---|---|---|
| H$_{Edm}$ wt | MSPQRDRINAFYKDNPHPKGSRIVINREHLMIDR | PYVL |
| HcΔ18 | M..................GSRIVINREHLMIDR | PYVL |
| HcΔ19 | M..................SRIVINREHLMIDR | PYVL |
| HcΔ24+4A | M..................AAAANREHLMIDR | PYVL |

Fig. 5A

ATGGGAAGTAGGATAGTCATTAACAGAGAACATCTTATGATTGATAGACCTTATGTTTTGCTGGCTGTTCTGTTTGT
CATGTTTCTGAGCTTGATCGGGTTGCTAGCCATTGCAGGAATTCGACTTCATCGGGCAGCCATCTACACCGCAGAGA
TCCATAAAAGCCTCAGCACCAATCTAGATGTAACTAACTCAATCGAGCATCAGGTCAAGGACGTGCTGACACCACTC
TTCAAAATCATCGGTGATGAAGTGGGCCTGAGGACACCTCAGAGATTCACTGACCTAGTGAAATTCATCTCTGACAA
GATTAAATTCCTTAATCCGGATAGGGAGTACGACTTCAGAGATCTCACTTGGTGTATCAACCCGCCAGAGAGAATCA
AATTGGATTATGATCAATACTGTGCAGATGTGGCTGCTGAAGAGCTCATGAATGCATTGGTGAACTCAACTCTACTG
GAGACCAGAACAACCAATCAGTTCCTAGCTGTCTCAAAGGGAAACTGCTCAGGGCCCACTACAATCAGAGGTCAATT
CTCAAACATGTCGCTGTCCCTGTTAGACTTGTATTTAGGTCGAGGTTACAATGTGTCATCTATAGTCACTATGACAT
CCCAGGGAATGTATGGGGGAACTTACCTAGTGGAAAAGCCTAATCTGAGCAGCAAAAGGTCAGAGTTGTCACAACTG
AGCATGTACCGAGTGTTTGAAGTAGGTGTTATCAGAAATCCGGGTTGGGGGCTCCGGTGTTCCATATGACAAACTA
TCTTGAGCAACCAGTCAGTAATGATCTCAGCAACTGTATGGTGGCTTTGGGGGAGCTCAAACTCGCAGCCCTTTGTC
ACGGGGAAGATTCTATCACAATTCCCTATCAGGGATCAGGGAAAGGTGTCAGCTTCCAGCTCGTCAAGCTAGGTGTC
TGGAAATCCCCAACCGACATGCAATCCTGGGTCCCCTTATCAACGGATGATCCAGTGATAGACAGGCTTTACCTCTC
ATCTCACAGAGGTGTTATCGCTGACAACCAAGCAAATGGGCTGTCCCGACAACACGAACAGATGACAAGTTGCGAA
TGGAGACATGCTTCCAACAGGCGTGTAAGGGTAAAATCCAAGCACTCTGCGAGAATCCCGAGTGGGCACCATTGAAG
GATAACAGGATTCCTTCATACGGGGTCTTGTCTGTTGATCTGAGTCTGACAGTTGAGCTTAAAATCAAAATTGCTTC
GGGATTCGGGCCATTGATCACACACGGTTCAGGGATGGACCTATACAAATCCAACCACAACAATGTGTATTGGCTGA
CTATCCCGCCAATGAAGAACCTAGCCTTAGGTGTAATCAACACATTGGAGTGGATACCGAGATTCAAGGTTAGTCCC
<u>GC</u>ACTCTTCACTGTCCCAATTAAGGAAGCAGGCGGAGACTGCCATGCCCCAACATACCTACCTGCGGAGGTGGATGG
TGATGTCAAACTCAGTTCCAATCTGGTGATTCTACCTGGTCAAGATCTCCAATATGTTTTGGCAACCTACGATACTT
CC<u>GCCG</u>GTTGAACATGCTGTGGTTTATTACGTTTACAGCCCAAGCCG<u>CCTATCG</u>TCTTACTTTTATCCTTTTAGGTTG
CCTATAAAGGGGGTCCCCATCGAATTACAAGTGGAATGCTTCACATGGGACCAAAAACTCTGGTGCCGTCACTTCTG
TGTGCTTGCGGACTCAGAATCTGGTGGACATATCACTCACTCTGGGATGGTGGGCATGGGAGTCAGCTGCACAGTCA
CCCGGGAAGATGGAACCAATGC<u>GGCCCAGCCGGCC</u>ATCGAGGGAAGGATGGCTCAGGTTCAGCTGGTCCAGTCAGGG
GCTGAGCTGGTGAAGCCTGGGGCCTCAGTGAAGATGTCCTGCAAGGCTTCTGGCTACACATTTACCAGTTACAATAT
GCACTGGGTAAAGCAGACACCTGGACAGGGCCTGGAATGGATTGGAGCTATTTATCCAGGAAATGGTGATACTTCCT
ACAATCAGAAGTTCAAAGGCAAGGCCACATTGACTGCAGACAAATCCTCCAGCACAGCCTACATGCAGCTCAGCAGC
CTGACATCTGAGGACTCTGCGGTCTATTACTGTGCAAGAGCGCAATTACGACCTAACTACTGGTACTTCGATGTCTG
GGGCGCAGGGACCACGGTCACCGTGAGCAAGATCTCTGGTGGCGGTGGCTCGGGCGGTGGTGGGTCGGGTGGCGGAG
GCTCGGGTGGCTCGAGCGACATCGTGCTGTCGCAGTCTCCAGCAATCCTGTCTGCATCTCCAGGGGAGAAGGTCACA
ATGACTTGCAGGGCCAGCTCAAGTGTAAGTTACATGCACTGGTACCAGCAGAAGCCAGGATCCTCCCCCAAACCCTG
GATTTATGCCACATCCAACCTGGCTTCTGGAGTCCCTGCTCGCTTCAGTGGCAGTGGGTCTGGGACCTCTTACTCTC
TCACAATCAGCAGAGTGGAGGCTGAAGATGCTGCCACTTATTACTGCCAGCAGTGGATTAGTAACCCACCCACGTTC
GGTGCTGGGACCAAGCTGGAGCTGAAG<u>GCGGCCGCAAGAGGTTCTCATCACCATCACCATCACTAA</u>

Fig. 5B

<u>MGSRIVINREHLMIDR</u>PYVLLAVLFVMFLSLIGLLAIAGIRLHRAAIYTAEIHKSLSTNLDVTNSIEHQVKDVLTPL
FKIIGDEVGLRTPQRFTDLVKFISDKIKFLNPDREYDFRDLTWCINPPERIKLDYDQYCADVAAEELMNALVNSTLL
ETRTTNQFLAVSKGNCSGPTTIRGQFSNMSLSLLDLYLGRGYNVSSIVTMTSQGMYGGTYLVEKPNLSSKRSELSQL
SMYRVFEVGVIRNPGLGAPVFHMTNYLEQPVSNDLSNCMVALGELKLAALCHGEDSITIPYQGSGKGVSFQLVKLGV
WKSPTDMQSWVPLSTDDPVIDRLYLSSHRGVIADNQAKWAVPTTRTDDKLRMETCFQQACKGKIQALCENPEWAPLK
DNRIPSYGVLSVDLSLTVELKIKIASGFGPLITHGSGMDLYKSNHNNVYWLTIPPMKNLALGVINTLEWIPRFKVSP
<u>A</u>LFTVPIKEAGGDCHAPTYLPAEVDGDVKLSSNLVILPGQDLQYVLATYDTS<u>A</u>VEHAVVYYVSPSR<u>LS</u>SYFYPFRL
PIKGVPIELQVECFTWDQKLWCRHFCVLADSESGGHITHSGMVGMGVSCTVTREDGTNAA<u>Q</u>PAIEGRMAQVQLVQSG
AELVKPGASVKMSCKASGYTFTSYNMHWVKQTPGQGLEWIGAIYPGNGDTSYNQKFKGKATLTADKSSSTAYMQLSS
LTSEDSAVYYCARAQLRPNYWYFDVWGAGTTVTVSKISGGGGSGGGGSGGGGSGGSSDIVLSQSPAILSASPGEKVT
MTCRASSSVSYMHWYQQKPGSSPKPWIYATSNLASGVPARFSGSGSGTSYSLTISRVEAEDAATYYCQQWISNPPTF
GAGTKLELKAA<u>ARGSHHHHHH</u>

Fig. 5C pCG-HmutscFvCD20d18
7224 bps

Fig. 6A

GGCCCAGCCGGCCATGGCCAATAGTGACTCTGAATGTCCCCTGTCCCACGATGGGTACTGCCTCCATGATGGTGTGT
GCATGTATATTGAAGCATTGGACAAGTATGCATGCAACTGTGTTGTTGGCTACATCGGGGAGCGATGTCAGTACCGA
GACCTGAAGTGGTGGGAACTGCGCGCGGCCGC

Fig. 6B

AQPAMANSDSECPLSHDGYCLHDGVCMYIEALDKYACNCVVGYIGERCQYRDLKWWELRAAA

| F / H variants of the HIV-1 vectors | Relative Titer reduction with AZT |
|---|---|
| FcΔ30 HcΔ18 | ~ 97% |
| FcΔ30 HcΔ19 | ~ 90% |
| FcΔ30 HcΔ24+4A | ~ 90% |
| pos. control: VSV-G | ~ 99% |

FIG. 13A without AZT    with AZT

GFP → cDNA3.1(-)
GluR4
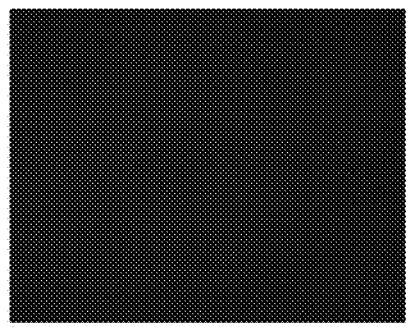
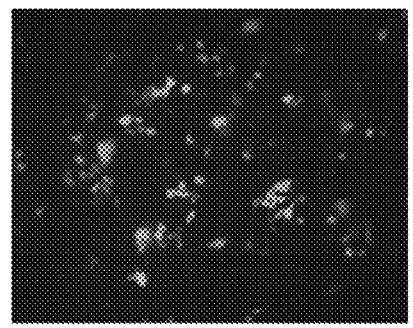
FIG. 19A
FIG. 19B
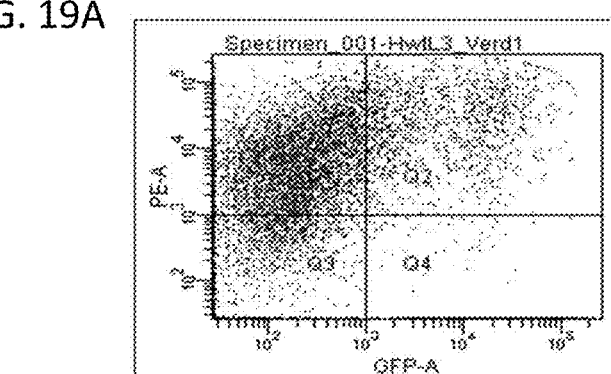
*1:10*
FIG. 19C
*GluR4*
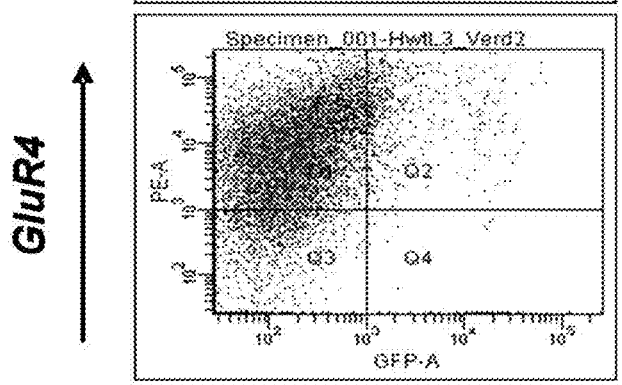
*1:100*
FIG. 19D
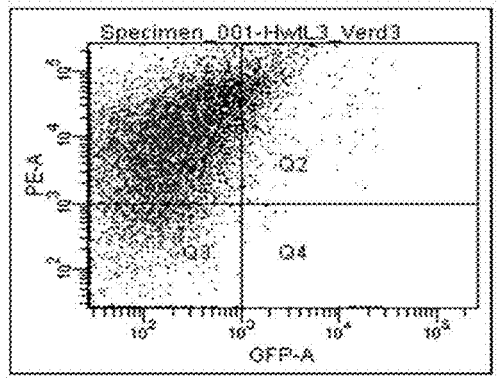
*1:1000*
FIG. 19E
*GFP*

VSV-G / HIV    MOI 2 anti-CD20 MeV / HIV    MOI 2

VSV-G / HIV     MOI 150

SEQUENCE LISTING

<160> NUMBER OF SEQ ID NOS: 49

<210> SEQ ID NO 1
<211> LENGTH: 2607
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Truncated and mutated (Y481A, R533A, S548L,
      F549S) MeV H protein (HcDelta18) fused to single chain antibody
      directed to human CD20 (scFvCD20)

<400> SEQUENCE: 1
atgggaagta ggatagtcat taacagagaa catcttatga ttgatagacc ttatgttttg      60
ctggctgttc tgtttgtcat gtttctgagc ttgatcgggt tgctagccat tgcaggaatt     120
cgacttcatc gggcagccat ctacaccgca gagatccata aaagcctcag caccaatcta     180
gatgtaacta actcaatcga gcatcaggtc aaggacgtgc tgacaccact cttcaaaatc     240
atcggtgatg aagtgggcct gaggacacct cagagattca ctgacctagt gaaattcatc     300
tctgacaaga ttaaattcct taatccggat agggagtacg acttcagaga tctcacttgg     360
tgtatcaacc cgccagagag aatcaaattg gattatgatc aatactgtgc agatgtggct     420
gctgaagagc tcatgaatgc attggtgaac tcaactctac tggagaccag aacaaccaat     480
cagttcctag ctgtctcaaa gggaaactgc tcagggccca ctaacatcag aggtcaattc     540
tcaaacatgt cgctgtccct gttagacttg tatttaggtc gaggttacaa tgtgtcatct     600
atagtcacta tgacatccca gggaatgtat gggggaactt acctagtgga aaagcctaat     660
ctgagcagca aaaggtcaga gttgtcacaa ctgagcatgt accgagtgtt tgaagtaggt     720
gttatcagaa atccgggttt gggggctccg gtgttccata tgacaaacta tcttgagcaa     780
ccagtcagta tgatctcag caactgtatg gtggctttgg gggagctcaa actcgcagcc     840
ctttgtcacg gggaagattc tatcacaatt ccctatcagg gatcagggaa aggtgtcagc     900
ttccagctcg tcaagctagg tgtctggaaa tccccaaccg acatgcaatc ctgggtcccc     960
ttatcaacgg atgatccagt gatagacagg ctttacctct catctcacag aggtgttatc    1020
gctgacaacc aagcaaaatg ggctgtcccg acaacacgaa cagatgacaa gttgcgaatg    1080
gagacatgct tccaacaggc agtaagggt aaaatccaag cactctgcga gaatcccgag    1140
tgggcaccat tgaaggataa caggattcct tcatacgggg tcttgtctgt tgatctgagt    1200

```
ctgacagttg agcttaaaat caaaattgct tcgggattcg ggccattgat cacacacggt    1260
tcagggatgg acctatacaa atccaaccac aacaatgtgt attggctgac tatcccgcca    1320
atgaagaacc tagccttagg tgtaatcaac acattggagt ggataccgag attcaaggtt    1380
agtcccgcac tcttcactgt cccaattaag gaagcaggcg gagactgcca tgccccaaca    1440
tacctacctg cggaggtgga tggtgatgtc aaactcagtt ccaatctggt gattctacct    1500
ggtcaagatc tccaatatgt tttggcaacc tacgatactt ccgcggttga acatgctgtg    1560
gtttattacg tttacagccc aagccgccta tcgtcttact tttatccttt taggttgcct    1620 ataaagggggg tccccatcga attacaagtg gaatgcttca catgggacca aaaactctgg    1680
tgccgtcact tctgtgtgct tgcggactca gaatctggtg acatatcac tcactctggg    1740 atggtgggca tggagtcag ctgcacagtc acccgggaag atggaaccaa tgcggcccag    1800
ccggccatcg agggaaggat ggctcaggtt cagctggtcc agtcaggggc tgagctggtg    1860
aagcctgggg cctcagtgaa gatgtcctgc aaggcttctg gctacacatt taccagttac    1920
aatatgcact gggtaaagca gacacctgga cagggcctgg aatggattgg agctatttat    1980
ccaggaaatg gtgatacttc ctacaatcag aagttcaaag gcaaggccac attgactgca    2040
gacaaatcct ccagcacagc ctacatgcag ctcagcagcc tgacatctga ggactctgcg    2100
gtctattact gtgcaagagc gcaattacga cctaactact ggtacttcga tgtctggggc    2160
gcagggacca cggtcaccgt gagcaagatc tctggtggcg gtggctcggg cggtggtggg    2220
tcgggtggcg gaggctcggg tggctcgagc gacatcgtgc tgtcgcagtc tccagcaatc    2280
ctgtctgcat ctccagggga gaaggtcaca atgacttgca gggccagctc aagtgtaagt    2340
tacatgcact ggtaccagca gaagccagga tcctccccca aaccctggat ttatgccaca    2400
tccaacctgg cttctggagt ccctgctcgc ttcagtggca gtgggtctgg gacctcttac    2460
tctctcacaa tcagcagagt ggaggctgaa gatgctgcca cttattactg ccagcagtgg    2520
attagtaacc cacccacgtt cggtgctggg accaagctgg agctgaaggc ggccgcaaga    2580
ggttctcatc accatcacca tcactaa                                       2607
```

<210> SEQ ID NO 2
<211> LENGTH: 868
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Truncated and mutated (Y481A, R533A, S548L, F549S) MeV H protein (HcDelta18) fused to single chain antibody directed to human CD20 (scFvCD20)

<400> SEQUENCE: 2

```
Met Gly Ser Arg Ile Val Ile Asn Arg Glu His Leu Met Ile Asp Arg
1               5                   10                  15

Pro Tyr Val Leu Leu Ala Val Leu Phe Val Met Phe Leu Ser Leu Ile
            20                  25                  30

Gly Leu Leu Ala Ile Ala Gly Ile Arg Leu His Arg Ala Ala Ile Tyr
        35                  40                  45

Thr Ala Glu Ile His Lys Ser Leu Ser Thr Asn Leu Asp Val Thr Asn
    50                  55                  60

Ser Ile Glu His Gln Val Lys Asp Val Leu Thr Pro Leu Phe Lys Ile
65                  70                  75                  80

Ile Gly Asp Glu Val Gly Leu Arg Thr Pro Gln Arg Phe Thr Asp Leu
```

-continued

```
                    85                  90                  95
Val Lys Phe Ile Ser Asp Lys Ile Lys Phe Leu Asn Pro Asp Arg Glu
                   100                 105                 110

Tyr Asp Phe Arg Asp Leu Thr Trp Cys Ile Asn Pro Glu Arg Ile
                   115                 120                 125

Lys Leu Asp Tyr Asp Gln Tyr Cys Ala Asp Val Ala Ala Glu Glu Leu
                   130                 135             140

Met Asn Ala Leu Val Asn Ser Thr Leu Leu Glu Thr Arg Thr Thr Asn
145                 150                 155                 160

Gln Phe Leu Ala Val Ser Lys Gly Asn Cys Ser Gly Pro Thr Thr Ile
                   165                 170                 175

Arg Gly Gln Phe Ser Asn Met Ser Leu Ser Leu Leu Asp Leu Tyr Leu
                   180                 185                 190

Gly Arg Gly Tyr Asn Val Ser Ser Ile Val Thr Met Thr Ser Gln Gly
                   195                 200                 205

Met Tyr Gly Gly Thr Tyr Leu Val Glu Lys Pro Asn Leu Ser Ser Lys
               210                 215                 220

Arg Ser Glu Leu Ser Gln Leu Ser Met Tyr Arg Val Phe Glu Val Gly
225                 230                 235                 240

Val Ile Arg Asn Pro Gly Leu Gly Ala Pro Val Phe His Met Thr Asn
                   245                 250                 255

Tyr Leu Glu Gln Pro Val Ser Asn Asp Leu Ser Asn Cys Met Val Ala
               260                 265                 270

Leu Gly Glu Leu Lys Leu Ala Ala Leu Cys His Gly Glu Asp Ser Ile
               275                 280                 285

Thr Ile Pro Tyr Gln Gly Ser Gly Lys Gly Val Ser Phe Gln Leu Val
               290                 295                 300

Lys Leu Gly Val Trp Lys Ser Pro Thr Asp Met Gln Ser Trp Val Pro
305                 310                 315                 320

Leu Ser Thr Asp Asp Pro Val Ile Asp Arg Leu Tyr Leu Ser Ser His
                   325                 330                 335

Arg Gly Val Ile Ala Asp Asn Gln Ala Lys Trp Ala Val Pro Thr Thr
                   340                 345                 350

Arg Thr Asp Asp Lys Leu Arg Met Glu Thr Cys Phe Gln Gln Ala Cys
                   355                 360                 365

Lys Gly Lys Ile Gln Ala Leu Cys Glu Asn Pro Glu Trp Ala Pro Leu
                   370                 375                 380

Lys Asp Asn Arg Ile Pro Ser Tyr Gly Val Leu Ser Val Asp Leu Ser
385                 390                 395                 400

Leu Thr Val Glu Leu Lys Ile Lys Ile Ala Ser Gly Phe Gly Pro Leu
                   405                 410                 415

Ile Thr His Gly Ser Gly Met Asp Leu Tyr Lys Ser Asn His Asn Asn
                   420                 425                 430

Val Tyr Trp Leu Thr Ile Pro Pro Met Lys Asn Leu Ala Leu Gly Val
                   435                 440                 445

Ile Asn Thr Leu Glu Trp Ile Pro Arg Phe Lys Val Ser Pro Ala Leu
                   450                 455                 460

Phe Thr Val Pro Ile Lys Glu Ala Gly Gly Asp Cys His Ala Pro Thr
465                 470                 475                 480

Tyr Leu Pro Ala Glu Val Asp Gly Asp Val Lys Leu Ser Ser Asn Leu
                   485                 490                 495

Val Ile Leu Pro Gly Gln Asp Leu Gln Tyr Val Leu Ala Thr Tyr Asp
                   500                 505                 510
```

```
Thr Ser Ala Val Glu His Ala Val Tyr Val Tyr Ser Pro Ser
        515                 520                 525

Arg Leu Ser Ser Tyr Phe Tyr Pro Phe Arg Leu Pro Ile Lys Gly Val
530                 535                 540

Pro Ile Glu Leu Gln Val Glu Cys Phe Thr Trp Asp Gln Lys Leu Trp
545                 550                 555                 560

Cys Arg His Phe Cys Val Leu Ala Asp Ser Glu Ser Gly Gly His Ile
                565                 570                 575

Thr His Ser Gly Met Val Gly Met Gly Val Ser Cys Thr Val Thr Arg
            580                 585                 590

Glu Asp Gly Thr Asn Ala Ala Gln Pro Ala Ile Glu Gly Arg Met Ala
        595                 600                 605

Gln Val Gln Leu Val Gln Ser Gly Ala Glu Leu Val Lys Pro Gly Ala
    610                 615                 620

Ser Val Lys Met Ser Cys Lys Ala Ser Gly Tyr Thr Phe Thr Ser Tyr
625                 630                 635                 640

Asn Met His Trp Val Lys Gln Thr Pro Gly Gln Gly Leu Glu Trp Ile
                645                 650                 655

Gly Ala Ile Tyr Pro Gly Asn Gly Asp Thr Ser Tyr Asn Gln Lys Phe
            660                 665                 670

Lys Gly Lys Ala Thr Leu Thr Ala Asp Lys Ser Ser Thr Ala Tyr
        675                 680                 685

Met Gln Leu Ser Ser Leu Thr Ser Glu Asp Ser Ala Val Tyr Tyr Cys
    690                 695                 700

Ala Arg Ala Gln Leu Arg Pro Asn Tyr Trp Tyr Phe Asp Val Trp Gly
705                 710                 715                 720

Ala Gly Thr Thr Val Thr Val Ser Lys Ile Ser Gly Gly Gly Ser
                725                 730                 735

Gly Gly Gly Gly Ser Gly Gly Gly Ser Gly Gly Ser Ser Asp Ile
            740                 745                 750

Val Leu Ser Gln Ser Pro Ala Ile Leu Ser Ala Ser Pro Gly Glu Lys
        755                 760                 765

Val Thr Met Thr Cys Arg Ala Ser Ser Ser Val Ser Tyr Met His Trp
770                 775                 780

Tyr Gln Gln Lys Pro Gly Ser Ser Pro Lys Pro Trp Ile Tyr Ala Thr
785                 790                 795                 800

Ser Asn Leu Ala Ser Gly Val Pro Ala Arg Phe Ser Gly Ser Gly Ser
                805                 810                 815

Gly Thr Ser Tyr Ser Leu Thr Ile Ser Arg Val Glu Ala Glu Asp Ala
            820                 825                 830

Ala Thr Tyr Tyr Cys Gln Gln Trp Ile Ser Asn Pro Pro Thr Phe Gly
        835                 840                 845

Ala Gly Thr Lys Leu Glu Leu Lys Ala Ala Arg Gly Ser His His
850                 855                 860

His His His His
865

<210> SEQ ID NO 3
<211> LENGTH: 2010
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: Truncated and mutated (Y481A, R533A, S548L, F549S) MeV H protein (HcDelta18) fused to EGF ligand

<400> SEQUENCE: 3

```
atgggaagta ggatagtcat taacagagaa catcttatga ttgatagacc ttatgttttg     60
ctggctgttc tgtttgtcat gtttctgagc ttgatcgggt tgctagccat tgcaggaatt    120
cgacttcatc gggcagccat ctacaccgca gagatccata aaagcctcag caccaatcta    180
gatgtaacta actcaatcga gcatcaggtc aaggacgtgc tgacaccact cttcaaaatc    240
atcggtgatg aagtgggcct gaggacacct cagagattca ctgacctagt gaaattcatc    300
tctgacaaga ttaaattcct taatccggat agggagtacg acttcagaga tctcacttgg    360
tgtatcaacc cgccagagag aatcaaattg gattatgatc aatactgtgc agatgtggct    420
gctgaagagc tcatgaatgc attggtgaac tcaactctac tggagaccag aacaaccaat    480
cagttcctag ctgtctcaaa gggaaactgc tcagggccca ctacaatcag aggtcaattc    540
tcaaacatgt cgctgtccct gttagacttg tatttaggtc gaggttacaa tgtgtcatct    600
atagtcacta tgacatccca gggaatgtat gggggaactt acctagtgga aaagcctaat    660
ctgagcagca aaaggtcaga gttgtcacaa ctgagcatgt accgagtgtt tgaagtaggt    720
gttatcagaa atccgggttt gggggctccg gtgttccata tgacaaacta tcttgagcaa    780
ccagtcagta atgatctcag caactgtatg gtggctttgg gggagctcaa actcgcagcc    840
ctttgtcacg gggaagattc tatcacaatt ccctatcagg gatcagggaa aggtgtcagc    900
ttccagctcg tcaagctagg tgtctggaaa tccccaaccg acatgcaatc ctgggtcccc    960
ttatcaacgg atgatccagt gatagacagg ctttacctct catctcacag aggtgttatc   1020
gctgacaacc aagcaaaatg ggctgtcccg acaacacgaa cagatgacaa gttgcgaatg   1080
gagacatgct tccaacaggc gtgtaagggt aaaatccaag cactctgcga gaatcccgag   1140
tgggcaccat tgaaggataa caggattcct tcatacgggg tcttgtctgt tgatctgagt   1200
ctgacagttg agcttaaaat caaaattgct tcgggattcg ggccattgat cacacacggt   1260
tcagggatgg acctatacaa atccaaccac aacaatgtgt attggctgac tatcccgcca   1320
atgaagaacc tagccttagg tgtaatcaac acattggagt ggataccgag attcaaggtt   1380
agtcccgcac tcttcactgt cccaattaag gaagcaggcg gagactgcca tgccccaaca   1440
tacctacctg cggaggtgga tggtgatgtc aaactcagtt ccaatctggt gattctacct   1500
ggtcaagatc tccaatatgt tttggcaacc tacgatactt ccgcggttga acatgctgtg   1560
gtttattacg tttacagccc aagccgccta tcgtcttact tttatccttt taggttgcct   1620
ataaaggggg tccccatcga attacaagtg gaatgcttca catgggacca aaaactctgg   1680
tgccgtcact tctgtgtgct tgcggactca gaatctggtg gacatatcac tcactctggg   1740
atggtgggca tgggagtcag ctgcacagtc acccgggaag atggaaccaa tgcggcccag   1800
ccggccatgg ccaatagtga ctctgaatgt cccctgtccc acgatgggta ctgcctccat   1860
gatggtgtgt gcatgtatat tgaagcattg gacaagtatg catgcaactg tgttgttggc   1920
tacatcgggg agcgatgtca gtaccgagac ctgaagtggt gggaactgcg cgcggccgca   1980
agaggttctc atcaccatca ccatcactaa                                    2010
```

<210> SEQ ID NO 4
<211> LENGTH: 669
<212> TYPE: PRT
<213> ORGANISM: Artificial Sequence
<220> FEATURE:

<223> OTHER INFORMATION: Description of Artificial Sequence: Synthetic
polypeptide
<220> FEATURE:
<223> OTHER INFORMATION: Truncated and mutated (Y481A, R533A, S548L,
F549S) MeV H protein (HcDelta18) fused to EGF ligand

<400> SEQUENCE: 4

```
Met Gly Ser Arg Ile Val Ile Asn Arg Glu His Leu Met Ile Asp Arg
1               5                   10                  15

Pro Tyr Val Leu Leu Ala Val Leu Phe Val Met Phe Leu Ser Leu Ile
            20                  25                  30

Gly Leu Leu Ala Ile Ala Gly Ile Arg Leu His Arg Ala Ala Ile Tyr
        35                  40                  45

Thr Ala Glu Ile His Lys Ser Leu Ser Thr Asn Leu Asp Val Thr Asn
    50                  55                  60

Ser Ile Glu His Gln Val Lys Asp Val Leu Thr Pro Leu Phe Lys Ile
65                  70                  75                  80

Ile Gly Asp Glu Val Gly Leu Arg Thr Pro Gln Arg Phe Thr Asp Leu
                85                  90                  95

Val Lys Phe Ile Ser Asp Lys Ile Lys Phe Leu Asn Pro Asp Arg Glu
            100                 105                 110

Tyr Asp Phe Arg Asp Leu Thr Trp Cys Ile Asn Pro Pro Glu Arg Ile
        115                 120                 125

Lys Leu Asp Tyr Asp Gln Tyr Cys Ala Asp Val Ala Ala Glu Glu Leu
130                 135                 140

Met Asn Ala Leu Val Asn Ser Thr Leu Leu Glu Thr Arg Thr Thr Asn
145                 150                 155                 160

Gln Phe Leu Ala Val Ser Lys Gly Asn Cys Ser Gly Pro Thr Thr Ile
                165                 170                 175

Arg Gly Gln Phe Ser Asn Met Ser Leu Ser Leu Leu Asp Leu Tyr Leu
            180                 185                 190

Gly Arg Gly Tyr Asn Val Ser Ser Ile Val Thr Met Thr Ser Gln Gly
        195                 200                 205

Met Tyr Gly Gly Thr Tyr Leu Val Glu Lys Pro Asn Leu Ser Ser Lys
    210                 215                 220

Arg Ser Glu Leu Ser Gln Leu Ser Met Tyr Arg Val Phe Glu Val Gly
225                 230                 235                 240

Val Ile Arg Asn Pro Gly Leu Gly Ala Pro Val Phe His Met Thr Asn
                245                 250                 255

Tyr Leu Glu Gln Pro Val Ser Asn Asp Leu Ser Asn Cys Met Val Ala
            260                 265                 270

Leu Gly Glu Leu Lys Leu Ala Ala Leu Cys His Gly Glu Asp Ser Ile
        275                 280                 285

Thr Ile Pro Tyr Gln Gly Ser Gly Lys Gly Val Ser Phe Gln Leu Val
    290                 295                 300

Lys Leu Gly Val Trp Lys Ser Pro Thr Asp Met Gln Ser Trp Val Pro
305                 310                 315                 320

Leu Ser Thr Asp Asp Pro Val Ile Asp Arg Leu Tyr Leu Ser Ser His
                325                 330                 335

Arg Gly Val Ile Ala Asp Asn Gln Ala Lys Trp Ala Val Pro Thr Thr
            340                 345                 350

Arg Thr Asp Asp Lys Leu Arg Met Glu Thr Cys Phe Gln Gln Ala Cys
        355                 360                 365

Lys Gly Lys Ile Gln Ala Leu Cys Glu Asn Pro Glu Trp Ala Pro Leu
    370                 375                 380
```

```
Lys Asp Asn Arg Ile Pro Ser Tyr Gly Val Leu Ser Val Asp Leu Ser
385                 390                 395                 400

Leu Thr Val Glu Leu Lys Ile Lys Ile Ala Ser Gly Phe Gly Pro Leu
            405                 410                 415

Ile Thr His Gly Ser Gly Met Asp Leu Tyr Lys Ser Asn His Asn Asn
        420                 425                 430

Val Tyr Trp Leu Thr Ile Pro Pro Met Lys Asn Leu Ala Leu Gly Val
    435                 440                 445

Ile Asn Thr Leu Glu Trp Ile Pro Arg Phe Lys Val Ser Pro Ala Leu
450                 455                 460

Phe Thr Val Pro Ile Lys Glu Ala Gly Gly Asp Cys His Ala Pro Thr
465                 470                 475                 480

Tyr Leu Pro Ala Glu Val Asp Gly Asp Val Lys Leu Ser Ser Asn Leu
                485                 490                 495

Val Ile Leu Pro Gly Gln Asp Leu Gln Tyr Val Leu Ala Thr Tyr Asp
                500                 505                 510

Thr Ser Ala Val Glu His Ala Val Val Tyr Tyr Val Tyr Ser Pro Ser
            515                 520                 525

Arg Leu Ser Ser Tyr Phe Tyr Pro Phe Arg Leu Pro Ile Lys Gly Val
530                 535                 540

Pro Ile Glu Leu Gln Val Glu Cys Phe Thr Trp Asp Gln Lys Leu Trp
545                 550                 555                 560

Cys Arg His Phe Cys Val Leu Ala Asp Ser Glu Ser Gly Gly His Ile
                565                 570                 575

Thr His Ser Gly Met Val Gly Met Gly Val Ser Cys Thr Val Thr Arg
            580                 585                 590

Glu Asp Gly Thr Asn Ala Ala Gln Pro Ala Met Ala Asn Ser Asp Ser
                595                 600                 605

Glu Cys Pro Leu Ser His Asp Gly Tyr Cys Leu His Asp Gly Val Cys
            610                 615                 620

Met Tyr Ile Glu Ala Leu Asp Lys Tyr Ala Cys Asn Cys Val Val Gly
625                 630                 635                 640

Tyr Ile Gly Glu Arg Cys Gln Tyr Arg Asp Leu Lys Trp Trp Glu Leu
                645                 650                 655

Arg Ala Ala Ala Arg Gly Ser His His His His His His
            660                 665

<210> SEQ ID NO 5
<211> LENGTH: 5
<212> TYPE: PRT
<213> ORGANISM: Measles virus

<400> SEQUENCE: 5

Leu Ile Cys Cys Cys
1               5

<210> SEQ ID NO 6
<211> LENGTH: 4
<212> TYPE: PRT
<213> ORGANISM: Measles virus

<400> SEQUENCE: 6

Pro Tyr Val Leu
1

<210> SEQ ID NO 7
```

<211> LENGTH: 33
<212> TYPE: PRT
<213> ORGANISM: Measles virus

<400> SEQUENCE: 7

```
Arg Gly Arg Cys Asn Lys Lys Gly Glu Gln Val Gly Met Ser Arg Pro
1               5                   10                  15

Gly Leu Lys Pro Asp Leu Thr Gly Thr Ser Lys Ser Tyr Val Arg Ser
            20                  25                  30

Leu
```

<210> SEQ ID NO 8
<211> LENGTH: 34
<212> TYPE: PRT
<213> ORGANISM: Measles virus

<400> SEQUENCE: 8

```
Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg
```

<210> SEQ ID NO 9
<211> LENGTH: 9
<212> TYPE: PRT
<213> ORGANISM: Measles virus

<400> SEQUENCE: 9

```
Arg Gly Arg Cys Asn Lys Lys Gly Glu
1               5
```

<210> SEQ ID NO 10
<211> LENGTH: 16
<212> TYPE: PRT
<213> ORGANISM: Measles virus

<400> SEQUENCE: 10

```
Met Gly Ser Arg Ile Val Ile Asn Arg Glu His Leu Met Ile Asp Arg
1               5                   10                  15
```

<210> SEQ ID NO 11
<211> LENGTH: 15
<212> TYPE: PRT
<213> ORGANISM: Measles virus

<400> SEQUENCE: 11

```
Met Ser Arg Ile Val Ile Asn Arg Glu His Leu Met Ile Asp Arg
1               5                   10                  15
```

<210> SEQ ID NO 12
<211> LENGTH: 14
<212> TYPE: PRT
<213> ORGANISM: Measles virus

<400> SEQUENCE: 12

```
Met Ala Ala Ala Ala Asn Arg Glu His Leu Met Ile Asp Arg
1               5                   10
```

<210> SEQ ID NO 13
<211> LENGTH: 28
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 13
ccttaattaa atgggaagta ggatagtc                                            28

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctagctagca acccgatc                                                       18

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccttaattaa atggctatag tcattaacag agaac                                    35

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccttaattaa atggctgccg cagcgaacag agaacatctt atg                           43

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gctgcagggg gcgttgaaat aaaaagggag aac                                      33

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtaataaaaa gggagaataa gttggtatgt caag                                     34

<210> SEQ ID NO 19
<211> LENGTH: 34
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 19
gattcaaggt tagtcccgca ctcttcactg tccc                                    34

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cctacgatac ttccgcggtt gaacatgctg tgg                                     33

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtttacagcc caagccgcct atcgtcttac ttttatcc                                38

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctggaatagc tcagaatccg aggcatcctc ggcctctgc                               39

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccaatgcatt ggtgaactca ac                                                 22

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccttccctcg atggccggct gggccgcatt ggttccatct tcccg                        45

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
ggcccagccg gccatcgagg gaaggatggc tcaggttcag ctg        43

<210> SEQ ID NO 26
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctagactagt tagtgatggt gatggtgatg agaacctctt gcggccgcct tcagctccag    60
cttgg                                                                65

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atccctcggg tggcggaggc tcggacattg tgatgaccc          39

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttttcctttt gcggccgcag cccgttttat ttc          33

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcttggccca gccggccatg gaggtgaagc tggtg          35

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcccccgagc cacctccgcc ggatccaccg ccacctgagg agacggtgac    50

<210> SEQ ID NO 31
<211> LENGTH: 1851
<212> TYPE: DNA
<213>

<400> SEQUENCE: 31

```
atgtcaccac aacgagaccg gataaatgcc ttctacaaag ataaccccca tcccaaggga      60
agtaggatag tcattaacag agaacatctt atgattgata gaccttatgt tttgctggct     120
gttctgtttg tcatgtttct gagcttgatc gggttgctag ccattgcagg aattcgactt     180
catcgggcag ccatctacac cgcagagatc cataaaagcc tcagcaccaa tctagatgta     240
actaactcaa tcgagcatca ggtcaaggac gtgctgacac cactcttcaa aatcatcggt     300
gatgaagtgg gcctgaggac acctcagaga ttcactgacc tagtgaaatt catctctgac     360
aagattaaat tccttaatcc ggataggag tacgacttca gagatctcac ttggtgtatc      420
aacccgccag agagaatcaa attggattat gatcaatact gtgcagatgt ggctgctgaa     480
gagctcatga atgcattggt gaactcaact ctactggaga ccagaacaac caatcagttc     540
ctagctgtct caaagggaaa ctgctcaggg cccactacaa tcagaggtca attctcaaac     600
atgtcgctgt ccctgttaga cttgtattta ggtcgaggtt acaatgtgtc atctatagtc     660
actatgacat cccagggaat gtatggggga acttacctag tggaaaagcc taatctgagc     720
agcaaaaggt cagagttgtc acaactgagc atgtaccgag tgtttgaagt aggtgttatc     780
agaaatccgg gtttgggggc tccggtgttc catatgacaa actatcttga gcaaccagtc     840
agtaatgatc tcagcaactg tatggtggct ttggggagc tcaaactcgc agcccttgt      900
cacggggaag attctatcac aattccctat cagggatcag ggaaaggtgt cagcttccag     960
ctcgtcaagc taggtgtctg gaaatcccca accgacatgc aatcctgggt ccccttatca    1020
acggatgatc cagtgataga caggctttac ctctcatctc acagaggtgt tatcgctgac    1080
aaccaagcaa atgggctgt cccgacaaca cgaacagatg acaagttgcg aatggagaca    1140
tgcttccaac aggcgtgtaa gggtaaaatc caagcactct gcgagaatcc cgagtgggca    1200
ccattgaagg ataacaggat tccttcatac ggggtcttgt ctgttgatct gagtctgaca    1260
gttgagctta aaatcaaaat tgcttcggga ttcgggccat tgatcacaca cggttcaggg    1320
atggacctat acaaatccaa ccacaacaat gtgtattggc tgactatccc gccaatgaag    1380
aacctagcct taggtgtaat caacacattg gagtggatac cgagattcaa ggttagtccc    1440
tacctcttca ctgtcccaat taaggaagca ggcggagact gccatgcccc aacatacta     1500
cctgcggagg tggatggtga tgtcaaactc agttccaatc tggtgattct acctggtcaa    1560
gatctccaat atgttttggc aacctacgat acttccaggg ttgaacatgc tgtggtttat    1620
tacgtttaca gcccaagccg ctcatttttct tactttatc cttttaggtt gcctataaag    1680
ggggtcccca tcgaattaca agtggaatgc ttcacatggg accaaaaact ctggtgccgt    1740
cacttctgtg tgcttgcgga ctcagaatct ggtggacata tcactcactc tgggatggtg    1800
ggcatgggag tcagctgcac agtcacccgg gaagatggaa ccaatcgcag a             1851
```

<210> SEQ ID NO 32
<211> LENGTH: 617
<212> TYPE: PRT
<213> ORGANISM: Measles virus

<400> SEQUENCE: 32

```
Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
```

```
                35                  40                  45
Leu Ile Gly Leu Leu Ala Ile Ala Gly Ile Arg Leu His Arg Ala Ala
 50                  55                  60
Ile Tyr Thr Ala Glu Ile His Lys Ser Leu Ser Thr Asn Leu Asp Val
 65                  70                  75                  80
Thr Asn Ser Ile Glu His Gln Val Lys Asp Val Leu Thr Pro Leu Phe
                 85                  90                  95
Lys Ile Ile Gly Asp Glu Val Gly Leu Arg Thr Pro Gln Arg Phe Thr
                100                 105                 110
Asp Leu Val Lys Phe Ile Ser Asp Lys Ile Lys Phe Leu Asn Pro Asp
                115                 120                 125
Arg Glu Tyr Asp Phe Arg Asp Leu Thr Trp Cys Ile Asn Pro Pro Glu
            130                 135                 140
Arg Ile Lys Leu Asp Tyr Asp Gln Tyr Cys Ala Asp Val Ala Ala Glu
145                 150                 155                 160
Glu Leu Met Asn Ala Leu Val Asn Ser Thr Leu Leu Glu Thr Arg Thr
                165                 170                 175
Thr Asn Gln Phe Leu Ala Val Ser Lys Gly Asn Cys Ser Gly Pro Thr
                180                 185                 190
Thr Ile Arg Gly Gln Phe Ser Asn Met Ser Leu Ser Leu Leu Asp Leu
            195                 200                 205
Tyr Leu Gly Arg Gly Tyr Asn Val Ser Ser Ile Val Thr Met Thr Ser
210                 215                 220
Gln Gly Met Tyr Gly Gly Thr Tyr Leu Val Glu Lys Pro Asn Leu Ser
225                 230                 235                 240
Ser Lys Arg Ser Glu Leu Ser Gln Leu Ser Met Tyr Arg Val Phe Glu
                245                 250                 255
Val Gly Val Ile Arg Asn Pro Gly Leu Gly Ala Pro Val Phe His Met
                260                 265                 270
Thr Asn Tyr Leu Glu Gln Pro Val Ser Asn Asp Leu Ser Asn Cys Met
            275                 280                 285
Val Ala Leu Gly Glu Leu Lys Leu Ala Ala Leu Cys His Gly Glu Asp
            290                 295                 300
Ser Ile Thr Ile Pro Tyr Gln Gly Ser Gly Lys Gly Val Ser Phe Gln
305                 310                 315                 320
Leu Val Lys Leu Gly Val Trp Lys Ser Pro Thr Asp Met Gln Ser Trp
                325                 330                 335
Val Pro Leu Ser Thr Asp Asp Pro Val Ile Asp Arg Leu Tyr Leu Ser
                340                 345                 350
Ser His Arg Gly Val Ile Ala Asp Asn Gln Ala Lys Trp Ala Val Pro
            355                 360                 365
Thr Thr Arg Thr Asp Asp Lys Leu Arg Met Glu Thr Cys Phe Gln Gln
370                 375                 380
Ala Cys Lys Gly Lys Ile Gln Ala Leu Cys Glu Asn Pro Glu Trp Ala
385                 390                 395                 400
Pro Leu Lys Asp Asn Arg Ile Pro Ser Tyr Gly Val Leu Ser Val Asp
                405                 410                 415
Leu Ser Leu Thr Val Glu Leu Lys Ile Lys Ile Ala Ser Gly Phe Gly
                420                 425                 430
Pro Leu Ile Thr His Gly Ser Gly Met Asp Leu Tyr Lys Ser Asn His
            435                 440                 445
Asn Asn Val Tyr Trp Leu Thr Ile Pro Pro Met Lys Asn Leu Ala Leu
            450                 455                 460
```

```
Gly Val Ile Asn Thr Leu Glu Trp Ile Pro Arg Phe Lys Val Ser Pro
465                 470                 475                 480

Tyr Leu Phe Thr Val Pro Ile Lys Glu Ala Gly Asp Cys His Ala
                485                 490                 495

Pro Thr Tyr Leu Pro Ala Glu Val Asp Gly Asp Val Lys Leu Ser Ser
                500                 505                 510

Asn Leu Val Ile Leu Pro Gly Gln Asp Leu Gln Tyr Val Leu Ala Thr
                515                 520                 525

Tyr Asp Thr Ser Arg Val Glu His Ala Val Val Tyr Tyr Val Tyr Ser
                530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
                580                 585                 590

His Ile Thr His Ser Gly Met Val Gly Met Gly Val Ser Cys Thr Val
                595                 600                 605

Thr Arg Glu Asp Gly Thr Asn Arg Arg
    610                 615

<210> SEQ ID NO 33
<211> LENGTH: 1662
<212> TYPE: DNA
<213> ORGANISM: Measles virus

<400> SEQUENCE: 33
atgtccatca tgggtctcaa ggtgaacgtc tctgccatat tcatggcagt actgttaact      60
ctccaaacac ccaccggtca aatccattgg ggcaatctct ctaagatagg ggtggtagga    120
ataggaagtg caagctacaa agttatgact cgttccagcc atcaatcatt agtcataaaa    180
ttaatgccca atataactct cctcaataac tgcacgaggg tagagattgc agaatacagg    240
agactactga gaactgtttt ggaaccaatt agagatgcac ttaatgcaat gacccagaat    300
ataagaccgg ttcagagtgt agcttcaagt aggagacaca gagatttgc gggagtagtc    360 ctggcaggtg cggccctagg cgttgccaca gctgctcaga taacagccgg cattgcactt    420
caccagtcca tgctgaactc tcaagccatc gacaatctga gagcgagcct ggaaactact    480
aatcaggcaa ttgaggcaat cagacaagca gggcaggaga tgatattggc tgttcagggt    540
gtccaagact acatcaataa tgagctgata ccgtctatga accaactatc ttgtgattta    600
atcggccaga gctcgggct caaattgctc agatactata cagaaatcct gtcattattt    660
ggccccagct acggaccc catatctgcg gagatatcta tccaggcttt gagctatgcg    720
cttggaggag acatcaataa ggtgttagaa aagctcggat acagtggagg tgatttactg    780
ggcatcttag agagcagagg aataaaggcc cggataactc acgtcgacac agagtcctac    840
ttcattgtcc tcagtatagc ctatccgacg ctgtccgaga ttaaggggt gattgtccac    900 cggctagagg gggtctcgta caacataggc tctcaagagt ggtataccac tgtgcccaag    960
tatgtcgcaa cccaagggta ccttatctcg aattttgatg agtcatcgtg tactttcatg   1020
ccagagggaa ctgtgtgcag ccaaaatgcc ttgtacccga tgagtcctct gctccaagaa   1080
tgcctccggg ggtccactaa gtcctgtgct cgtacactcg tatccgggtc ttttgggaac   1140
cggttcattt tatcacaagg gaacctaata gccaattgtg catcaatcct ttgcaagtgt   1200
```

```
tacacaacag gaacgatcat taatcaagac cctgacaaga tcctaacata cattgctgcc   1260
gatcactgcc cggtagtcga ggtgaacggc gtgaccatcc aagtcgggag caggaggtat   1320
ccagacgctg tgtacttgca cagaattgac ctcggtcctc ccatatcatt ggagaggttg   1380
gacgtaggga caaatctggg gaatgcaatt gctaagttgg aggatgccaa ggaattgttg   1440
gagtcatcgg accagatatt gaggagtatg aaaggtttat cgagcactag catagtctac   1500
atcctgattg cagtgtgtct tggagggttg atagggatcc ccgctttaat atgttgctgc   1560
agggggcgtt gtaataaaaa gggagaacaa gttggtatgt caagaccagg cctaaagcct   1620
gatcttacgg gaacatcaaa atcctatgta aggtcgctct ga                      1662

<210> SEQ ID NO 34
<211> LENGTH: 553
<212> TYPE: PRT
<213> ORGANISM: Measles virus

<400> SEQUENCE: 34

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Trp Gly Asn
            20                  25                  30

Leu Ser Lys Ile Gly Val Val Gly Ile Gly Ser Ala Ser Tyr Lys Val
        35                  40                  45

Met Thr Arg Ser Ser His Gln Ser Leu Val Ile Lys Leu Met Pro Asn
    50                  55                  60

Ile Thr Leu Leu Asn Asn Cys Thr Arg Val Glu Ile Ala Glu Tyr Arg
65                  70                  75                  80

Arg Leu Leu Arg Thr Val Leu Glu Pro Ile Arg Asp Ala Leu Asn Ala
                85                  90                  95

Met Thr Gln Asn Ile Arg Pro Val Gln Ser Val Ala Ser Ser Arg Arg
            100                 105                 110

His Lys Arg Phe Ala Gly Val Val Leu Ala Gly Ala Ala Leu Gly Val
        115                 120                 125

Ala Thr Ala Ala Gln Ile Thr Ala Gly Ile Ala Leu His Gln Ser Met
    130                 135                 140

Leu Asn Ser Gln Ala Ile Asp Asn Leu Arg Ala Ser Leu Glu Thr Thr
145                 150                 155                 160

Asn Gln Ala Ile Glu Ala Ile Arg Gln Ala Gly Gln Glu Met Ile Leu
                165                 170                 175

Ala Val Gln Gly Val Gln Asp Tyr Ile Asn Asn Glu Leu Ile Pro Ser
            180                 185                 190

Met Asn Gln Leu Ser Cys Asp Leu Ile Gly Gln Lys Leu Gly Leu Lys
        195                 200                 205

Leu Leu Arg Tyr Tyr Thr Glu Ile Leu Ser Leu Phe Gly Pro Ser Leu
    210                 215                 220

Arg Asp Pro Ile Ser Ala Glu Ile Ser Ile Gln Ala Leu Ser Tyr Ala
225                 230                 235                 240

Leu Gly Gly Asp Ile Asn Lys Val Leu Glu Lys Leu Gly Tyr Ser Gly
                245                 250                 255

Gly Asp Leu Leu Gly Ile Leu Glu Ser Arg Gly Ile Lys Ala Arg Ile
            260                 265                 270

Thr His Val Asp Thr Glu Ser Tyr Phe Ile Val Leu Ser Ile Ala Tyr
        275                 280                 285

Pro Thr Leu Ser Glu Ile Lys Gly Val Ile Val His Arg Leu Glu Gly
```

```
                290                 295                 300
Val Ser Tyr Asn Ile Gly Ser Gln Glu Trp Tyr Thr Thr Val Pro Lys
305                 310                 315                 320

Tyr Val Ala Thr Gln Gly Tyr Leu Ile Ser Asn Phe Asp Glu Ser Ser
                325                 330                 335

Cys Thr Phe Met Pro Glu Gly Thr Val Cys Ser Gln Asn Ala Leu Tyr
                340                 345                 350

Pro Met Ser Pro Leu Leu Gln Glu Cys Leu Arg Gly Ser Thr Lys Ser
            355                 360                 365

Cys Ala Arg Thr Leu Val Ser Gly Ser Phe Gly Asn Arg Phe Ile Leu
            370                 375                 380

Ser Gln Gly Asn Leu Ile Ala Asn Cys Ala Ser Ile Leu Cys Lys Cys
385                 390                 395                 400

Tyr Thr Thr Gly Thr Ile Ile Asn Gln Asp Pro Asp Lys Ile Leu Thr
                405                 410                 415

Tyr Ile Ala Ala Asp His Cys Pro Val Val Glu Val Asn Gly Val Thr
            420                 425                 430

Ile Gln Val Gly Ser Arg Arg Tyr Pro Asp Ala Val Tyr Leu His Arg
            435                 440                 445

Ile Asp Leu Gly Pro Pro Ile Ser Leu Glu Arg Leu Asp Val Gly Thr
        450                 455                 460

Asn Leu Gly Asn Ala Ile Ala Lys Leu Glu Asp Ala Lys Glu Leu Leu
465                 470                 475                 480

Glu Ser Ser Asp Gln Ile Leu Arg Ser Met Lys Gly Leu Ser Ser Thr
                485                 490                 495

Ser Ile Val Tyr Ile Leu Ile Ala Val Cys Leu Gly Gly Leu Ile Gly
            500                 505                 510

Ile Pro Ala Leu Ile Cys Cys Cys Arg Gly Arg Cys Asn Lys Lys Gly
            515                 520                 525

Glu Gln Val Gly Met Ser Arg Pro Gly Leu Lys Pro Asp Leu Thr Gly
            530                 535                 540

Thr Ser Lys Ser Tyr Val Arg Ser Leu
545                 550

<210> SEQ ID NO 35
<211> LENGTH: 1797
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atgggaagta ggatagtcat taacagagaa catcttatga ttgatagacc ttatgttttg     60
ctggctgttc tgtttgtcat gtttctgagc ttgatcgggt tgctagccat tgcaggaatt    120
cgacttcatc gggcagccat ctacaccgca gagatccata aaagcctcag caccaatcta    180
gatgtaacta actcaatcga gcatcaggtc aaggacgtgc tgacaccact cttcaaaatc    240
atcggtgatg aagtgggcct gaggacacct cagagattca ctgacctagt gaaattcatc    300
tctgacaaga ttaaattcct taatccggat agggagtacg acttcagaga tctcacttgg    360
tgtatcaacc cgccagagag aatcaaattg gattatgatc aatactgtgc agatgtggct    420
gctgaagagc tcatgaatgc attggtgaac tcaactctac tggagaccag aacaaccaat    480
cagttcctag ctgtctcaaa gggaaactgc tcagggccca ctacaatcag aggtcaattc    540
```

```
tcaaacatgt cgctgtccct gttagacttg tatttaggtc gaggttacaa tgtgtcatct    600
atagtcacta tgacatccca gggaatgtat gggggaactt acctagtgga aaagcctaat    660
ctgagcagca aaaggtcaga gttgtcacaa ctgagcatgt accgagtgtt tgaagtaggt    720
gttatcagaa atccgggttt gggggctccg gtgttccata tgacaaacta tcttgagcaa    780
ccagtcagta atgatctcag caactgtatg gtggctttgg gggagctcaa actcgcagcc    840
ctttgtcacg gggaagattc tatcacaatt ccctatcagg gatcagggaa aggtgtcagc    900
ttccagctcg tcaagctagg tgtctggaaa tccccaaccg acatgcaatc ctgggtcccc    960
ttatcaacgg atgatccagt gatagacagg ctttacctct catctcacag aggtgttatc   1020
gctgacaacc aagcaaaatg ggctgtcccg acaacacgaa cagatgacaa gttgcgaatg   1080
gagacatgct ccaacaggc gtgtaagggt aaaatccaag cactctgcga gaatcccgag   1140
tgggcaccat tgaaggataa caggattcct tcatacgggg tcttgtctgt tgatctgagt   1200
ctgacagttg agcttaaaat caaaattgct tcgggattcg ggccattgat cacacacggt   1260
tcagggatgg acctatacaa atccaaccac aacaatgtgt attggctgac tatcccgcca   1320
atgaagaacc tagccttagg tgtaatcaac acattggagt ggataccgag attcaaggtt   1380
agtccctacc tcttcactgt cccaattaag gaagcaggcg gagactgcca tgccccaaca   1440
tacctacctg cggaggtgga tggtgatgtc aaactcagtt ccaatctggt gattctacct   1500
ggtcaagatc tccaatatgt tttggcaacc tacgatactt ccagggttga acatgctgtg   1560
gtttattacg tttacagccc aagccgctca ttttcttact tttatccttt taggttgcct   1620 ataaagggg tccccatcga attacaagtg gaatgcttca catgggacca aaaactctgg   1680
tgccgtcact tctgtgtgct tgcggactca gaatctggtg acatatcac tcactctggg   1740 atggtgggca tgggagtcag ctgcacagtc acccgggaag atggaaccaa tcgcaga     1797
```

<210> SEQ ID NO 36
<211> LENGTH: 1794
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
atgagtagga tagtcattaa cagagaacat cttatgattg atagacctta tgttttgctg     60
gctgttctgt ttgtcatgtt tctgagcttg atcgggttgc tagccattgc aggaattcga    120
cttcatcggg cagccatcta caccgcagag atccataaaa gcctcagcac caatctagat    180
gtaactaact caatcgagca tcaggtcaag gacgtgctga caccactctt caaaatcatc    240
ggtgatgaag tgggcctgag acacctcag agattcactg acctagtgaa attcatctct    300
gacaagatta aattccttaa tccggatagg gagtacgact tcagagatct cacttggtgt    360
atcaacccgc cagagagaat caaattggat tatgatcaat actgtgcaga gtgggctgct    420
gaagagctca tgaatgcatt ggtgaactca actctactgg agaccagaac aaccaatcag    480
ttcctagctg tctcaaaggg aaactgctca gggcccacta caatcagagg tcaattctca    540
aacatgtcgc tgtccctgtt agacttgtat ttaggtcgag ttacaatgt gtcatctata    600 gtcactatga catcccaggg aatgtatggg ggaacttacc tagtggaaaa gcctaatctg    660
agcagcaaaa ggtcagagtt gtcacaactg agcatgtacc gagtgtttga gtaggtgtt    720 atcagaaatc cgggtttggg ggctccggtg ttccatatga caaactatct tgagcaacca    780
```

```
gtcagtaatg atctcagcaa ctgtatggtg gctttggggg agctcaaact cgcagcccTT    840
tgtcacgggg aagattctat cacaattccc tatcagggat cagggaaagg tgtcagcttc    900
cagctcgtca agctaggtgt ctggaaatcc ccaaccgaca tgcaatcctg ggtcccctta    960
tcaacggatg atccagtgat agacaggctt tacctctcat ctcacagagg tgttatcgct   1020
gacaaccaag caaaatgggc tgtcccgaca acacgaacag atgacaagtt gcgaatggag   1080
acatgcttcc aacaggcgtg taagggtaaa atccaagcac tctgcgagaa tcccgagtgg   1140
gcaccattga aggataacag gattccttca tacgggtct tgtctgttga tctgagtctg    1200
acagttgagc ttaaaatcaa aattgcttcg ggattcgggc cattgatcac acacggttca   1260
gggatggacc tatacaaatc caaccacaac aatgtgtatt ggctgactat cccgccaatg   1320
aagaacctag ccttaggtgt aatcaacaca ttggagtgga taccgagatt caaggttagt   1380
ccctacctct tcactgtccc aattaaggaa gcaggcggag actgccatgc cccaacatac   1440
ctacctgcgg aggtggatgg tgatgtcaaa ctcagttcca atctggtgat tctacctggt   1500
caagatctcc aatatgtttt ggcaacctac gatacttcca gggttgaaca tgctgtggtt   1560
tattacgttt acagcccaag ccgctcattt tcttactttt atccttttag gttgcctata   1620
aaggggtcc  ccatcgaatt acaagtggaa tgcttcacat gggaccaaaa actctggtgc   1680
cgtcacttct gtgtgcttgc ggactcagaa tctggtggac atatcactca ctctgggatg   1740
gtgggcatgg gagtcagctg cacagtcacc cgggaagatg gaaccaatcg caga         1794
```

<210> SEQ ID NO 37
<211> LENGTH: 1791
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
atggctgccg cagcgaacag agaacatctt atgattgata gaccttatgt tttgctggct     60
gttctgtttg tcatgtttct gagcttgatc gggttgctag ccattgcagg aattcgactt    120
catcgggcag ccatctacac cgcagagatc cataaaagcc tcagcaccaa tctagatgta    180
actaactcaa tcgagcatca ggtcaaggac gtgctgacac cactcttcaa aatcatcggt    240
gatgaagtgg gcctgaggac acctcagaga ttcactgacc tagtgaaatt catctctgac    300
aagattaaat tccttaatcc ggatagggag tacgacttca gagatctcac ttggtgtatc    360
aacccgccag agagaatcaa attggattat gatcaatact gtgcagatgt ggctgctgaa    420
gagctcatga atgcattggt gaactcaact ctactggaga ccagaacaac caatcagttc    480
ctagctgtct caagggaaa ctgctcaggg cccactacaa tcagaggtca attctcaaac     540
atgtcgctgt ccctgttaga cttgtattta ggtcgaggtt acaatgtgtc atctatagtc    600
actatgacat cccagggaat gtatggggga acttacctag tggaaaagcc taatctgagc    660
agcaaaaggt cagagttgtc acaactgagc atgtaccgag tgtttgaagt aggtgttatc    720
agaaatccgg gtttgggggc tccggtgttc catatgacaa actatcttga gcaaccagtc    780
agtaatgatc tcagcaactg tatggtggct ttggggagc tcaaactcgc agcccttgt     840
cacggggaag attctatcac aattccctat cagggatcag ggaaggtgt cagcttccag     900
ctcgtcaagc taggtgtctg gaaatcccca accgacatgc aatcctgggt ccccttatca    960
acggatgatc cagtgataga caggctttac ctctcatctc acagaggtgt tatcgctgac   1020
```

```
aaccaagcaa aatgggctgt cccgacaaca cgaacagatg acaagttgcg aatggagaca   1080
tgcttccaac aggcgtgtaa gggtaaaatc caagcactct gcgagaatcc cgagtgggca   1140
ccattgaagg ataacaggat tccttcatac ggggtcttgt ctgttgatct gagtctgaca   1200
gttgagctta aaatcaaaat tgcttcggga ttcgggccat tgatcacaca cggttcaggg   1260
atggacctat acaaatccaa ccacaacaat gtgtattggc tgactatccc gccaatgaag   1320
aacctagcct taggtgtaat caacacattg gagtggatac cgagattcaa ggttagtccc   1380
tacctcttca ctgtcccaat taaggaagca ggcggagact gccatgcccc aacataccta   1440
cctgcggagg tggatggtga tgtcaaactc agttccaatc tggtgattct acctggtcaa   1500
gatctccaat atgttttggc aacctacgat acttccaggg ttgaacatgc tgtggtttat   1560
tacgtttaca gcccaagccg ctcattttct tactttatc cttttaggtt gcctataaag   1620
ggggtcccca tcgaattaca agtggaatgc ttcacatggg accaaaaact ctggtgccgt   1680
cacttctgtg tgcttgcgga ctcagaatct ggtggacata tcactcactc tgggatggtg   1740
ggcatgggag tcagctgcac agtcacccgg aagatggaa ccaatcgcag a           1791
```

<210> SEQ ID NO 38
<211> LENGTH: 599
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Met Gly Ser Arg Ile Val Ile Asn Arg Glu His Leu Met Ile Asp Arg
1               5                   10                  15

Pro Tyr Val Leu Leu Ala Val Leu Phe Val Met Phe Leu Ser Leu Ile
            20                  25                  30

Gly Leu Leu Ala Ile Ala Gly Ile Arg Leu His Arg Ala Ala Ile Tyr
        35                  40                  45

Thr Ala Glu Ile His Lys Ser Leu Ser Thr Asn Leu Asp Val Thr Asn
    50                  55                  60

Ser Ile Glu His Gln Val Lys Asp Val Leu Thr Pro Leu Phe Lys Ile
65                  70                  75                  80

Ile Gly Asp Glu Val Gly Leu Arg Thr Pro Gln Arg Phe Thr Asp Leu
                85                  90                  95

Val Lys Phe Ile Ser Asp Lys Ile Lys Phe Leu Asn Pro Asp Arg Glu
            100                 105                 110

Tyr Asp Phe Arg Asp Leu Thr Trp Cys Ile Asn Pro Pro Glu Arg Ile
        115                 120                 125

Lys Leu Asp Tyr Asp Gln Tyr Cys Ala Asp Val Ala Ala Glu Glu Leu
    130                 135                 140

Met Asn Ala Leu Val Asn Ser Thr Leu Leu Glu Thr Arg Thr Thr Asn
145                 150                 155                 160

Gln Phe Leu Ala Val Ser Lys Gly Asn Cys Ser Gly Pro Thr Thr Ile
                165                 170                 175

Arg Gly Gln Phe Ser Asn Met Ser Leu Ser Leu Leu Asp Leu Tyr Leu
            180                 185                 190

Gly Arg Gly Tyr Asn Val Ser Ser Ile Val Thr Met Thr Ser Gln Gly
        195                 200                 205

Met Tyr Gly Gly Thr Tyr Leu Val Glu Lys Pro Asn Leu Ser Ser Lys
    210                 215                 220
```

```
Arg Ser Glu Leu Ser Gln Leu Ser Met Tyr Arg Val Phe Glu Val Gly
225                 230                 235                 240

Val Ile Arg Asn Pro Gly Leu Gly Ala Pro Val Phe His Met Thr Asn
            245                 250                 255

Tyr Leu Glu Gln Pro Val Ser Asn Asp Leu Ser Asn Cys Met Val Ala
        260                 265                 270

Leu Gly Glu Leu Lys Leu Ala Ala Leu Cys His Gly Glu Asp Ser Ile
    275                 280                 285

Thr Ile Pro Tyr Gln Gly Ser Gly Lys Gly Val Ser Phe Gln Leu Val
290                 295                 300

Lys Leu Gly Val Trp Lys Ser Pro Thr Asp Met Gln Ser Trp Val Pro
305                 310                 315                 320

Leu Ser Thr Asp Asp Pro Val Ile Asp Arg Leu Tyr Leu Ser Ser His
            325                 330                 335

Arg Gly Val Ile Ala Asp Asn Gln Ala Lys Trp Ala Val Pro Thr Thr
        340                 345                 350

Arg Thr Asp Asp Lys Leu Arg Met Glu Thr Cys Phe Gln Gln Ala Cys
    355                 360                 365

Lys Gly Lys Ile Gln Ala Leu Cys Glu Asn Pro Glu Trp Ala Pro Leu
370                 375                 380

Lys Asp Asn Arg Ile Pro Ser Tyr Gly Val Leu Ser Val Asp Leu Ser
385                 390                 395                 400

Leu Thr Val Glu Leu Lys Ile Lys Ile Ala Ser Gly Phe Gly Pro Leu
            405                 410                 415

Ile Thr His Gly Ser Gly Met Asp Leu Tyr Lys Ser Asn His Asn Asn
        420                 425                 430

Val Tyr Trp Leu Thr Ile Pro Pro Met Lys Asn Leu Ala Leu Gly Val
    435                 440                 445

Ile Asn Thr Leu Glu Trp Ile Pro Arg Phe Lys Val Ser Pro Tyr Leu
450                 455                 460

Phe Thr Val Pro Ile Lys Glu Ala Gly Gly Asp Cys His Ala Pro Thr
465                 470                 475                 480

Tyr Leu Pro Ala Glu Val Asp Gly Asp Val Lys Leu Ser Ser Asn Leu
            485                 490                 495

Val Ile Leu Pro Gly Gln Asp Leu Gln Tyr Val Leu Ala Thr Tyr Asp
        500                 505                 510

Thr Ser Arg Val Glu His Ala Val Tyr Tyr Val Tyr Ser Pro Ser
    515                 520                 525

Arg Ser Phe Ser Tyr Phe Tyr Pro Phe Arg Leu Pro Ile Lys Gly Val
530                 535                 540

Pro Ile Glu Leu Gln Val Glu Cys Phe Thr Trp Asp Gln Lys Leu Trp
545                 550                 555                 560

Cys Arg His Phe Cys Val Leu Ala Asp Ser Glu Ser Gly Gly His Ile
            565                 570                 575

Thr His Ser Gly Met Val Gly Met Gly Val Ser Cys Thr Val Thr Arg
        580                 585                 590

Glu Asp Gly Thr Asn Arg Arg
        595

<210> SEQ ID NO 39
<211> LENGTH: 1572
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 39

```
atgtccatca tgggtctcaa ggtgaacgtc tctgccatat tcatggcagt actgttaact      60
ctccaaacac ccaccggtca aatccattgg ggcaatctct ctaagatagg ggtggtagga     120
ataggaagtg caagctacaa agttatgact cgttccagcc atcaatcatt agtcataaaa     180
ttaatgccca atataactct cctcaataac tgcacgaggg tagagattgc agaatacagg     240
agactactga gaactgtttt ggaaccaatt agagatgcac ttaatgcaat gacccagaat     300
ataagaccgg ttcagagtgt agcttcaagt aggagacaca agagatttgc gggagtagtc     360
ctggcaggtg cggccctagg cgttgccaca gctgctcaga taacagccgg cattgcactt     420
caccagtcca tgctgaactc tcaagccatc gacaatctga gagcgagcct ggaaactact     480
aatcaggcaa ttgaggcaat cagacaagca gggcaggaga tgatattggc tgttcagggt     540
gtccaagact acatcaataa tgagctgata ccgtctatga accaactatc ttgtgattta     600
atcggccaga agctcgggct caaattgctc agatactata cagaaatcct gtcattattt     660
ggccccagct tacgggaccc catatctgcg gagatatcta tccaggcttt gagctatgcg     720
cttggaggag acatcaataa ggtgttagaa aagctcggat acagtggagg tgatttactg     780
ggcatcttag agagcagagg aataaaggcc cggataactc acgtcgacac agagtcctac     840
ttcattgtcc tcagtatagc ctatccgacg ctgtccgaga ttaaggggt gattgtccac     900
cggctagagg ggtctcgta caacataggc tctcaagagt ggtataccac tgtgcccaag     960
tatgtcgcaa cccaagggta ccttatctcg aattttgatg agtcatcgtg tactttcatg    1020
ccagagggaa ctgtgtgcag ccaaaatgcc ttgtacccga tgagtcctct gctccaagaa    1080
tgcctccggg ggtccactaa gtcctgtgct cgtacactcg tatccgggtc ttttgggaac    1140
cggttcattt tatcacaagg gaacctaata gccaattgtg catcaatcct ttgcaagtgt    1200
tacacaacag gaacgatcat taatcaagac cctgacaaga tcctaacata cattgctgcc    1260
gatcactgcc cggtagtcga ggtgaacggc gtgaccatcc aagtcgggag caggaggtat    1320
ccagacgctg tgtacttgca cagaattgac ctcggtcctc ccatatcatt ggagaggttg    1380
gacgtaggga caaatctggg gaatgcaatt gctaagttgg aggatgccaa ggaattgttg    1440
gagtcatcgg accagatatt gaggagtatg aaaggtttat cgagcactag catagtctac    1500
atcctgattg cagtgtgtct tggagggttg atagggatcc ccgctttaat atgttgctgc    1560
aggggggcgtt ga                                                        1572
```

<210> SEQ ID NO 40
<211> LENGTH: 523
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Trp Gly Asn
            20                  25                  30

Leu Ser Lys Ile Gly Val Val Gly Ile Gly Ser Ala Ser Tyr Lys Val
        35                  40                  45

Met Thr Arg Ser Ser His Gln Ser Leu Val Ile Lys Leu Met Pro Asn

-continued

```
            50                  55                  60
Ile Thr Leu Leu Asn Asn Cys Thr Arg Val Glu Ile Ala Glu Tyr Arg
 65                  70                  75                  80

Arg Leu Leu Arg Thr Val Leu Glu Pro Ile Arg Asp Ala Leu Asn Ala
                 85                  90                  95

Met Thr Gln Asn Ile Arg Pro Val Gln Ser Val Ala Ser Ser Arg Arg
            100                 105                 110

His Lys Arg Phe Ala Gly Val Val Leu Ala Gly Ala Ala Leu Gly Val
            115                 120                 125

Ala Thr Ala Ala Gln Ile Thr Ala Gly Ile Ala Leu His Gln Ser Met
130                 135                 140

Leu Asn Ser Gln Ala Ile Asp Asn Leu Arg Ala Ser Leu Glu Thr Thr
145                 150                 155                 160

Asn Gln Ala Ile Glu Ala Ile Arg Gln Ala Gly Gln Glu Met Ile Leu
                165                 170                 175

Ala Val Gln Gly Val Gln Asp Tyr Ile Asn Asn Glu Leu Ile Pro Ser
            180                 185                 190

Met Asn Gln Leu Ser Cys Asp Leu Ile Gly Gln Lys Leu Gly Leu Lys
            195                 200                 205

Leu Leu Arg Tyr Tyr Thr Glu Ile Leu Ser Leu Phe Gly Pro Ser Leu
210                 215                 220

Arg Asp Pro Ile Ser Ala Glu Ile Ser Ile Gln Ala Leu Ser Tyr Ala
225                 230                 235                 240

Leu Gly Gly Asp Ile Asn Lys Val Leu Glu Lys Leu Gly Tyr Ser Gly
                245                 250                 255

Gly Asp Leu Leu Gly Ile Leu Glu Ser Arg Gly Ile Lys Ala Arg Ile
            260                 265                 270

Thr His Val Asp Thr Glu Ser Tyr Phe Ile Val Leu Ser Ile Ala Tyr
            275                 280                 285

Pro Thr Leu Ser Glu Ile Lys Gly Val Ile Val His Arg Leu Glu Gly
290                 295                 300

Val Ser Tyr Asn Ile Gly Ser Gln Glu Trp Tyr Thr Thr Val Pro Lys
305                 310                 315                 320

Tyr Val Ala Thr Gln Gly Tyr Leu Ile Ser Asn Phe Asp Glu Ser Ser
                325                 330                 335

Cys Thr Phe Met Pro Glu Gly Thr Val Cys Ser Gln Asn Ala Leu Tyr
            340                 345                 350

Pro Met Ser Pro Leu Leu Gln Glu Cys Leu Arg Gly Ser Thr Lys Ser
            355                 360                 365

Cys Ala Arg Thr Leu Val Ser Gly Ser Phe Gly Asn Arg Phe Ile Leu
370                 375                 380

Ser Gln Gly Asn Leu Ile Ala Asn Cys Ala Ser Ile Leu Cys Lys Cys
385                 390                 395                 400

Tyr Thr Thr Gly Thr Ile Ile Asn Gln Asp Pro Asp Lys Ile Leu Thr
                405                 410                 415

Tyr Ile Ala Ala Asp His Cys Pro Val Val Glu Val Asn Gly Val Thr
            420                 425                 430

Ile Gln Val Gly Ser Arg Arg Tyr Pro Asp Ala Val Tyr Leu His Arg
            435                 440                 445

Ile Asp Leu Gly Pro Pro Ile Ser Leu Glu Arg Leu Asp Val Gly Thr
450                 455                 460

Asn Leu Gly Asn Ala Ile Ala Lys Leu Glu Asp Ala Lys Glu Leu Leu
465                 470                 475                 480
```

```
Glu Ser Ser Asp Gln Ile Leu Arg Ser Met Lys Gly Leu Ser Ser Thr
            485                 490                 495

Ser Ile Val Tyr Ile Leu Ile Ala Val Cys Leu Gly Gly Leu Ile Gly
        500                 505                 510

Ile Pro Ala Leu Ile Cys Cys Cys Arg Gly Arg
        515                 520
```

<210> SEQ ID NO 41
<211> LENGTH: 1791
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
atggctgccg cagcgaacag agaacatctt atgattgata gaccttatgt tttgctggct    60
gttctgtttg tcatgtttct gagcttgatc gggttgctag ccattgcagg aattcgactt   120
catcgggcag ccatctacac cgcagagatc cataaaagcc tcagcaccaa tctagatgta   180
actaactcaa tcgagcatca ggtcaaggac gtgctgacac cactcttcaa aatcatcggt   240
gatgaagtgg gcctgaggac acctcagaga ttcactgacc tagtgaaatt catctctgac   300
aagattaaat tccttaatcc ggatagggag tacgacttca gagatctcac ttggtgtatc   360
aacccgccag agagaatcaa attggattat gatcaatact gtgcagatgt ggctgctgaa   420
gagctcatga atgcattggt gaactcaact ctactggaga ccagaacaac caatcagttc   480
ctagctgtct caaagggaaa ctgctcaggg cccactacaa tcagaggtca attctcaaac   540
atgtcgctgt ccctgttaga cttgtattta ggtcgaggtt acaatgtgtc atctatagtc   600
actatgacat cccagggaat gtatggggga acttacctag tggaaaagcc taatctgagc   660
agcaaaaggt cagagttgtc acaactgagc atgtaccgag tgtttgaagt aggtgttatc   720
agaaatccgg gtttgggggc tccggtgttc catatgacaa actatcttga gcaaccagtc   780
agtaatgatc tcagcaactg tatggtggct ttggggagc tcaaactcgc agcccttttgt   840
cacggggaag attctatcac aattccctat cagggatcag ggaaaggtgt cagcttccag   900
ctcgtcaagc taggtgtctg gaaatcccca accgacatgc aatcctgggt ccccttatca   960
acggatgatc cagtgataga caggctttac ctctcatctc acagaggtgt tatcgctgac  1020
aaccaagcaa atgggctgt cccgacaaca cgaacagatg acaagttgcg aatggagaca  1080
tgcttccaac aggcgtgtaa gggtaaaatc caagcactct gcgagaatcc cgagtgggca  1140
ccattgaagg ataacaggat tccttcatac ggggtcttgt ctgttgatct gagtctgaca  1200
gttgagctta aaatcaaaat tgcttcggga ttcgggccat tgatcacaca cggttcaggg  1260
atggacctat acaaatccaa ccacaacaat gtgtattggc tgactatccc gccaatgaag  1320
aacctagcct taggtgtaat caacacattg gagtggatac cgagattcaa ggttagtccc  1380
tacctcttca ctgtcccaat taaggaagca ggcggagact gccatgcccc aacataccta  1440
cctgcggagg tggatggtga tgtcaaactc agttccaatc tggtgattct acctggtcaa  1500
gatctccaat atgtttttggc aacctacgat acttccaggg ttgaacatgc tgtggtttat  1560
tacgtttaca gcccaagccg ctcatttttct tactttatc ctttaggtt gcctataaag  1620
ggggtcccca tcgaattaca agtggaatgc ttcacatggg accaaaaact ctggtgccgt  1680
cacttctgtg tgcttgcgga ctcagaatct ggtggacata tcactcactc tgggatggtg  1740
```

```
ggcatgggag tcagctgcac agtcacccgg gaagatggaa ccaatcgcag a            1791
```

<210> SEQ ID NO 42
<211> LENGTH: 38
<212> TYPE: PRT
<213> ORGANISM: Measles virus

<400> SEQUENCE: 42

```
Leu Ile Cys Cys Cys Arg Gly Arg Cys Asn Lys Lys Gly Glu Gln Val
1               5                   10                  15

Gly Met Ser Arg Pro Gly Leu Lys Pro Asp Leu Thr Gly Thr Ser Lys
            20                  25                  30

Ser Tyr Val Arg Ser Leu
        35
```

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Leu Ile Cys Cys Cys Arg Gly Arg
1               5
```

<210> SEQ ID NO 44
<211> LENGTH: 38
<212> TYPE: PRT
<213> ORGANISM: Measles virus

<400> SEQUENCE: 44

```
Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu
        35
```

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Met Gly Ser Arg Ile Val Ile Asn Arg Glu His Leu Met Ile Asp Arg
1               5                   10                  15

Pro Tyr Val Leu
            20
```

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Met Ser Arg Ile Val Ile Asn Arg Glu His Leu Met Ile Asp Arg Pro
```

```
1               5                  10                 15

Tyr Val Leu

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Met Ala Ala Ala Ala Asn Arg Glu His Leu Met Ile Asp Arg Pro Tyr
1               5                  10                 15

Val Leu

<210> SEQ ID NO 48
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
ggcccagccg gccatggcca atagtgactc tgaatgtccc ctgtcccacg atgggtactg     60
cctccatgat ggtgtgtgca tgtatattga agcattggac aagtatgcat gcaactgtgt    120
tgttggctac atcggggagc gatgtcagta ccgagacctg aagtggtggg aactgcgcgc    180
ggccgc                                                               186

<210> SEQ ID NO 49
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ala Gln Pro Ala Met Ala Asn Ser Asp Ser Glu Cys Pro Leu Ser His
1               5                  10                 15

Asp Gly Tyr Cys Leu His Asp Gly Val Cys Met Tyr Ile Glu Ala Leu
                20                  25                 30

Asp Lys Tyr Ala Cys Asn Cys Val Val Gly Tyr Ile Gly Glu Arg Cys
            35                  40                 45

Gln Tyr Arg Asp Leu Lys Trp Trp Glu Leu Arg Ala Ala Ala
        50                  55                 60
```

PSEUDOTYPING OF RETROVIRAL VECTORS, METHODS FOR PRODUCTION AND USE THEREOF FOR TARGETED GENE TRANSFER AND HIGH THROUGHPUT SCREENING

CROSS-REFERENCE TO RELATED PATENT APPLICATIONS

This patent application is a Continuation of copending U.S. application Ser. No. 12/443,153, filed Mar. 29, 2010, which is a 35 U.S.C. § 371 National Stage application of international patent application no. PCT/EP2007/008384, filed Sep. 26, 2007, which claims the benefit of European Patent Application No. 06020257.9, filed Sep. 27, 2006. The disclosures set forth in the referenced applications are incorporated herein by reference in their entireties.

SEQUENCE LISTING

The instant application contains a Sequence Listing which has been submitted in ASCII format via EFS-Web. Said ASCII copy, created on Nov. 12, 2012, is named 109157_SEQ_Amended.txt and is 66,681 bytes in size.

FIELD OF THE INVENTION

The invention relates to the pseudotyping of retroviral vectors with heterologous envelope proteins derived from the Paramyxoviridae family, genus *Morbillivirus*, and various uses of the resulting vector particles.

BACKGROUND OF THE INVENTION

Compared to other gene transfer systems, retroviral vectors offer a wide range of advantages, including their ability to transduce a variety of cell types, to stably integrate transferred genetic material into the genome of the targeted host cell, and to express the transduced gene at significantly levels. Therefore, vectors derived from the gamma-retroviruses, for example, the murine leukemia virus (MLV), have become a standard tool for gene transfer technology and have been frequently used in clinical gene therapy trials (Ross et al., Hum. Gen Ther. 7:1781-1790, 1996). Furthermore, the use of these vectors for the treatment of different monogenetic immunodeficiencies has also been previously described.

Pseudotyping of retroviral vectors, including HIV vectors or MLV vectors, refers to the incorporation of envelope proteins from heterologous viruses into the retroviral envelope membrane. Such pseudotyped retroviral vectors then exhibit a receptor phenotype similar to the virus from which the envelope protein was derived. Depending on the host range of said virus, the pseudotyped retroviral vectors will then have a broadened or a narrowed host range as compared to vector particles having the incorporated homologous retroviral envelope proteins.

A number of pseudotyped vectors have been described, including MLV vectors pseudotyped with the HIV Env protein, the Ebola virus glycoprotein, or the baculovirus glycoprotein. In all of these known vectors a single envelope protein was utilized to achieve the desired pseudotyping.

The measles virus (MeV), a prototype *morbillivirus* of the genus *Paramyxoviridae*, utilizes two envelope glycoproteins (the fusion protein (F) and the hemagglutinin protein (H)) to gain entry into the target cell. Protein F is a type I transmembrane protein, while protein H is a type II transmembrane domain, i.e. its amino-terminus is exposed directly to the cytoplasmic region. Both proteins thus comprise a transmembrane and a cytoplasmic region. One known function of the F protein is mediating the fusion of viral membranes with the cellular membranes of the host cell. Functions attributed to the H protein include recognizing the receptor on the target membrane and supporting F protein in its membrane fusion function. The direct and highly efficient membrane fusion at the cellular surface membrane is a particular property of measles virus and the *morbilliviruses*, thus distinguishing themselves from many other enveloped viruses that become endocytosed and will only fuse upon pH drop upon endocytosis. Both proteins are organized on the viral surface in a regular array of tightly packed spikes, H tetramers, and F trimers (Russell et al., Virology 199:160-168, 1994).

The Edmonton strain of MeV (MeV$_{Edm}$) uses a single protein as its main receptor, namely, the protein known to be the regulator of complement activation factor, CD46 (Gerlier et al., Trends Microbiol. 3:338-345, 1995). CD46 is expressed on all nucleated human cells. Most clinical isolates of measles virus, however, can not effectively use CD46 as a receptor. Human SLAM (signaling lymphocyte-activation molecule; also known as CDw150) is a recently discovered membrane glycoprotein that is expressed on some T and B cells, and was also found to act as a cellular receptor for MeV, including the Edmonston strain (Tatsuo et al., Nature 406(6798):893-7, 2000).

The precise biological functions and interactions of the MeV H and F proteins remain largely unclear. However, in experiments where truncated F and H proteins were incorporated into recombinantly produced MeV vector particles (rMeV), Moll et al. (J. Virol. 76:7174-7186, 2002) concluded that rMeV containing the truncated F protein did not reveal any difference with wild type MeV (wt MeV) with respect to the induction of syncytium formation or in infectious-virus production. The rMeV containing the truncated H protein, however, exhibited a severely reduced induction of syncytium formation and a decrease in infectious-virus production. Thus, truncation of the F and H proteins differentially resulted in a decrease of titers or no effect at all.

In view of the importance of pseudotyped retroviral vectors for numerous gene transfer technology and clinical applications, there is still a great need for additional and improved pseudotyped retroviral vectors and methods for generating and using such vectors.

SUMMARY OF THE INVENTION

The present invention is based on the surprising finding that using a combination of truncated *morbillivirus* H and F proteins in order to generate the pseudotyped lentiviral vector particles results in a significant increase in the titers and transduction efficiency of the resulting viral vector particles. Furthermore and unexpectedly, an increased amount of truncated F protein compared to the truncated H protein within the generated lentiviral vector particles leads to both an increased titer and an enhanced transduction efficiency of said lentiviral vector particles.

In one embodiment, the invention is directed to a pseudotyped lentiviral vector particle comprising a fusion (F) and a hemagglutinin (H) protein of a *morbillivirus*, wherein the cytoplasmic portions of said F and H proteins are truncated and wherein the truncated cytoplasmic portion of the F protein comprises at least 1 positively charged amino acid residue and the truncated cytoplasmic portion of the H protein is truncated to allow efficient pseudotyping and has fusion support function.

In a further embodiment, the pseudotyped lentiviral vector particle of the invention comprises a truncated H protein that is a chimeric protein which does not interact with CD46 or SLAM and further has a single chain antibody, a growth factor or a ligand to a cell surface marker at its ectodomain.

In a further embodiment, the pseudotyped lentiviral vector particle of the present invention comprises an amount of truncated F protein that is higher than the amount of truncated H protein present in said pseudotyped lentiviral vector particle. Preferably, the amount of truncated F protein is 10-100% higher, is 100-250% higher, is 250-500% higher, is 500-750% higher, is 750-1000% higher, is more than 1000% higher and even more preferably is 700% higher than the amount of truncated H protein.

In a further embodiment the invention is directed to a pharmaceutical composition comprising the lentiviral vector particles of the invention.

In even a further embodiment the invention is directed to the use of the pseudotyped lentiviral vector particle according to the present invention for the preparation of a medicament. A further embodiment of the invention is the use of the pseudotyped lentiviral particles of the invention for the preparation of a medicament for the treatment or prevention of at least one condition in a subject, wherein the condition is selected from the group consisting of a chronicle infection, an inherited monogenetic disease, a cardiovascular disease, a neurodegenerative disease, cancer, HIV, Alzheimer disease, Parkinson disease, diabetes, a neuroinflammatory disease, a rheumatic disease, an autoimmune disease, adipositas, acute lymphoblastic leukemia, myeloid leukemia, renal carcinoma, and disorders related to endothelialization or re-endothelialization.

Another embodiment of the invention is a nucleic acid molecule defined by the nucleic acid sequence set forth in SEQ ID NO: 1 or SEQ ID NO: 3. Preferably, said nucleic acid molecule is comprised by a plasmid or expression plasmid.

In a further embodiment the invention is directed to a method for producing a pseudotyped lentiviral vector particle, the method comprising: co-transfecting of a packaging cell line with a psi-negative lentiviral gag/pol gene, a psi-positive lentiviral expression vector and one or two psi-negative expression vector(s) encoding for truncated *morbillivirus* H and F proteins, wherein the truncated cytoplasmic portion of the F protein comprises at least 1 positively charged amino acid residue and the truncated cytoplasmic portion of the H protein is truncated to allow efficient pseudotyping and has fusion support function. Preferably, the *morbillivirus* is a measles virus, or the Edmonston strain of measles virus.

In a further embodiment, the invention is directed to a method for screening for antibodies in a mammalian system comprising:
(a) providing a library of pseudotyped lentiviral vector particles comprising a plurality of different pseudotyped lentiviral vector particles according of the present invention, wherein the truncated H proteins of the pseudotyped lentiviral vector particles have a different single chain antibody at their ectodomain and the vector particles further comprise a bicistronic lentiviral expression vector, wherein said expression vector encodes for the single chain antibody of the respective pseudotyped lentiviral vector particle and an expressible reporter gene;
(b) contacting a population of cells expressing a cell marker with the library of step (a), under conditions to allow transduction of the cells by said vector particles;
(c) selecting cells that express the expressible reporter gene transduced by a pseudotyped lentiviral vector particle of step (a); and
(d) determining the genetic information of the single chain antibody of the pseudotyped lentiviral vector particle that transduced the cell from the selected cells of step (c).

In a further embodiment the invention is directed to a method for the detection or selection of cells expressing a specific cell marker, the method comprising: (a) providing a pseudotyped lentiviral vector particle according to the present invention, wherein the truncated H protein of the said vector particle has a single chain antibody or ligand for said specific cell marker at its ectodomain and said vector particle further comprises an expression vector, wherein said expression vector encodes for a expressible reporter gene; (b) contacting the pseudotyped lentiviral vector particle of step (a) with at least one cell under conditions to allow transduction of the at least one cell by said vector particle; and (c) detecting or selecting the cell(s) that express the expressible reporter gene. Preferably, the identification is carried out in living cell populations or organ cultures.

Finally, in another embodiment the invention is directed to a method for identifying the antigen of an antibody or the receptor of a ligand, the method comprising (a) providing a pseudotyped lentiviral vector particle according to the invention, wherein the truncated H protein of the said vector particle has a known single chain antibody or ligand at its ectodomain, directed against or binding to an antigen or receptor on a cell and said vector particle further comprises an expression vector, wherein said expression vector encodes an expressible reporter gene; (b) transducing cells with an expression library of the cell of step (a); (c) contacting the pseudotyped lentiviral vector particle of step (a) with transduced cells of step (b); (d) selecting cells expressing the expressible reporter gene; and (e) determining the genetic information of the antigen or receptor from the selected cells of step (d).

Additional embodiments of the present invention are described in the claims and the detailed description of the invention.

Definitions

"vector particles", as used in the present invention, refer to replication deficient vectors. Thus, the lentiviral vector particles of the present invention are lentiviral vectors that contain an RNA which, upon infection of a host or target cell, is reverse-transcribed and inserted into the genome of said cell. However, these vector particles only contain an incomplete genome of the lentivirus from which they are derived. In general, the RNA molecule of the vector particle does not comprise the genetic information of the gag, env, or pol genes itself, which is a known minimal requirement for successful replication of a retrovirus. As a result, the vector particles are replication deficient, i.e. they are not able to transduce a host or target cell with the genetic information required for their own replication.

A vector particle thus comprises a minimum of the Gag, Pol, and Env proteins and an RNA molecule (which can be an expression vector). The Gag, Pol, and Env proteins needed to assemble the vector particle are derived from the retrovirus and are provided in trans by means of a packaging cell line, for example HEK-293T. The RNA molecule is derived from the genome of the retrovirus but does not comprise at least one of the gag, env, or pol genes itself. However, to produce a safe and efficient vector particle, in general all three of said genes are lacking, as well as any other nonessential genes. In case of HIV-1, such unnecessary genes of the HIV-1 genome that can be deleted from the RNA molecule include tat, vif, vpr, vpu and nef.

The RNA molecule still comprises all elements, for example, the psi element and LTRs, of the retroviral genome which are required for an effective packaging of the RNA into the resulting vector particles. In the case of an expression vector, the RNA molecule preferably comprises a further gene (usually heterologous) that is under the control of a suitable promoter, for example, the CMV promoter, and is thus expressed upon integration of the gene into the genome of the host or target cell.

Therefore, one example of an RNA molecule that may be used to generate a retroviral vector particle is based on the HIV-1 genome and comprises the LTRs, the psi element and the CMV promoter followed by the gene to be transduced, for example, the gene for a GFP protein. The gag, env, pol, tat, vif, vpr, vpu and nef genes of HIV-1 are removed or expression of their gene products is prevented by, for example, frame shift mutation(s). The minimal requirements for a lentivirus vector based on HIV-1 have been described by Kim et al. (J. Virology, 72:811-816, 1998).

The above-described RNA molecule together with the gag, pol and env proteins, provided in trans by the packaging cell line, are then assembled into the vector particles or vector particles, which will be able to efficiently infect their target or host cells, reverse-transcribe the RNA molecule that may comprise a heterologous gene under the control of the CMV promoter, and integrate said genetic information into the genome of the target/host cells. However, as the genetic information for the gag, pol and env proteins is not present on the transduced RNA molecule, the vector particles or vector particles will be replication deficient, i.e. no new generation of said vector particles will thus be generated by the transduced cell.

The term "pseudotyped", "pseudotyped vector" or "pseudotyped vector particle", as used in the present invention, refers to a vector particle bearing envelope glycoproteins derived from other viruses having envelopes. The host range of the lentiviral vectors vector particles of the present invention can thus be expanded or altered depending on the type of cell surface receptor used by the glycoprotein.

As explained in the foregoing section, the gag, pol and env proteins needed to assemble the vector particle are provided in trans by means of a packaging cell line, for example, HEK-293T. This is usually accomplished by transfection of the packaging cell line with one or more plasmids containing the gag, pol and env genes. For the generation of pseudotyped vectors, the env gene, originally derived from the same retrovirus as the gag and pol genes and as the RNA molecule or expression vector, is exchanged for the envelope protein(s) of a different enveloped virus. As an example, the F and H protein of MeV are used.

Thus, an exemplary pseudotyped vector particle based on the HIV-1 retrovirus comprises the (1) HIV-1 Gag and Pol proteins, (2) an RNA molecule derived from the HIV-1 genome that may be used to generate a retroviral vector particle based on the HIV-1 genome lacking the gag, env, pol, tat, vif, vpr, vpu and nef genes, but still comprising the LTRs, the psi element and a CMV promoter followed by the gene to be transduced, for example, a gene for the GFP protein, and (3) the F and H proteins of MeV$_{Edm}$, for example, in a truncated form as disclosed by the present invention.

The resulting pseudotype vector particle will thus display the tropism of MeV$_{Edm}$, i.e. have the ability to effectively transduce cells expressing the CD46 and/or SLAM proteins on their surface.

"Cell entry targeted" or "targeted" lentiviral vector particles are pseudotyped vector particles of the present invention, wherein the H protein is a chimeric protein that does not interact with CD46 or SLAM and further has a single chain antibody, a growth factor or a ligand to a cell surface marker at its ectodomain. Thus, the host range of a cell entry targeted lentiviral vector particles of the present invention is not expanded or altered depending on the tropism of the virus the H protein is derived from, but, depending on the specificity of the single chain antibody, growth factor or ligand fused to the H protein.

A pseudotyped vector particle "derived from", for example, HIV-1, as used in the present invention, refers to a vector particle in which the genetic information for the RNA and/or the Gag and Pol proteins comprised by the vector particle originally stems from said retrovirus, in the above case, HIV-1. As described above, the original retroviral genome can comprise mutations, such as deletions, frame shift mutations and insertions.

The term "cytoplasmic portion", "cytoplasmic tail" or "cytoplasmic region", as used in the present invention, refers to the portion of the respective protein that is adjacent to the transmembrane domain of the protein and, if the protein is inserted into the membrane under physiological conditions, extends into the cytoplasm. For the MeV F protein, the transmembrane domain is identified by the amino acid sequence "LICCC" (SEQ ID NO: 5), for the MeV H protein, the domain is identified by the amino acid sequence "PYVL" (SEQ ID NO: 6). The cytoplasmic portion of the MeV F protein usually consists of the 33 C-terminal amino acids, in the case of the MeV Edmonston strain (MeV$_{Edm}$) it consists of the amino acid sequence "RGRCNKK-GEQVGMSRPGLKP DLTGTSKSYVRSL" (SEQ ID NO: 7). The cytoplasmic portion of the MeV H protein typically consists of the 34 N-terminal amino acids, in the case of MeV$_{Edm}$, the protein consists of the amino acid sequence "MSPQRDRINAFYKDNPHPKGSRIVINREHLMIDR" (SEQ ID NO: 8).

The term "truncated", as used in the present invention, refers to a deletion of amino acid residues of the designated protein. It is clear to the skilled person that a protein is encoded by a nucleic acid. Thus, "truncated" also refers to the corresponding coding nucleic acids in a nucleic acid molecule that codes for a given "truncated" protein. Furthermore, it is to be understood that the nucleic acid molecules encoding for a specific truncated or modified protein of the present invention are likewise encompassed, and vice versa. For example, this means that if a given protein is referred to, e.g. a truncated F protein such as FcΔ30, the nucleic acid encoding said protein is likewise encompassed by the present invention. Furthermore, nucleic acid molecules that comprise such a nucleic acid molecule encoding for a given protein of the invention, for example, plasmid or expression vectors, are likewise encompassed.

In the present invention, reference is made to "truncated H" or "truncated F" proteins, which designates the *morbillivirus*, preferably MeV H and F proteins, respectively, whose cytoplasmic portion has been truncated, i.e. amino acid residues (or coding nucleic acids of the corresponding nucleic acid molecule encoding the protein) have been deleted. HcΔX and FcΔX designate such truncated H and F proteins, respectively, wherein X residues of the cytoplasmic portion have been deleted.

The cytoplasmic portion of the F protein is located at the C-terminus of the protein. Thus, one begins counting from the C-terminal end of the F protein when ascertaining the desired sequence. As an example, if starting from the F protein of MeV$_{Edm}$, having the above-described sequence, FcΔ24 would then refer to an F protein having a cytoplasmic portion with the amino acid sequence "RGRCNKKGE" (SEQ ID NO: 9), while FcΔ30 would refer to an F protein having a cytoplasmic portion with the amino acid sequence "RGR".

By contrast, the cytoplasmic portion of the H protein is located at the N-terminus. Thus, one begins counting at the second amino acid residue of the N-terminal end of the H protein (i.e. omitting the first methinonine residue) when ascertaining the desired sequence. As an example, if starting from the H protein of MeV$_{Edm}$, having the above-described sequence, HcΔ18 would then refer to an H protein having a cytoplasmic portion with the amino acid sequence "MGSRIVINREHLMIDR" (SEQ ID NO: 10), while HcΔ19 would refer to an H protein having a cytoplasmic portion with the amino acid sequence "MSRIVINREHLMIDR" (SEQ ID NO: 11). Additionally, HcΔX+YZ designates a truncated H protein, wherein X residues of the cytoplasmic portion have been deleted as described above and wherein a number of Y amino acid residues have been added to the N-terminal portion of the remaining cytoplasmic portion (again omitting the first methinonine residue). Z defines, by the one-letter amino acid code, the amino acid residue to be added Y-fold. Thus, as an example, if starting from the H protein of MeV, having the above given sequence, HcΔ24+4A would then refer to an H protein having a cytoplasmic portion with the amino acid sequence "MAAAANREHLMIDR" (SEQ ID NO: 12).

Surprisingly, the inventors have found that cytoplasmic domain of the F protein can be truncated to comprise at least 1 positively charged amino acid residue and the cytoplasmic portion of the H protein can be truncated to comprise at least 9 consecutive amino acid residues of the C-terminal cytoplasmic portion of the H protein plus an additional methinonine at the N-terminus.

However, a further truncation of the cytoplasmic portion of the H protein is expected to be feasible, if the H protein is truncated to allow efficient pseudotyping and still has fusion support function.

The person skilled in the art will readily be able to introduce mutations as, for example, additions and deletions, into a given nucleic acid or amino acid sequence. Such known methodologies are, for example, disclosed in Sambrook et al. (1989).

Using the nucleic acid sequences disclosed herein, the skilled person can further design nucleic acid structures having particularly desired functions in various types of applications. For example, the artisan can construct oligonucleotides or polynucleotides for use as primers in nucleic acid amplification procedures, such as the polymerase chain reaction (PCR), ligase chain reaction (LCR), Repair Chain Reaction (RCR), PCR oligonucleotide ligation assay (PCR-OLA), and the like. Oligonucleotides useful as probes in hybridization studies, such as in situ hybridization, can also be constructed. Numerous methods for labeling such probes with radioisotopes, fluorescent tags, enzymes, and binding moieties (e.g., biotin) are known, thus the probes of the present invention can be adapted for detectability in a straightforward manner.

Oligonucleotides can also be designed and manufactured for other purposes. For example, the present invention enables the artisan to design antisense oligonucleotides and triplex-forming oligonucleotides for use in the study of structure/function relationships. Homologous recombination can be implemented by adapting the nucleic acid of the invention for use as a targeting means.

The invention particularly includes nucleic acids sequences or homologs thereof, or unique fragments thereof. In the present invention, the sequence of a nucleic acid molecule that encodes a resulting protein is considered homologous to a second nucleic acid molecule if the nucleotide sequence of the first nucleic acid molecule is at least about 70% homologous, preferably at least about 80% homologous, and more preferably at least about 85%, 90%, 95% or 99% homologous to the sequence of the second nucleic acid molecule. Homology between two nucleic acid sequences may be readily determined using the known BLASTN algorithm (Altschul, et al., 1990) with default settings. As a further example, another known test for ascertaining the homology of two nucleic acid sequences is whether they hybridize under normal hybridization conditions, preferably under stringent hybridization conditions.

The protein encoded by the nucleic acid of the present invention further includes functional homologs. A protein is considered a functional homolog of another protein for a particular function, if the homolog has a similar function as the original protein. The homolog can be, for example, a fragment of the protein, or a substitution, addition, or deletion mutant of the protein.

Determining whether two amino acid sequences are substantially homologous is typically based on FASTA searches in accordance with Pearson & Lipman (1988). For example, the amino acid sequence of a first protein is considered to be homologous to that of a second protein if the amino acid sequence of the first protein shares at least about 70% amino acid sequence identity, preferably at least about 80% identity, and more preferably at least about 85%, 90%, 95% or 99% identity, with the sequence of the second protein.

"Psi positive" and "psi negative", as used in the present application, refers to a nucleic acid molecule where the retroviral psi element is present and absent, respectively. The psi element is a cis-acting signal located near the 5' end of the retroviral genome and designates a packaging signal, which is of importance during assembly of the viruses and leads to the incorporation of the viral RNA into the viral core. Thus, a psi negative RNA does not comprise the retroviral psi element and consequently will not be assembled into a vector particle of the present invention; in contrast, a psi positive RNA that does comprise said psi element will be effectively assembled into the vector particle.

"Titers" and "transduction efficiency" refer to the ability of a vector particle to enter a cell and integrate the genetic information, in particular RNA information, into the genome of the cell. Thus, the terms "titer" and "transduction efficiency" can be used synonymously. The titer/transduction efficiency can, for example, be determined by incorporation of a gene coding for a detectable marker, for example, under the control of a CMV promoter, into the expression vector of the vector particle. Upon transduction of such a detectable marker by means of the vector particle, the transduced cells will then express the detectable marker. If the detectable marker is, for example, the GFP protein, the number of cells infected by a given number of vector particles can readily be determined, e.g. by FACS analysis, and directly corresponds to the titer or transduction efficiency of the vector particles that have been used for transduction. The titer or transduction efficiency of a given vector particle thus refers to the number of cells transduced relative to the number of vector particles used.

The titer or transduction efficiency is used as a means to characterize and compare vector particles with regard to their ability to transduce their target cells. Thus, a vector particle having an "increased titer" or an "increased transduction efficiency" is able to transduce a higher number of cells at a given vector particle concentration than a different vector particle having the same vector particle concentration.

The term "cell marker", or "cell surface marker", as used in the present invention, refers to a molecule present on the surface of a cell. Such molecules can be, inter alia, peptides or proteins that may comprise sugar chains or lipids, antigens, clusters of differentiation (CDs), antigens, antibodies or receptors. Since not all populations of cells express the same cell markers, a cell marker can thus be used to identify, select or isolate a given population of cells expressing a specific cell marker. As an example, CD4 is a cell marker expressed by T helper cells, regulatory T cells, and dendritic cells. Thus, T helper cells, regulatory T cells, and dendritic cells can be identified, selected or otherwise isolated, inter alia by a FACS cell sorter, by means of the CD4 cell marker.

The term "tagging sequence", as used in the present invention, refers to a specific and known nucleic acid sequence. Such a tagging sequence can, inter alia, be used as a starting point for a sequencing reaction. As an example, the plasmids used in the generation of libraries of the vector particles of the present invention or cDNA libraries can contain such a tagging sequence. If this tagging sequence is a universal tagging sequence, i.e. if the same is present in every plasmid and thus in the resulting cDNA expression vectors and vector particle of said libraries, then any of said plasmids, cDNA expression vectors and vector particles can be sequenced by using the same starting primer that is designed to include the universal tagging sequence or its complement.

The term "selectable marker" or "selectable marker gene", as used in the present invention, refers to a gene and its corresponding product that allow detection, selection and/or isolation of said product. If such a selectable marker is expressed by a cell, consequently such a cell or a population of such cells can be detected, selected and/or isolated.

Selectable markers can be, inter alia, a molecule, preferably a peptide or protein, detectable by fluorescence, an enzyme catalyzing a reaction of which the resulting product is monitored, a molecule that confers a resistance to, inter alia, an antibiotic or another toxic substance, or a molecule interacting with a non-toxic substance to render it toxic. Detection, selection and/or isolation can be carried out, inter alia, by FACS, a FACS cell sorter, use of fluorescence microscopy, or by the use of antibiotics or cytotoxic substances, use of precursors of cytotoxic substances.

BRIEF DESCRIPTION OF THE FIGURES

FIGS. 1A and 1B depict the DNA (SEQ ID NO: 31) and amino acid (SEQ ID NO: 32) sequence of the MeV $H_{Edm}$ wildtype (wt) protein, wherein the portion of the cytoplasmic domain is shown in bold.

FIGS. 2A and 2B show the (DNA SEQ ID NO: 33) and amino acid (SEQ ID NO: 34) sequence of the MeV $F_{Edm}$ wildtype (wt) protein, wherein the portion of the cytoplasmic domain is shown in bold.

FIGS. 3A-3C exemplarily show the DNA sequence of three of the truncated H proteins derived from the $H_{Edm}$ wt DNA, namely, HcΔ18 (SEQ ID NO: 35), HcΔ19 (SEQ ID NO: 36) and HcΔ24+4A (SEQ ID NO: 37), respectively. FIG. 3D exemplarily depicts the amino acid sequence of HcΔ18 (SEQ ID NO: 38). FIGS. 3E and 3F exemplarily show the DNA (SEQ ID NO: 39) and amino acid (SEQ ID NO: 40) sequence of one of the truncated F proteins derived from the $F_{Edm}$ wt DNA, namely FcΔ30. The cytoplasmic portions are shown in bold. FIG. 3G depicts the DNA sequence (SEQ ID NO: 41) of the truncated HcΔ24 protein, wherein an additional four alanine residues were added to thus yield HcΔ24+4A. Again, the cytoplasmic portions are shown in bold.

FIGS. 4A and 4B provide an overview over exemplary generated F and H mutant proteins in comparison to their respective wt molecules, indicating the deleted (or added) amino acid residues in the cytoplasmic portion of the proteins. FIGS. 4A and 4B disclose SEQ ID NOS 42-43 and 44-47, respectively.

FIGS. 5A and 5B depict the DNA (SEQ ID NO: 1) and amino acid sequences (SEQ ID NO: 2) of the resulting HmutscFvCD20Δ18 molecule as derived from HcΔ18. The four mutation sites are underlined, the SfiI and NotI restriction sites, flanking the scFvCD20 are designated in italics, the HIS-tag is designated underlined and in italics. FIG. 5C shows the plasmid map of the HmutscFvCD20Δ18 plasmid.

FIGS. 6A and 6B depict the DNA (SEQ ID NO: 48) and amino acid (SEQ ID NO: 49) sequence of an EGF ligand (SfiI and NotI restriction sites are designated in italics), which was used to construct a corresponding HmutEGFΔ18 molecule (SEQ ID NOs: 3 and 4).

FIGS. 7A-7D show exemplary microscopic pictures of HT1080 cells transduced with the pseudotyped vector particles, i.e. the GFP transduction of HT1080 cells by means of the FcΔ30/HcΔ19, FIG. 7C FcΔ30/HcΔ24+4A, and FIG. 7D Fwt/Hwt, respectively. In all cases, the HEK-293T cells were co-transfected with packaging plasmid pCMVΔR8.9 and the GFP reporter gene plasmid.

FIG. 8A-8F, FIG. 8A shows that CD46 and SLAM expressing HT1080 cells are clearly and efficiently transduced by the vector particles pseudotyped with HT1080-CD20 cells (where the cells additionally express CD20), while FIG. 8B shows no such transduction for the HmutscFvCD20Δ19 and FcΔ30 vector particles. FIG. 8C-F show the results for the positive and negative controls (FIG. 8C: positive control using HT1080-CD20 cells; FIG. 8D positive control using HT1080 cells; FIG. 8E negative control using HT1080-CD20 cells; FIG. 8F negative control using HT1080 cells).

FIG. 9 shows the plasmid map of pCG-HcΔ18.

FIG. 10 shows the plasmid map of pCG-FcΔ30.

FIG. 11 shows the plasmid map of packaging plasmid pCMVΔR8.9 encoding the HIV-1 gag and pol genes.

FIG. 12 shows the plasmid map of transfer plasmid SEW encoding eGFP.

FIG. 13A-13B shows titer reduction of HIV-1 vector particles pseudotyped with the modified MeV glycoproteins on HT1080 cells transduced in the presence of AZT. 293T cells were co-transfected with the packaging plasmid encoding HIV-1 gag/pol, the transfer plasmid encoding GFP and the two plasmids encoding the H and F protein variants, respectively. FIG. 13A After 48 h the cell supernatants containing HIV-1 vector particles pseudotyped with HcΔ18/FcΔ30, HcΔ19/FcΔ30 or HcΔ24+4A/FcΔ30 were filtrated, concentrated and used for the transduction of HT1080 cells in the presence or absence of 10 μM AZT. The titers obtained in presence of AZT were normalised to those obtained in absence of AZT and converted to titer reductions as listed in the figure. Exemplary photos of the cells transduced by HcΔ18/FcΔ30 pseudotyped HIV-1 vector particles are shown FIG. 13B.

Figure 14A:
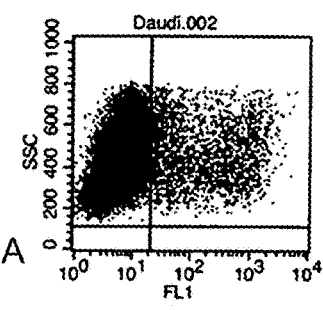
Figure 14C:
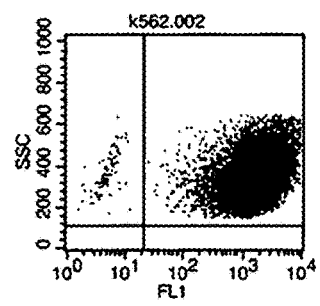
Figure 14B:
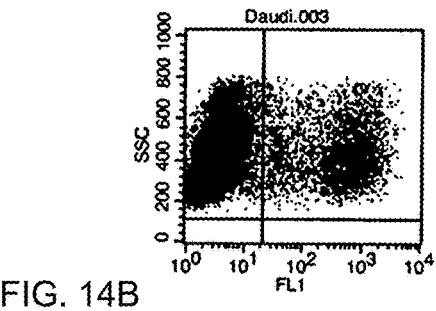

FIGS. 14A-14D shows selective transduction of lymphocytes that naturally express CD20. Concentrated HIV-1 vector particles pseudotyped with VSV-G as positive control FIGS. 14A-14C or with HmutscFvCD20Δ18 and FcΔ30 FIG. 14B were used for the transduction of the CD20 positive Daudi B cell line (FIGS. 14A-14D) and the CD20 negative K-562 myeloid cell line. FIGS. 14A-14C The GFP fluorescence of transduced cells was detected by FACS.

Figure 15:
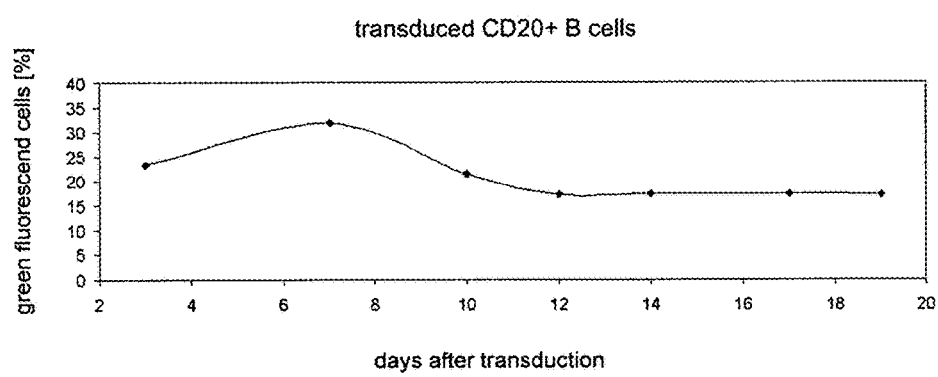

FIG. 15 shows Long-term cultivation of transduced B cells. CD20 positive Raji B cells were transduced by HmutscFvCD20Δ18/FcΔ30 pseudotyped HIV-1 vector particles with the gfp reporter gene and cultivated for 19 days. At different time points after transduction the percentage of GFP positive cells was determined by FACS analysis.

Figure 16:
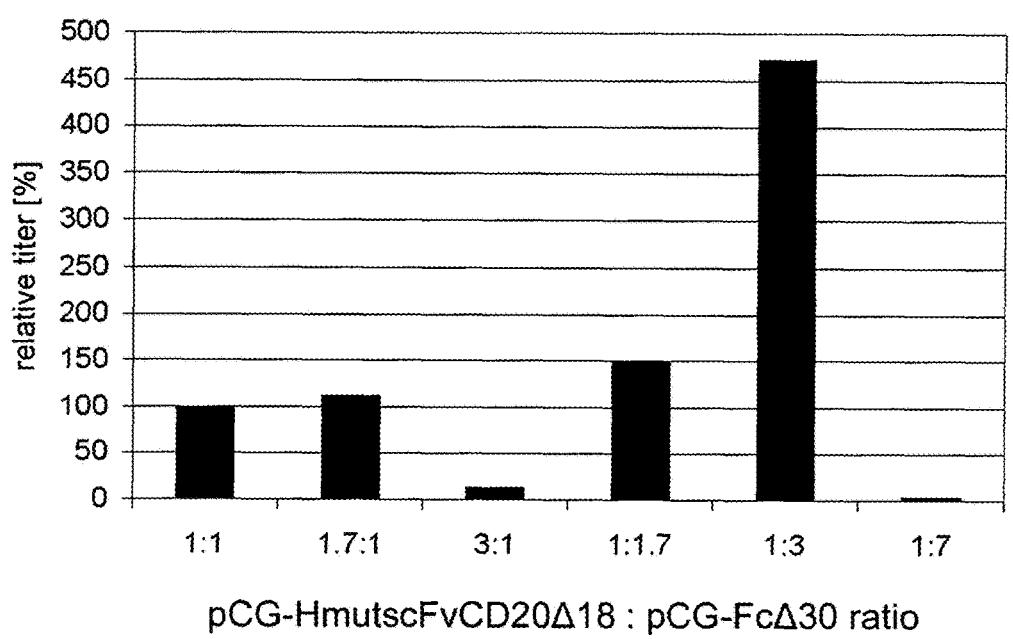

FIG. 16 shows relative titers of HmutscFvCD20Δ18/FcΔ30 pseudotyped HIV-1 vector particles using different amounts of pCG-HmutscFvCD20Δ18 and pCG-FcΔ30 plasmid for vector particle production. The ratio of the plasmids encoding HmutscFvCD20Δ18 and FcΔ30, respectively, was titrated for co-transfection. The produced HIV-1 vector particles were used for the transduction of HT1080-CD20 cells and the detected titers were set in relation to the titer of the vector particles with a HmutscFvCD20Δ18 to FcΔ30 ratio of 1:1.

FIGS. 17A-17F shows targeting of SLAM positive Raji cells (FIGS. 17A-17C) in a mixed cell population by HwtΔ18/FwtΔ30 pseudotyped HIV-1 vector particles. A mixture of SLAM positive Raji and SLAM negative HT1080 cells (FIGS. 17D-17F) was transduced by HIV-1 vector particles that were pseudotyped with the modified glycoproteins of the wild type measles virus 323. 48 h after transduction the Raji and HT1080 cells were separated and stained against CD20, FIGS. 17A and 17D, 1:10; 17B and 17E, 1:50; 17C and 17F, 1:500 which is specific for the Raji cells. Then the CD20 and GFP positive cells were measured by FACS.

Figure 18A:
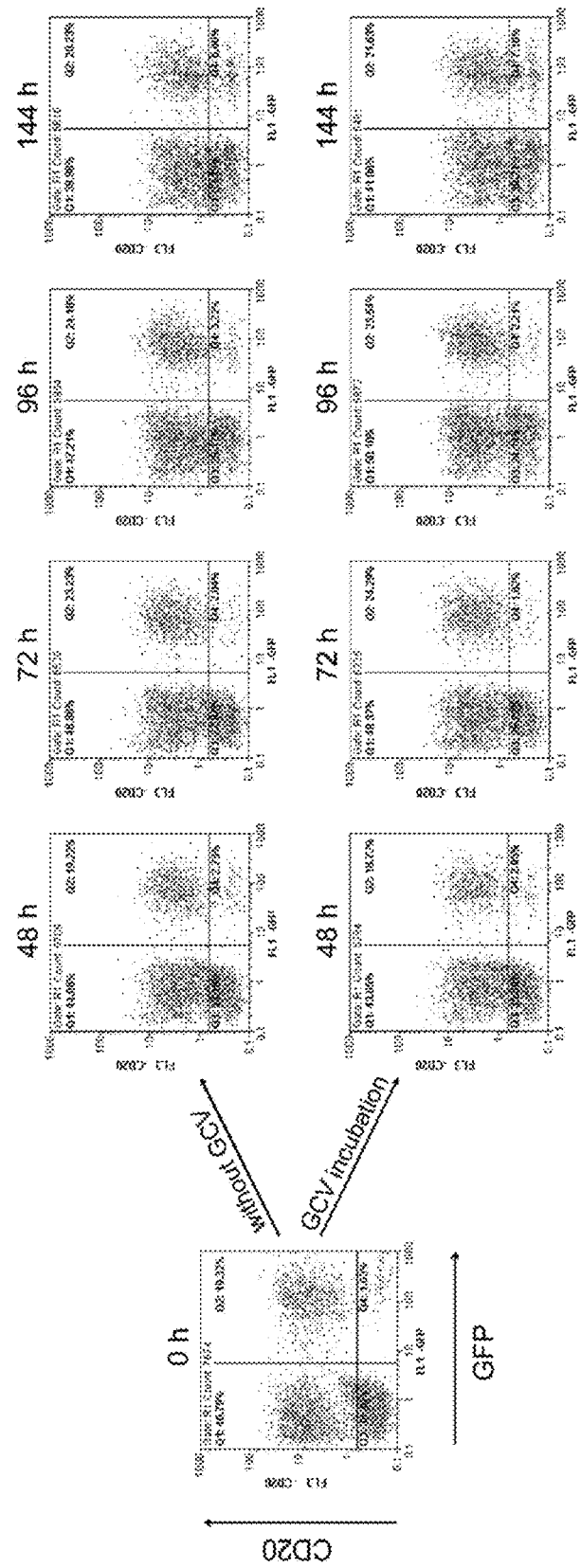
Figure 18B:
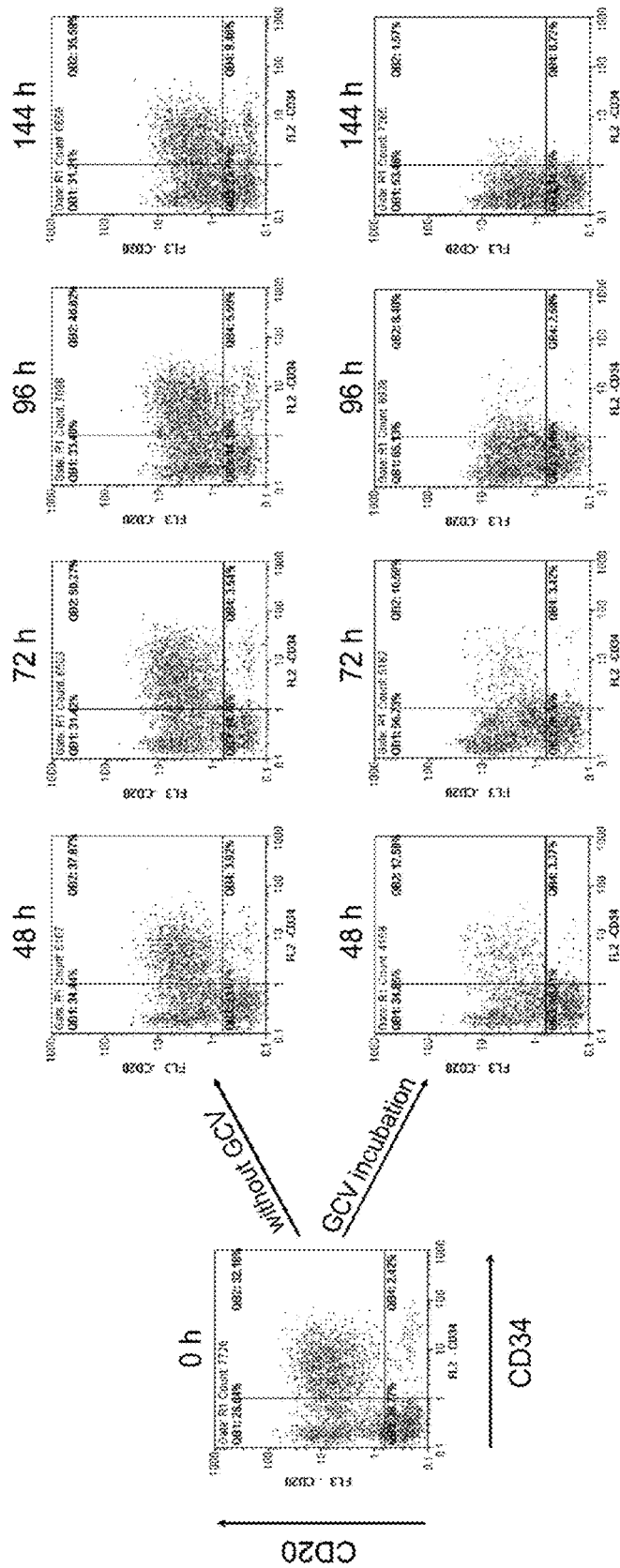

FIGS. 18A-18B shows selective killing of CD20 positive cells in a mixed cell population. CD20 positive Raji and CD20 negative K-562 cells were mixed in the same ratio and were then transduced with HmutscFvCD20Δ18/FcΔ30 pseudotyped HIV-1 vector particles either with packaged gfp gene FIG. 18A or with packaged cd34tk39 gene FIG. 18B. Five days after transduction the cells were stained against CD20 (a) or CD20 and CD34 FIG. 18B and the percentage of CD20/GFP and CD20/CD34 double positive cells, respectively, was determined by FACS (time point 0 h). Next, half of the transduced cells was incubated in 10 μM Gancyclovir (GCV) containing medium and the other half was left as control in GCV-free medium. At different time points the cells were stained with the respective antibodies and the double positive cells were measured by FACS.

FIGS. 19A-19E shows selective transduction of GluR4 positive HT1080 cells by HmutscFvGluR4Δ18/FcΔ30 pseudotyped HIV-1 vectors. HT1080-GluR4 and parental HT1080 cells were transduced with the gfp gene using HmutscFvGluR4Δ18/FcΔ30 pseudotyped HIV-1 vector particles. 48 h after transduction cells were analyzed under the fluorescence microscope (FIGS. 19A and 19B) or by FACS after antibody staining against GluR4 (FIGS. 19C, 19D, 19E, 1:10; 1:100, 1:1000) respectively.

Figure 20A:
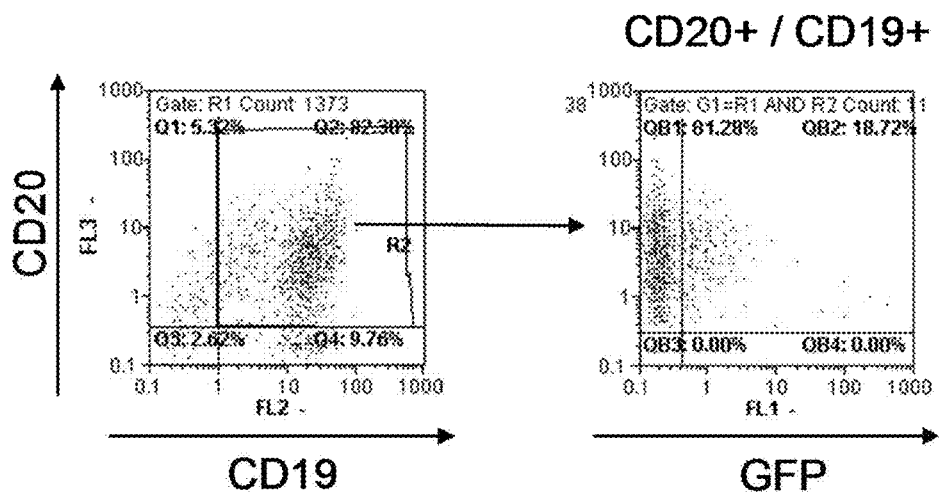
Figure 20B:
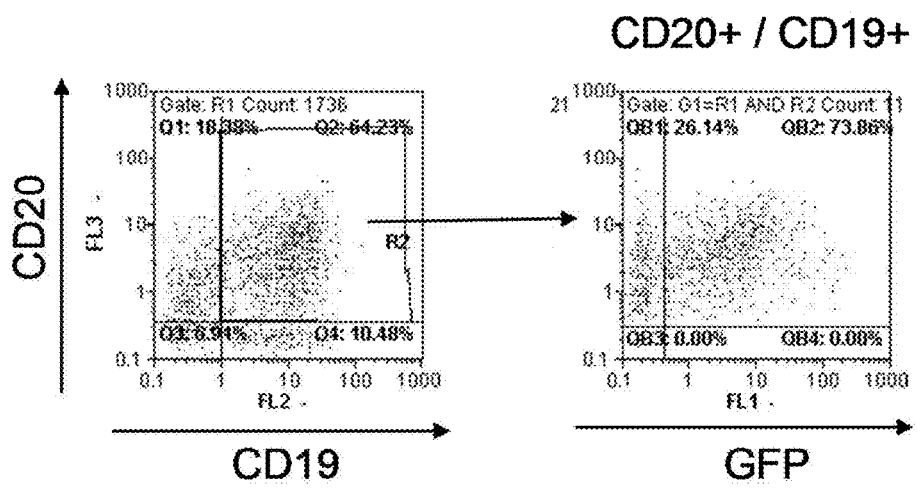
Figure 20C:
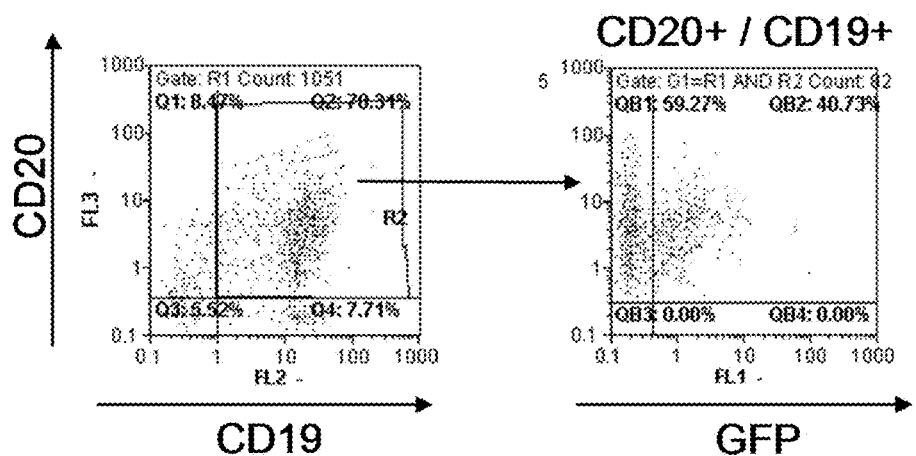

FIG. 20A-20C shows transduction of primary human B cells by HIV-1 vector particles pseudotyped with HmutscFvCD20Δ18/FcΔ30 or VSV-G. Primary human B cells were isolated from human PBMCs, 48 h activated with different cytokines and then transduced with VSV-G pseudotyped HIV-1 vector particles (FIG. 20A) or with HmutscFvCD20Δ18/FcΔ30 pseudotyped HIV-1 vector particles (FIG. 20B). FIG. 20C had MOI 150 72 h after transduction the cells were stained against the B cell markers CD20 and CD19 and the percentage of CD20/CD19/GFP triple positive cells was determined by FACS.

FIG. 21A-21D shows targeted transduction of a mixture of primary human B and T cells. A mixture of primary human B and T cells was activated with cytokines and then transduced with FIG. 21A VSV-G pseudotyped HIV-1 vector particles as control FIG. 21A or with HmutscFvCD20Δ18/FcΔ30 pseudotyped HIV-1 vector particles FIG. 21B. 48 h after transduction the cells were stained against the B cell markers CD20 and CD19 and the percentage of GFP positive cells was measured by FACS.

Figure 22:
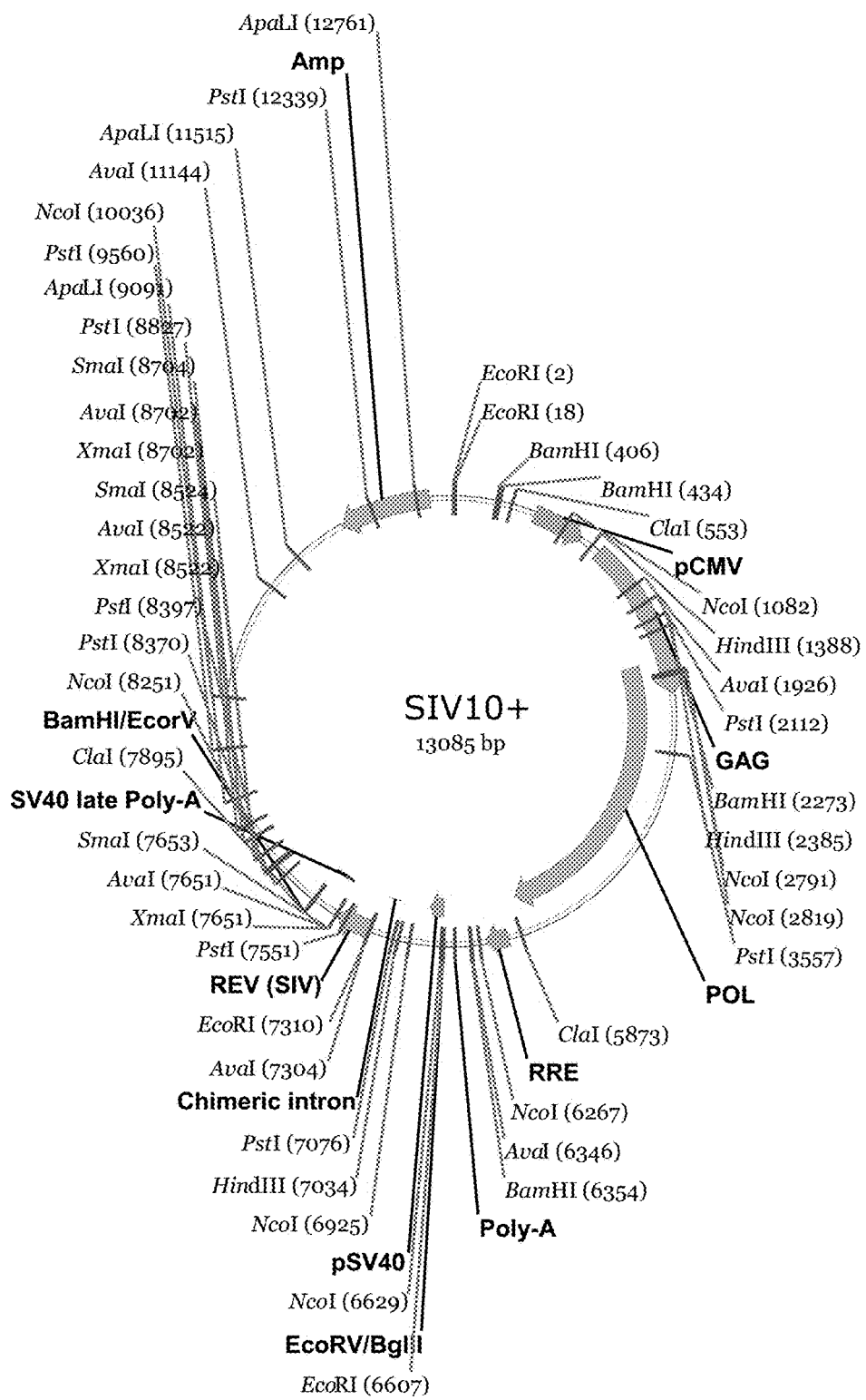

FIG. 22 shows a map of the SIVmac packaging plasmid SIV10+.

Figure 23:
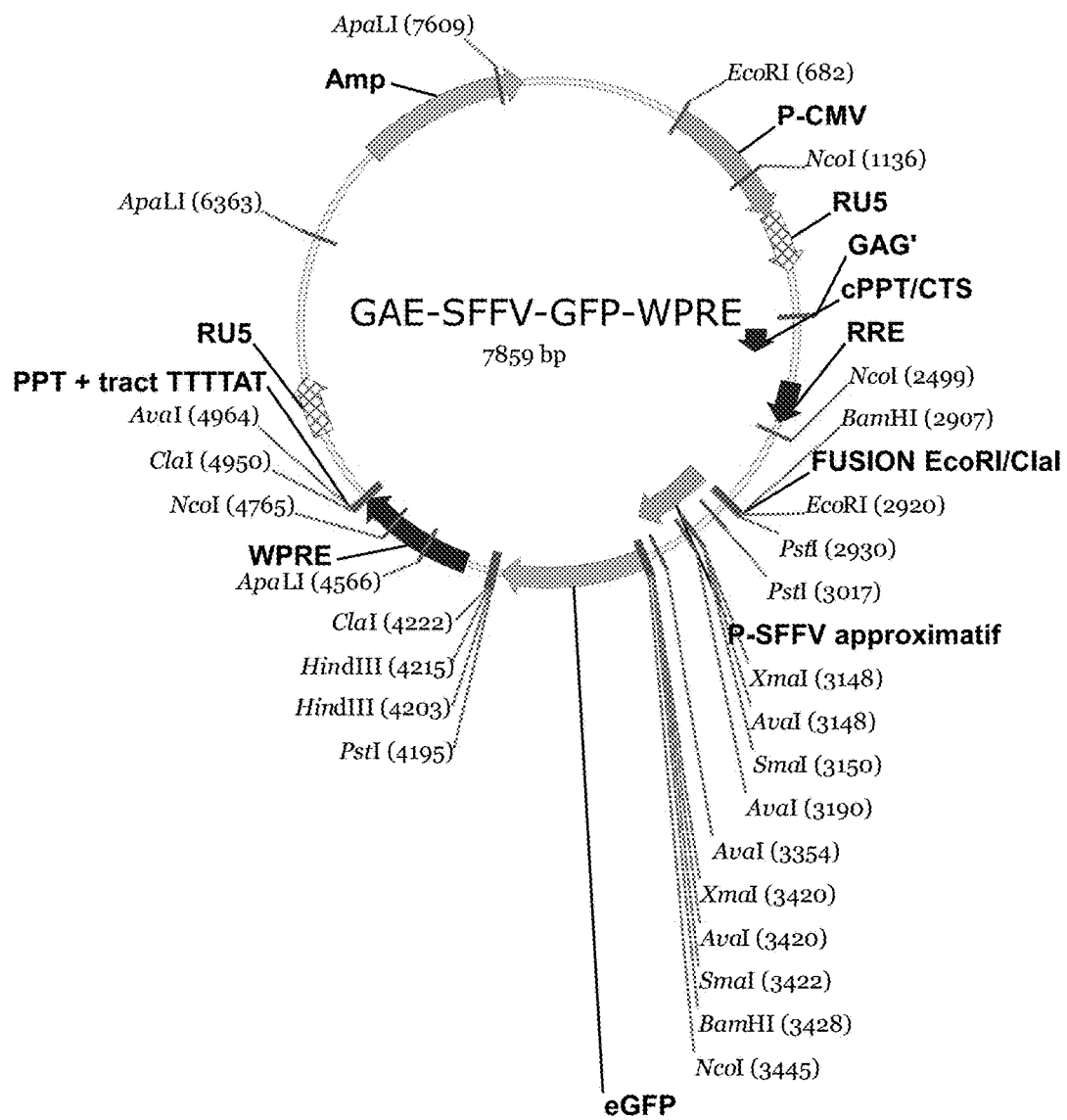

FIG. 23 shows a map of the SIVmac transfer plasmid GAE-sffv-gfp-wpre.

Figure 24:
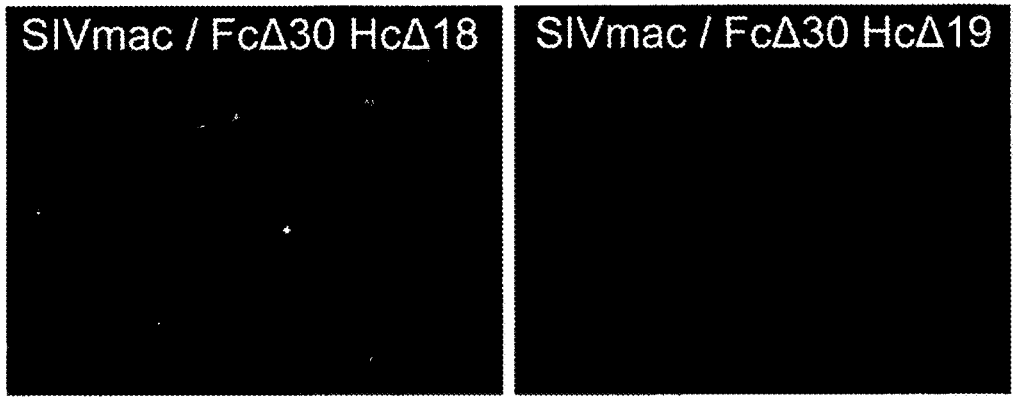

FIG. 24 shows transduction of HT1080 cells by SIVmac vector particles pseudotyped with modified MeV glycoproteins. 293T cells were co-transfected with the SIVmac packaging plasmid encoding gag/pol, the transfer plasmid encoding GFP and the two plasmids encoding the H and F protein variants, respectively. After 48 h the cell supernatants, that contain the HcΔ18/FcΔ30 and HcΔ19/FcΔ30 pseudotyped SIVmac vector particles, respectively, were filtrated, concentrated and used for the transduction of HT1080 cells.

DETAILED DESCRIPTION OF THE INVENTION

I. Overview: Retroviridae and Generation of Lentiviral Vector Particles

1. Taxonomy

Viruses of the taxonomic family of the Retroviridae share, as a main feature, a positive stranded ssRNA genome (ss(+)RNA). Because during infection, said ss(+)RNA can not directly be used as a template (mRNA), the genetic information of this virus is thus first reverse-transcribed from RNA into DNA by a reverse transcriptase provided by the virus and subsequently integrated into the host genome. Thus, the term "retro" refers to the activity of reverse transcriptase and the transfer of genetic information from RNA to DNA. Today, more than 570 individual viruses of the family have been identified.

One sub-family of Retroviridae comprises the Orthoretroviridae viruses, including the genera of the alpha-retroviruses with, for example, the Avian leukosis virus (ALV) species; the gamma-retroviruses with, for example, the Murine leukemia virus (MLV) species; or the Feline leukemia virus (FLV) or the delta-retroviruses with, for example, the Bovine leukemia virus (BLV) species or the Human T-lymphotropic virus (HTLV).

One additional genus of the Orthoretroviridae, known as the lentiviruses, has recently attracted much interest mostly due to one of its well-known members, the Human immunodeficiency virus (HIV). However, the genus of lentiviruses comprises numerous other viruses: in addition to the HIV-1 or HIV-2 species, the Bovine immunodeficiency virus (BIV), the Feline immunodeficiency virus (FIV) and the Simian immunodeficiency virus (SIV) are all frequent subjects of extensive research efforts.

2. Structural and Genetic Features of Lentiviral Genomes

The genome of known replication-competent retroviruses comprises the four coding domains (gag, pro, pol, env):

The first of the four coding domains (gag) encodes a polypeptide (Gag) whose cleavage products are the major structural proteins of the virus core and consist of: Matrix (MA), which is associated with the inside of the virus envelope; capsid (CA), a principal structural protein of the virion core; and nucleocapsid (NC), a small, basic protein which is tightly bound to the viral genomic RNA and forming a ribonucleoprotein complex within the core.

The second of the four coding domains (pro) encodes part of the polyprotein (Gag-Pro or Gag-Pro-Pol) whose cleavage products typically include protease (PR) and occasionally dUTPase (DU).

The third of the four coding domains (pol) encodes part of the polyprotein (Gag-Pro-Pol), whose cleavage products typically include reverse transcriptase (RT) and integrase (IN) and, in some lentiviruses, dUTPase (DU). In spumaviruses, pol is expressed via a spliced mRNA as Pol-Pol polyprotein.

Finally, env encodes a polyprotein (Env) whose cleavage products SU (surface) and TM (transmembrane) comprise the structural proteins of the viral envelope. These proteins are not required for the assembly of enveloped viral vector particles, but they do have an essential role in the cellular entry process. The SU domain binds to a specific receptor molecule on the target cell. This binding event appears to activate the membrane fusion-inducing potential of the TM protein and, by a process that remains largely undefined, the viral and cell membranes then fuse. The specificity of the SU/receptor interaction defines the host range and tissue tropism of a retrovirus. As a consequence, viral vector particles lacking envelope glycoproteins are noninfectious, and cells lacking a receptor are nonpermissive for viral entry. Viruses may bind weakly to resistant cells through relatively nonspecific interactions, but, in the absence of a specific receptor molecule, they are unable to initiate the infection process.

In addition, retroviruses contain two long terminal repeats (LTRs), a region of several hundred (~300-1800) base pairs composed of U3-R-U5 (5' to 3') which are located at both ends of the unintegrated and integrated (proviral) genome.

Furthermore, a psi element is present within the retroviral genome. The psi element is a cis-acting signal, located near the 5' end of the genome and designates a packaging signal, which is of importance during virus assembly and leads to the incorporation of the viral RNA into the viral core.

More complex retroviruses typically comprise additional regulatory genes. In case of HIV, these include tat, rev, vif, nef, vpu und vpr.

3. Lentiviral Vector Particles and their Generation

Lentiviral vector particles are replication deficient lentiviral vectors and are useful for transducing a nucleic acid sequence into a target/host genome. Such vector particles comprise a minimum of the Gag, Pol and Env proteins and an RNA molecule, which can be an expression vector. This RNA molecule or expression vector is usually derived from the genome of the original retrovirus, which means that it comprises all the necessary elements for an effective packaging into the resulting lentiviral vector particles (inter alia the psi element and LTRs). However, in order for the lentiviral vector particle to be replication deficient, the RNA molecule does not comprise the genetic information of the gag, env, or pol genes itself. Instead, a normally heterologous nucleic acid sequence to be integrated into the target/host genome is present in the expression vector. The minimal requirements for a lentivirus vector based on HIV-1 have been described by, for example, Kim et al. (J. Virology, 72:811-816, 1998).

Thus, for generating lentiviral vectors, three basic components, usually provided on separate plasmids, are required: a psi-negative gag/pol gene, a psi-negative env gene and a psi-positive expression vector. Co-transfection of these components into a packaging cell line, i.e. a suitable eukaryotic cell line, will lead to the expression of the Gag, Pol and Env proteins as well as generation of psi-positive RNA (however, use of cell lines that are stably transfected with one or more of these basic components is certainly possible). Since the gag/pol and env genes are psi-negative, the mRNA generated prior to expression of the corresponding proteins will not be assembled into the lentiviral vector particles. Contrasting this, the psi-positive RNA transcribed from the expression vector will be included in the resulting lentiviral vector particle.

Consequently, replication deficient lentiviral vector particles will be generated comprising the Gag, Pol and Env proteins provided in trans by the packaging cell line, as well as the psi-positive RNA transcript of the expression plasmid lacking the genetic information for autonomous replication. However, as the lentiviral vector particles comprise the Gag, Pol and Env proteins, they will be able to efficiently infect their target/host cells, reverse-transcribe their RNA, and integrate said genetic information into the genome of the target/host.

4. Pseudotyped Heterologous Lentiviral Vector Particles

The host range of lentiviral vectors can be expanded or altered by a process known as pseudotyping. The process of pseudotyping a lentivirus or a lentiviral vector particle is generally understood to result in a lentiviral vector particle that consists of a lentiviral vector particle bearing glycoproteins derived from other enveloped viruses. Such vector particles possess the tropism of the virus from which the glycoprotein(s) were derived.

As described above, for generating lentiviral vector particles, three basic components, usually provided on separate plasmids, are required. Within a packaging cell line, a psi-negative gag/pol gene of the original lentivirus, a psi-negative env gene of the original lentivirus, and a psi-positive expression vector are needed. For pseudotyped lentiviral vector particles, the env gene of the original retrovirus is replaced by one or more envelope gene(s) of another enveloped virus, for example, the genes coding for the F and H proteins of MeV. Furthermore, the RNA transcribed from the psi-positive expression vector will be assembled into the resulting lentiviral vector particle. This psi-positive expression vector is usually derived from the genome of the original retrovirus, which means that it comprises all the necessary elements for an effective packaging into to resulting pseudotyped lentiviral vector particles. Furthermore, this expression vector may carry at least one gene which is to be transduced, i.e. integrated into the genome of the target cell and ultimately expressed by said cell.

Several of the proteins required to assemble pseudotyped lentiviral vector particles are detrimental to mammalian cells when they are overexpressed. Thus, for the stable production of pseudotyped lentiviral vectors particles, 293-based cell lines allowing conditional production of virus-encoded proteins using tetracycline regulated promoters were generated (for example see Xu et al., 2001). In one embodiment, the packaging cell used for producing the pseudotyped lentiviral vector particles of the present invention is HEK-293T.

The "psi" element referred to above designates a packaging signal, which leads to the incorporation (the "packaging") of the RNA transcribed from the expression vector into the vector particles during the assembly of the vector particles. Thus, "psi" designates the retroviral packaging signal that efficiently controls the packaging of the messenger RNA of the expression vector. In order for packaging to occur, the expression vector also has to be flanked by specific long terminal repeat sequences (LTRs), so the transcription of the RNA of the expression vector into DNA and subsequent integration into the genome of the target cell can successfully be accomplished.

Consequently, during assembly of the pseudotyped lentiviral vector particles, neither the RNA of the gag/pol gene nor that of the envelope gene encoding, for example, the MeV F and H proteins is incorporated into the lentiviral vector particles. These genes are only transcribed into RNA by the transcription machinery of the packaging cell and further translated into functional proteins. Contrasting this, the psi-positive expression vector is translated into the corresponding RNA and, due to the presence of the psi element and the LTRs, will be incorporated into the resulting lentiviral vector particles and ultimately transduced into the genome of the host cell.

II. The Lentiviral Vector Particles of the Present Invention
1. Lentiviral Vector Particles The lentiviral vector particles of the present invention are generally produced based on psi-negative lentiviral expression vectors. Unexpectedly, it was found that such lentiviral vector particles pseudotyped with MeV F/H proteins result in a titer that is roughly 100-times higher than the titer of vector particles based on MLV expression vectors pseudotyped with MeV F/H proteins Even though any lentiviral expression vector may be suitably be used according to the present invention, the lentiviral expression vector used for the production of lentiviral vector particles is preferably based on a vector selected from the group consisting of HIV-1, HIV-2, SIVmac, SIVpbj, SIVagm, FIV and EIAV (equine infectious anemia virus). It will be obvious for the skilled person that these lentiviral expression vectors need not comprise the complete genomic information of the respective lentivirus; rather these lentiviral vectors only need to comprise the necessary elements for effective packaging into the resulting lentiviral vector particles (see above).

In a further embodiment, the pseudotyped lentiviral vector particle of the invention is derived from a lentivirus, preferably derived from a lentivirus selected from the group consisting of HIV-1, HIV-2, SIVmac, SIVpbj, SIVagm, FIV and EIAV, and even more preferably, is derived from HIV-1.

2. Pseudotyped Heterologous Lentiviral Vector Particles

For generating the lentiviral vector particles of the present invention, the env gene of the original lentivirus is exchanged with the truncated F and H proteins of a *morbillivirus*, or MeV, which are co-expressed in the packaging cell. Lentiviral vector particles pseudotyped with, for example, MeV F and H proteins, unexpectedly, showed increased titers and transduction efficiencies superior to known vectors, which typically carry the VSV G protein or envelope proteins derived from MLV or GaLV (gibbon ape leukemia virus).

In the following, properties of the Morbilliviridae are described and exemplified using the measles virus (MeV). However, it will be clear to the skilled person that the properties, exemplified for MeV, also generally apply for the Morbilviridae.

As described above, the MeV envelope comprises hemagglutinin (H) and fusion (F) glycoproteins. Whereas the H protein binds to the MeV receptors CD46 and SLAM, the F protein carries a hydrophobic fusion peptide that mediates membrane fusion upon receptor binding of H. MeV H is thought to exist at the viral surface as a tetramer consisting of a dimer of two covalently linked dimers, whereas F is considered to trimerize. Upon synthesis as an inactive precursor F0, the F protein becomes proteolytically activated in the trans-Golgi network by furin to thus yield a large transmembrane F1 and a small F2 fragment. The mechanism of MeV-induced membrane fusion may involve receptor-induced conformational changes in the H and then F proteins, suggesting a dynamic interaction between these two proteins during the transfection process.

In contrast to many other enveloped viruses, MeV fuses its envelope membrane directly with the cellular surface membrane without any requirement for particle endocytosis and pH reduction. This is a particular property of measles virus and the *morbilliviruses*, thus distinguishing themselves from many other enveloped viruses that become endocytosed and will only fuse upon pH drop upon endocytosis. Another important aspect refers to the fact that membrane fusion requires both proteins, F and H. When expressed in absence of H protein the MeV F does not induce cell-cell fusion. Interestingly, the H protein function in membrane fusion is not limited to receptor attachment but H is also specifically involved in supporting F protein in its membrane fusion function. It has been demonstrated that only homologous pairs of MeV F and H proteins are able to trigger membrane fusion (Cattaneo and Rose, 1993; J Virol 67, 1493-1502). H proteins that are perfectly well in receptor recognition are not sufficient for membrane fusion as long as they do not properly interact with F protein. Even an amino acid identity of 97%-99% as given in F and H proteins from different MeV strains may not be sufficient for membrane fusion in certain F/H pairs. It is thus clear, that very specific cooperative interactions exist between F and H to allow membrane fusion to occur. What happens on the molecular level is most likely, that H protein when contacting the receptor undergoes a conformational change that itself induces a conformational change in F protein which then exposes the fusion peptide and induces membrane fusion.

Interestingly, there is some experimental evidence that complex formation of the MeV F and H proteins is distinct from other paramyxoviruses. While the H(N) and F proteins of other paramyxoviruses appear to functionally interact only at the cell surface (to thus prevent fusion in inappropriate cellular compartments after furin cleavage), the MeV H and F proteins have been shown to interact in the ER (Plemper et al., 2001). Thus, MeV must either adopt a different mechanism to prevent premature fusion, or must not require such a strategy at all. The receptor for all Paramyxoviridae having neuraminidase activity is the abundant ganglioside sialic acid receptor. In contrast, the MeV receptors CD46 or SLAM may be less available than sialic acid for early fusion, thus rendering the problem of inappropriate intracellular fusion less pronounced for MeV.

In one embodiment, the invention is directed to a pseudotyped lentiviral vector particle comprising a fusion (F) and a hemagglutinin (H) protein of a *morbillivirus*, wherein the cytoplasmic portions of said F and H proteins are truncated and wherein the truncated cytoplasmic portion of the F protein comprises at least 1 positively charged amino acid residue and the truncated cytoplasmic portion of the H protein is truncated to allow efficient pseudotyping and has fusion support function. Preferably, the *morbillivirus* is a measles virus, or the Edmonston strain of measles virus. In a further preferred embodiment the truncated cytoplasmic portion of the H protein comprises at least 9 consecutive amino acid residues of the C-terminal cytoplasmic portion of the H protein plus an additional methinonine at the N-terminus. In another and even more preferred embodiment, the truncated cytoplasmic portion of the F protein comprises at least 3 consecutive amino acid residues of the N-terminal cytoplasmic portion of the F protein and the truncated cytoplasmic portion of the H protein comprises at least 13 consecutive amino acid residues of the C-terminal cytoplasmic portion of the H protein plus an additional methinonine at the N-terminus, wherein one to four of the N-terminal amino acid residues of said at least 13 consecutive amino acid residues of the C-terminal cytoplasmic portion of the H protein can be replaced by alanine residues. In a further and even more preferred embodiment the truncated F protein is FcΔ24 or FcΔ30 and/or the truncated H protein is selected from the group consisting of HcΔ14, HcΔ15, HcΔ16, HcΔ17, HcΔ18, HcΔ19, HcΔ20, HcΔ21+A and HcΔ24+4A.

The lentiviral vector particles of the present invention as pseudotyped with the *morbillivirus* F and H proteins can thus be used to efficiently transduce cells (or cell lines) that carry at least one of the two MeV receptors, CD46 and SLAM.

In a further embodiment, the lentiviral vector particles of the present invention are capable of transducing cells expressing at least one of CD46 and SLAM. In a preferred embodiment, the lentiviral vector particles of the present invention are capable of transducing cells selected from the group consisting of HT1080, HEK-293T, U-87MG, A301 and A-431.

In a yet further embodiment, the lentiviral vector particles of the present invention are capable of selectively transducing cells expressing SLAM. These particles are thus not capable of transducing cells that are not expressing SLAM. Specifically, this effect is achieved with particles that specifically interact with SLAM but not with CD46. In particular, H protein of measles virus or the Edmonston strain of measles virus contained in said particles interacts specifically with SLAM but not with CD46. This can be achieved by introducing point mutations into the H protein. Such a point mutation can be Y481A. Alternative embodiments relate to H proteins having Y481 replaced with any other amino acid, in particular, with methionine or glutamine, or having mutations at one position selected from F431, V451, Y452, A527, P486, I487, A428, L464, G546, S548, F549 wherein these amino acids are replaced with another amino acid and this mutation prevents or assists in preventing interaction of the H protein with CD46. In addition to the above replacements mutation S548L and F549S may be introduced to further reduce the interaction of the H protein with CD46. Alternatively, replacement of all five consecutive residues 473 to 477 in H protein with alanine may prevent interaction of H protein with CD46. Any of the above cited mutations maybe combined with each other (See: Nakamura et al. (2004) Nat. Biotech. 22 (3) p. 331-336; Nakamura et al. (2005) Nat. Biotech. 23 (2) p. 209-214; Vongpunsawad et al. (2004) J Virol 78 (1) p. 302-313; Masse et al. (2002) J Virol 76 (24) p. 13034-13038; Masse et al. (2004) J Virol 78 (17) p. 9051-9063; Patterson et al. (1999) Virology 256 p. 142-151). Alternatively, the H protein of wildtype measles viruses, as for example the IC-B stain, can be used for pseudotyping of lentiviral vector particles (s. Example 5.3). Such H proteins naturally only recognize SLAM but not CD46 as receptor (Yanagi et al. (2006) Jpn J Infect Dis. 59 (1) p. 1-5).

Surprisingly, it has been found that the ratio between the amount of plasmid encoding the truncated F and H protein, respectively, used for the production of the vector particles has a significant effect on the titers of the resulting vector particles. This means that the ratio of the truncated F and H proteins that are incorporated into the presently disclosed lentiviral vector particles has an actual effect on the resulting titer and thus the transduction efficiency of said vector particles.

In general, an increased amount of plasmid coding for the truncated F protein compared to the amount of plasmid coding for the truncated H protein will lead to both an increased titer and an increased transduction efficiency of the resulting pseudotyped lentiviral vector particle.

Thus, in another embodiment of the invention, the amount of plasmid coding for the truncated F protein used during the production of the lentiviral vector particle is higher than that of the plasmid coding for the truncated H protein. Preferably, the amount of plasmid coding for the truncated F protein used during production is 10-100% higher, is 100-250% higher, is 250-500% higher, is 500-750% higher, is 750-1000% higher, or is more than 1000% higher than the amount of the plasmid for the truncated H protein used for lentiviral vector particle production. In an even more preferred embodiment, the amount of plasmid coding for the truncated F protein is 700% higher than that coding for the truncated H protein.

The amount of plasmid coding for the F and H proteins, which is used for producing the lentiviral vector particle, can be assumed to correspond to the amount of the respective encoded protein incorporated in the resulting lentiviral vector particle in a linear fashion.

Consequently, in a further embodiment of the invention, the amount of truncated F protein in the lentiviral vector particle is higher than the amount of the truncated H protein in the lentiviral vector particle. Preferably the amount of truncated F protein in the lentiviral vector particle is 10-100% higher, is 100-250% higher, is 250-500% higher, is 500-750% higher, is 750-1000% higher or is more than 1000% higher than the amount of truncated H protein in the lentiviral vector particle of the present invention. In an even more preferred embodiment, the amount of truncated F protein in the lentiviral vector particle is 700% higher than that of the truncated H protein.

3. Cell Entry Targeted Lentiviral Vector Particles

The findings of the present invention are also important in generating the targeted lentiviral vector particles having improved selective cell entry over other known vector particles, wherein the derived truncated H protein is a mutated (Hmut) and chimeric protein, further displaying a single chain antibody, a growth factor, or a ligand to a cell surface marker at its ectodomain. Thus, the C-terminus of the truncated H protein is fused to a single chain antibody, a growth factor, or a ligand to a cell surface marker.

Mutation of the MeV H protein generally ablates productive interactions with CD46 and SLAM, respectively. In one embodiment, this mutation is introduced by the point mutations Y481A and R533A of the MeV H protein. In another embodiment, the Hmut protein also includes the mutations S548L and F549S, which lead to a more complete ablation of residual infectivity via CD46. Also, the mutation of the residues V451 and Y529 ablates productive interaction with CD46 and SLAM. Alternative mutations for ablating/preventing interaction of the H protein with CD46 have been described above. All of these mutations, which are introduced into the truncated H proteins (HmutΔX) in order to ablate the natural receptor usage, are located in the ectodomain of the MeV H protein. For preventing interaction of the H protein with SLAM one of the following residues may be replaced with any other amino acid, in particular, alanine: I194, D530, Y553, T531, P554, F552, D505, D507 (See: Vongpunsawad et al. (2004) J Virol 78 (1) p. 302-313); Masse et al. (2004) J Virol 78 (17) p. 9051-9063). Lentiviral vector particles pseudotyped with, for example, FcΔ30 and the mutated H proteins additionally displaying a single chain antibody, a growth factor, or a ligand to a cell surface marker at their ectodomain, no longer enter cells via CD46 and SLAM, but are rather targeted to and enter only those cells displaying the respective corresponding markers at their surface.

In a series of targeting experiments, it was found that presently disclosed lentiviral vector particles pseudotyped with a truncated F protein and a fusion construct of a truncated H protein displaying a single chain antibody, or a ligand to a cell surface marker at its ectodomain, only transduced cells that expressed the respective cell surface marker to the single chain antibody or the ligand. The vector particles thus enter those cells expressing the corresponding marker protein; however, the titers are significantly reduced on cells not expressing these markers. Therefore, cell entry and transduction using the lentiviral vector particles of the present invention was demonstrated to be an efficient and effective means for highly selective gene transfer into specific cells. Thus, in a further embodiment the lentiviral vector particles of the present invention can be used to efficiently and effectively transduce cells. In a preferred embodiment such cells are selected from the group consisting of stem cells, cancerous cells, neural cells, EPC, and CD34+ cells.

In another embodiment, the invention is directed to a pseudotyped lentiviral vector particle according to the invention, wherein the single chain antibody or ligand is directed against or binding to a cluster of differentiation (CD) marker, a tumor antigen exposed on the cell surface, a tyrosine kinase receptor, a chemokine receptor, a G-protein-coupled receptor, an olfactory receptor, a viral protein exposed on the surface of chronically infected cells, a neurotransmitter receptor, a stem cell factor receptor, a growth factor receptor, a nerve growth factor receptor, an epidermal growth factor receptor, a vascular endothelial growth factor receptor, a hepatocyte growth factor receptor, an interleukine receptor and/or a cytokine receptor.

In a preferred embodiment, cell markers of interest include, without being limited thereto, all known cluster of differentiation (CD) markers, as e.g. CD4, CD8, CD19, CD20, CD33, CD34, CD133, tumor antigens exposed on the cell surface, as e.g. mucin-1, surface molecules of cells of the nervous system, as e.g. neurotransmitter receptors, like the dopamine, acetylcholine or GABA receptors, tyrosine kinase receptors, as e.g. EGF-R and VEGFR-2, olfactory receptors, and G-protein-coupled receptors, among these also the chemokine receptors, as well as viral proteins exposed on the surface of chronically infected cells, as e.g. the HIV gp120 protein.

CD4 is a glycoprotein expressed on the surface of T helper cells, regulatory T cells, and dendritic cells. On the T cell surface, CD4 acts as a co-receptor for the T cell receptor (TCR). Specifically, the CD4 amplifies the TCR-generated signal by recruiting the tyrosine kinase lck that is essential for activating numerous molecules involved in the signaling cascade of an activated T cell. CD4 is an integral membrane glycoprotein which is known as the human immunodeficiency virus (HIV) receptor for the infection of human cells. CD4 is also a primary receptor used by HIV-1 to gain entry into host T cells. The HIV-1 virus attaches to CD4 by a particular protein in its viral envelope known as gp120. The binding to CD4 creates a shift in the conformation of the viral gp120 protein allowing HIV-1 to bind to two other cell surface receptors on the host cell (i.e. the chemokine receptors CCR5 and CXCR4). Following a further change in shape of a different viral protein (gp41), the HIV virus inserts a fusion peptide into the host T cell that allows the outer membrane of the virus to fuse with the T-cell membrane. HIV infection leads to a progressive reduction in the number of T cells possessing the CD4 receptor and, therefore, the CD4 count is used as a physiological indicator for assisting physicians in deciding when to initiate medical treatment in HIV-infected patients. Thus, CD4-targeted drugs as, inter alia, the cell entry targeted lentiviral vector particles of the present invention, are useful in HIV therapy. In a further embodiment, CD4-targeted lentiviral vector particles of the invention can be used to detect, select and/or isolate CD4+ cells or cell populations.

CD8 is expressed on the cellular surface of T lymphocyte subset, which have two broadly defined functions: (1) class I major histocompatiblity complex (MHC)-restricted cytotoxicity against virally-infected, allogeneic, and other cellular targets; and (2) immunoregulation of other lymphocytes. CD8 is a glycoprotein that serves as a co-receptor which is expressed on the surface of cytotoxic T cells. CD8 consists of an αand a β chain, which both resemble an immunoglobulin-like domain that is connected to the membrane by a thin stalk. CD8 is expresses an affinity for the α3 portion of the Class I MHC molecule, which keeps the cytotoxic T cell and the target cell bound closely together during antigen-specific activation. Cytotoxic T cells having the CD8 surface protein are termed "CD8+ T cells". In a further embodiment, CD8-targeted lentiviral vector particles of the invention can be used to detect, select and/or isolate CD8+ cells or cell populations.

The CD19 protein is expressed on the surface of all B-lymphoid cells, with the exception of terminally differentiated plasma cells, and has been implicated as a signal-transducing receptor in the control of cellular proliferation and differentiation. CD19 is physically associated with the src protooncogene family protein-tyrosine kinase Lyn; the membrane-associated CD19-Lyn receptor-enzyme complex plays a pivotal role for the survival and clonogenicity of B-cell precursors derived from acute lymphoblastic leukemia patients. Thus, CD19-targeted drugs, including the cell entry targeted lentiviral vector particles of the present invention, are useful in acute lymphoblastic leukemia therapy applications. In a further embodiment, CD19-targeted lentiviral vector particles of the invention can be used to detect, transduce, select and/or isolate CD19+ cells or cell populations.

CD20 is the first human differentiation antigen and was initially detected on the surface of human cells by use of monoclonal antibodies. CD20 is a membrane-bound, unglycosylated phosphoprotein expressed on the surface of mature B cells and also B cell precursors, but is absent on both stem cells and pre-pre B cells. Upon differentiation of a B cell to an antibody-producing plasma cell, CD20 expression is lost. CD20 is thought to play a pivotal role in the regulation of growth, differentiation and proliferation of activated B lymphocytes. Thus, CD20-targeted drugs, including the cell entry targeted lentiviral vector particles of the present invention, are useful in therapeutic strategies for cancer. In a further embodiment, CD20-targeted lentiviral vector particles of the invention can be used to detect, transduce, select and/or isolate CD20+ cells or cell populations.

CD33 is a myeloid cell surface antigen that is expressed on blast cells in acute myeloid leukemia in a majority of patients, regardless of age or subtype of the disease. This antigen is also expressed on leukemic stem cells in many cases; however, CD33 is not expressed on normal hematopoietic stem cells. Thus, CD33-targeted drugs, including the cell entry targeted lentiviral vector particles of the present invention, are suitable for use in acute myeloid leukemia therapies.

In a further embodiment, CD33-targeted lentiviral vector particles of the invention can be used to detect, transduce, select and/or isolate CD33+ cells or cell populations.

Bone marrow and peripheral blood of adults typically comprise a sub-type of progenitor cells that are capable of differentiating into mature endothelial cells, and thus contributing to processes of re-endothelialization and neo-vascularization. Since these angiogenic cells have the properties of embryonal angioblasts, they are known as endothelial progenitor cells (EPCs). In general, three surface markers (CD34, CD133 and the vascular endothelial growth factor receptor-2 [VEGFR-2]) characterize the early functional angioblast, located predominantly in the bone marrow. Upon migration to the systemic circulation, EPCs gradually lose their progenitor properties and start to express endothelial markers, such as VE-cadherin, endothelial nitric oxide synthase and von Willebrand factor. Thus, CD34, CD133 and/or VEGFR-2 drugs include the cell entry targeted lentiviral vector particles of the present invention, which are useful for transducing EPCs. In a further embodiment, CD34-, CD133- and/or VEGFR-2-targeted lentiviral vector particles of the invention can be used to detect, transduce, select and/or isolate CD34+, CD133+ and/or VEGFR-2+, respectively cells or cell populations.

The CD133 antigen is a five transmembrane domain glycoprotein (5-TM) that was initially shown to be expressed on primitive cell populations, including CD34 hematopoietic stem and progenitor cells, and other primitive cells such as retina and retinoblastoma and developing epithelium. The CD133 antigen belongs to a newly characterized molecular family of 5-TM proteins. No natural ligand has yet been demonstrated for the CD133 molecule, and its precise function in hematopoietic tissue remains unknown. CD133 may provide an alternative to CD34 for hematopoietic stem cell selection and ex vivo expansion. CD34 has been found on a small fraction of human bone marrow cells. The CD34+-enriched cell population from marrow or mobilized peripheral blood appears responsible for most of the hematopoietic activity. CD34 has therefore been considered to be the most critical marker for hematopoietic stem cells (HSCs). A CD133+ enriched subset can be expanded in a similar manner as a CD34+ enriched subset, retaining its multilineage capacity. Thus, CD34- and CD133-targeted drugs, including the cell entry targeted lentiviral vector particles of the present invention, are suitable for use in transducing these various types of hematopoietic stem and other related types of progenitor cells.

CD34 and stem cell factor (SCF) receptor (c-Kit) are selectively expressed on the cell surface of hematopoietic stem cells (HSC). HSC are multipotent cells that give rise to more HSC and all formed elements in the blood. In a first differentiation step progenitor cells are formed. These are cells that may be multipotent, oligopotent, or unipotent, and they lack significant self-renewal capacity. HSC are entirely responsible for the development, maintenance, and regeneration of blood forming tissues for life. Furthermore, HSC are the most important, if not the only, cells required to engraft in hematopoietic tissue transplants. The hematopoietic system is arguably the best characterized among all of the tissues of the human body owing to its unique biological properties, which have allowed both experimental manipulation in preclinical studies and its transplantation into patients who have undergone purposeful ablation of their hematopoietic organ. For isolation, a number of different cell surface markers have been described for murine and human HSC. For clinical applications CD34 is most often used as marker for HSC purification. In a further embodiment, CD34-targeted lentiviral vector particles of the invention can be used for HSC purification.

Bone marrow and peripheral blood of adults contain a sub-type of progenitor cells capable of differentiating into mature endothelial cells and thus contributing to processes of re-endothelialization and neo-vascularization. Since these angiogenic cells have properties of embryonal angioblasts they were thus termed endothelial progenitor cells (EPCs). In general, three surface markers (CD34, CD133 and the vascular endothelial growth factor receptor-2 [VEGFR-2]) characterize the early functional angioblast, located predominantly in the bone marrow. Upon migration to the systemic circulation EPCs gradually lose their progenitor properties and start to express endothelial marker like VE-cadherin, endothelial nitric oxide synthase and von Willebrand factor. Thus, CD34, CD133 and/or VEGFR-2 drugs as, inter alia, the cell entry targeted lentiviral vector particles of the present invention are useful for transducing EPCs.

G-protein-coupled receptors (GPCRs) are the largest family of plasma membrane receptors. Upon binding its agonist, a GPCR activates an intracellular heterotrimeric guanine nucleotide regulatory protein (G protein). The activated G protein modulates the activity of one or more enzymes or ion channels. GPCRs have in common a seven transmembrane topology and the functional interactions with G proteins. Over 200 GPCRs, responsive to a large variety of stimuli from photons, ions, amino acids and small organic molecules to peptide and protein hormones, have been identified in the human genome. Several hundred more GPCRs (called orphan GPCRs) for as yet unknown ligands have been identified based on homology to the known GPCRs. GPCRs as a group constitute the largest family of targets for pharmacological intervention. They are critically involved in virtually every physiological system. A partial list of natural GPCR ligands includes glutamate, calcium, GABA, acetylcholine, histamine, GTP/ATP, adenosine, cAMP, melatonin, epinephrine, seratonin and dopamine. Peptide hormone GPCR activators include angiotensin, vasopressin, bradykinin, calcitonin, FSH, glucagon, somatostatin and a host of chemokines, pheromones, opioids and cannibinoids. Olfactory and gustatory sensory transduction involves GPCRs responsive to a large array of odorants, and vision depends on the light-activated ligand retinal covalently bound to its own GPCR rhodopsin. Selective gene transfer targeting via many of these receptors that show a very restricted expression pattern, as e.g. the GABAα6 receptor in cerebellar granule cells or the dopamine receptors in the substantia nigra, is of high relevance for pharmacological intervention and for basic research. In a further embodiment, lentiviral vector particles of the invention targeted to G-protein-coupled receptors can be used to detect, transduce, select and/or isolate GPCR bearing cells or cell populations.

Chemokine receptors are members of the G-protein coupled receptor (GPCR) superfamily. At the latest count well over 600 members of this GPCR superfamily have been identified and classified into families. Six CXC, ten CC and one CX3C and XC chemokine receptors have been cloned so far. Receptor binding initiates a cascade of intracellular events mediated by the receptor-associated heterotrimeric G-proteins. These G-protein subunits trigger various effector enzymes that lead to the activation not only of chemotaxis but also to a wide range of functions in different leukocytes such as an increase in the respiratory burst, degranulation, phagocytosis and lipid mediator synthesis. In a further embodiment, lentiviral vector particles of the invention targeted to chemokine receptors can be used to detect, transduce, select and/or isolate chemokine receptor bearing cells or cell populations Receptor tyrosine kinases (RTKs) are a family of membrane proteins which bind extracellular ligands like insulin and growth factors (e.g. platelet derived growth factor receptor, epidermal growth factor receptor). After binding of the ligand, the intracellular domain of the receptor catalyzes autophosphorylation and phosphorylation of specific substrates on tyrosine residues. The following subfamilies of RTK are important: The family of epidermal growth factor (EGF) receptors, the family of vascular endothelial growth factor (VEGF) receptors, the family of hepatocyte growth factor (HGF) receptors, the family of platelet derived growth factor receptors (PDGF), the family of nerve growth factors (NGF) receptors, and the family of fibroblast growth factor (FGF) receptors. Some of these receptors are involved in pathogenesis of tumorigenic diseases, as e.g. the EGF family receptors which can be overexpressed in certain cancer types as e.g. breast cancer. Pseudotyped vectors of this invention can thus be targeting to cancer cells via the EGF receptors using EGF receptor directed single chain antibodies or EGF as a ligand. In a further embodiment, lentiviral vector particles of the invention targeted to RTKs can be used to detect, transduce, select and/or isolate RTK bearing cells or cell populations.

In another preferred embodiment the MeV H protein is selected from the group consisting of a fusion protein of HmutΔ14, HmutΔ15, HmutΔ16, HmutΔ17, HmutΔ18, HmutΔ19, HmutΔ20, HmutΔ21+A or HmutΔ24+4A, and a single chain antibody or a ligand to a cell surface marker at its ectodomain, wherein the single chain antibody is selected from the group consisting of an antibody or a ligand directed against or binding CD4, CD8, CD34, CD20, CD19, CD33, CD133, EGF-R and VEGFR-2 (vascular endothelial growth factor receptor 2). The MeV F protein can be, for example, FcΔ30 or FcΔ24.

Ligands can be growth factors as, inter alia, stem cell factor (SCF), nerve growth factor (NGF), epidermal growth factor (EGF), vascular endothelial growth factor (VEGF), and hepatocyte growth factor (HGF); cytokines, as e.g. erythropoietin, growth hormone, and all types of interleukins; CC and CXC chemokines; and they can be polypeptide and peptide hormones.

In another embodiment, the H protein is a fusion of HmutΔ18, HmutΔ19 or HmutΔ24+4A and a single chain antibody or a ligand to a cell surface marker at its ectodomain.

In another embodiment, the single chain antibody is directed against the cell markers CD20 (scFvCD20), CD34 (scFvCD34), VEGFR-2 (scFvA7), CD133 (scFvCD133), or the ligand is EGF (the ligand of the EGF-receptor).

In yet another embodiment, the H protein is a fusion of HmutΔ18, HmutΔ19 or HmutΔ24+4A fused to scFvCD20, scFvCD34, scFvA7, EGF or scFvCD133 and the F protein is FcΔ30 or FcΔ24. In another preferred embodiment the truncated H protein is defined by the amino acid sequence set forth in SEQ ID NO: 2 or SEQ ID NO: 4.

In a further embodiment, the invention is directed to a nucleic acid molecule, wherein the nucleic acid molecule is defined by the nucleic acid sequence set forth in SEQ ID NO: 1 or SEQ ID NO. 3. Preferably, said nucleic acid molecule is part of a plasmid or expression plasmid.

In a further preferred embodiment, the lentiviral vector particle of the invention further comprises a psi-positive RNA expression vector. Preferably, the psi-positive RNA expression vector comprises at least one gene selected from the group consisting of a selectable marker gene, a gene encoding a fluorescent protein, a gene encoding an antibiotic resistance gene, a gene encoding siRNA, a gene encoding shRNA, a gene encoding an angiogenic factor, a gene encoding an apoptotic factor, a gene encoding a cytotoxic factor, a gene encoding an anti-apoptotic factor, a gene encoding a neuro-protective factor, a gene encoding a viral or bacterial antigen, a gene encoding an anti-viral protein, a gene encoding a tumoral antigen, a gene encoding an immune-stimulatory factor, and a functional copy of a defective or mutated gene in a patient suffering from an inherited disease. In an even more preferred embodiment, said gene is selected from the group consisting of a gene coding for GFP, a gene coding for eGFP, a gene coding for an apoptosis-inducing protein, a gene coding for a cytotoxic protein, TNF-α gene, p53 gene, an interfering RNA, an interferon gene, and a gene coding for an immune stimulatory protein.

In a further embodiment, the invention is directed to methods for producing the lentiviral vector particles of the invention.

Specifically, in another embodiment, the invention is directed to a method for producing a pseudotyped lentiviral vector particle, the method comprising: co-transfecting of a packaging cell line with a psi-negative lentiviral gag/pol gene, a psi-positive lentiviral expression vector and one or two psi-negative expression vector(s) encoding for truncated *morbillivirus* H and F proteins, wherein the truncated cytoplasmic portion of the F protein comprises at least 1 positively charged amino acid residue and the truncated cytoplasmic portion of the H protein is truncated to allow efficient pseudotyping and has fusion support function. Preferably, the *morbillivirus* is a measles virus, or the Edmonston strain of measles virus.

In a further preferred embodiment, the truncated cytoplasmic portion of the H protein comprises at least 9 consecutive amino acid residues of the C-terminal cytoplasmic portion of the H protein plus an additional methinonine at the N-terminus; in an even more preferred embodiment, the truncated cytoplasmic portion of the F protein comprises at least 3 consecutive amino acid residues of the N-terminal cytoplasmic portion of the F protein and the truncated cytoplasmic portion of the H protein comprises at least 13 consecutive amino acid residues of the C-terminal cytoplasmic portion of the H protein plus an additional methinonine at the N-terminus, wherein one to four of the N-terminal amino acid residues of said at least 13 consecutive amino acid residues of the C-terminal cytoplasmic portion of the H protein can be replaced by alanine residues.

In another preferred embodiment, the psi-positive lentiviral expression vector and/or the psi-negative lentiviral gag/pol gene are derived from a lentivirus selected from the group consisting of HIV-1, HIV-2, SIVmac, SIVpbj, SIVagm, FIV and EIAV.

In another preferred embodiment, the one or two psi-negative expression vector(s) encode the truncated F protein FcΔ24 or FcΔ30 and/or encode the truncated H protein selected from the group consisting of HcΔ14, HcΔ15, HcΔ16, HcΔ17, HcΔ18, HcΔ19, HcΔ20, HcΔ21+A and HcΔ24+4A.

In another preferred embodiment, the psi-negative expression vector encoding the truncated H protein encodes a H protein that is a chimeric protein which does not interact with CD46 or SLAM and further has a single chain antibody, a growth factor or a ligand to a cell surface marker at its ectodomain.

In another preferred embodiment, the single chain antibody or ligand is directed against or binding to a cluster of differentiation (CD) marker, a tumor antigen exposed on the cell surface, a tyrosine kinase receptor, a chemokine receptor, a G-protein-coupled receptors, an olfactory receptor, a viral proteins exposed on the surface of chronically infected cells, a neurotransmitter receptor, a stem cell factor, a growth factor, a nerve growth factor, an epidermal growth factor, a vascular endothelial growth factor, a hepatocyte growth factor, an interleukine receptor and/or a cytokine receptor. Even more preferably, the single chain antibody or ligand is directed against or binding a molecule selected from the group consisting of CD4, CD8, CD34, CD20, CD19, CD33, CD133, EGF-R and VEGFR-2, mucin-1, the dopamine receptor, the acetylcholine receptor, the GABA receptor, EGF-R, VEGFR-2, the HIV gp120 protein, (HGF) and erythropoietin. Even more preferably, the truncated H protein is defined by the amino acid sequence set forth in SEQ ID NO: 2 or SEQ ID NO: 4.

In another preferred embodiment, the psi-positive lentiviral expression vector comprises at least one gene selected from the group consisting of a selectable marker gene, a gene encoding a fluorescent protein, a gene encoding an antibiotic resistance gene, a gene encoding siRNA, a gene encoding shRNA, a gene encoding an angiogenic factor, a gene encoding an apoptotic factor, a gene encoding a cytotoxic factor, a gene encoding an anti-apoptotic factor, a gene encoding a neuro-protective factor, a gene encoding a viral or bacterial antigen, a gene encoding an anti-viral protein, a gene encoding a tumoral antigen, a gene encoding an immune-stimulatory factor, and a functional copy of a defective or mutated gene in a patient suffering from an inherited disease. Preferably, the gene is selected from the group consisting of GFP, eGFP, apoptosis-inducing protein or a gene coding for a cytotoxic protein, including as, inter alia, the TNF-α gene, the p53 gene, an interfering RNA, an interferon gene, and a gene coding for an immune stimulatory protein.

In another preferred embodiment, the packaging cell line stably expresses one or more of the genes encoded by psi-negative lentiviral gag/pol gene, psi-positive lentiviral expression vector or one or two psi-negative expression vector(s) encoding for truncated measles virus H and F proteins.

In another preferred embodiment, the amount of plasmid encoding the truncated F protein used for co-transfection during production of the pseudotyped lentiviral vector particles is higher than the amount of plasmid encoding the truncated H protein used for co-transfection. Preferably, the amount of plasmid encoding the truncated F protein is 10-100% higher, is 100-250% higher, is 250-500% higher, is 500-750% higher, is 750-1000% higher, is more than 1000% higher and most preferably is 700% higher than the amount of plasmid encoding the truncated H protein.

To summarize, the present invention is based on the unexpected and surprising finding that the incorporation of *morbillivirus*, preferably MeV, F and H proteins having truncated cytoplasmic tails into lentiviral vector particles, and the complex interaction of these two proteins during cellular fusion, allows for a superior and more effective transduction of cells. Moreover, these pseudotyped vector particles allow the targeted gene transfer into a given cell type of interest by modifying a mutated and truncated H protein with a single-chain antibody or ligand directed against a cell surface marker of the target cell.

III. Pharmaceutical Compositions Based on the Lentiviral Vector Particles of the Present Invention 1. Formulations and Routes of Administration Pharmaceutical compositions based on the lentiviral vector particles of the present invention can be formulated in any conventional manner using one or more physiologically acceptable carriers or excipients. Thus, the lentiviral vector particles of the present invention may be formulated for administration by, for example, injection, inhalation or insulation (either through the mouth or the nose) or by oral, buccal, parenteral or rectal administration.

The pharmaceutical compositions of the present invention can be formulated for a variety of modes of administration, including systemic, topical or localized administration. Techniques and formulations can be found in, for example, Remington's Pharmaceutical Sciences, Meade Publishing Co., Easton, Pa. For systemic administration, injection is preferred, including intramuscular, intravenous, intraperitoneal, and subcutaneous. For the purposes of injection, the pharmaceutical compositions of the present invention can be formulated in liquid solutions, preferably in physiologically compatible buffers, such as Hank's solution or Ringer's solution. In addition, the pharmaceutical compositions may be formulated in solid form and redissolved or suspended immediately prior to use. Lyophilized forms of the pharmaceutical composition are also suitable.

For oral administration, the pharmaceutical compositions of the present invention may take the form of, for example, tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycolate); or wetting agents (e.g. sodium lauryl sulfate). The tablets can also be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. ationd oil, oily esters, ethyl alcohol or fractionated vegetable oils); and preservatives (e.g. methyl or propyl-p-hydroxybenzoates or sorbic acid). The preparations can also contain buffer salts, flavoring, coloring and sweetening agents as appropriate.

The pharmaceutical compositions can be formulated for parenteral administration by injection, e.g. by bolus injection or continuous infusion. Formulations for injection can be presented in a unit dosage form, e.g. in ampoules or in multi-dose containers, with an optionally added preservative. The pharmaceutical compositions can further be formulated as suspensions, solutions or emulsions in oily or aqueous vehicles, and may contain other agents including suspending, stabilizing and/or dispersing agents.

Additionally, the pharmaceutical compositions can also be formulated as a depot preparation. These long acting formulations can be administered by implantation (e.g. subcutaneously or intramuscularly) or by intramuscular injection. Thus, for example, the compounds may be formulated with suitable polymeric or hydrophobic materials (e.g. as an emulsion in an acceptable oil) or ion exchange resins, or as sparingly soluble derivatives, for example, as a sparingly soluble salt. Other suitable delivery systems include microspheres, which offer the possibility of local noninvasive delivery of drugs over an extended period of time. This technology can include microspheres having a precapillary size, which can be injected via a coronary catheter into any selected part of an organ without causing inflammation or ischemia. The administered therapeutic is then slowly released from the microspheres and absorbed by the surrounding cells present in the selected tissue.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts, and fusidic acid derivatives. In addition, detergents may be used to facilitate permeation. Transmucosal administration can occur using nasal sprays or suppositories. For topical administration, the vector particles of the invention can be formulated into ointments, salves, gels, or creams as generally known in the art. A wash solution can also be used locally to treat an injury or inflammation in order to accelerate healing.

In a further embodiment, the invention is directed to a pharmaceutical composition comprising the pseudotyped vector particles of the present invention, or the use of the pseudotyped vector particles of the present invention for the preparation of a medicament. Preferably, the pharmaceutical composition further comprises a pharmaceutically acceptable carrier or excipient.

2. Use of the Pharmaceutical Compositions

The pharmaceutical compositions based on the pseudotyped cell entry targeted vector particles of the present invention are useful for transducing a specifically targeted cell, which can include, inter alia, a cancerous cell or a stem cell, with the gene product of a desired protein that, if expressed in the targeted cell, leads to the prevention or the treatment of a particular medical condition.

As an example, CD133 has recently been shown to be an important cell marker appearing on cancer cells. Thus, for example, a kidney (renal) carcinoma cell that expresses CD133 can be readily targeted by the pseudotyped cell entry targeted vector particles of the present invention, wherein the H protein is fused to a single chain antibody directed to CD133 (scFvCD133). Furthermore, the gene to be transduced into the targeted renal carcinoma cells can be, for example, a gene encoding a desired antibody gene (or fragment thereof). Thus, the transgene expression product can bind the intracellular proteins, e.g., those derived from oncogenes, to thereby down-regulate oncogenic protein expression. Furthermore, the gene to be transduced into the targeted renal carcinoma cells can encode an apoptosis-inducing protein or a cytotoxic protein, including as, inter alia, TNF-α, p53an interfering RNA, interferon, an immune stimulatory protein, and/or a gene coding for cytostatic, apoptosis-inducing and/or cytotoxic gene products.

In another embodiment, the pseudotyped vector particle used for the preparation of a medicament comprises a gene selected from the group consisting of a selectable marker gene, a gene encoding a fluorescent protein, a gene encoding an antibiotic resistance gene, a gene encoding siRNA, a gene encoding shRNA, a gene encoding an angiogenic factor, a gene encoding an apoptotic factor, a gene encoding a cytotoxic factor, a gene encoding an anti-apoptotic factor, a gene encoding a neuro-protective factor, a gene encoding a viral or bacterial antigen, a gene encoding an anti-viral protein, a gene encoding a tumoral antigen, a gene encoding an immune-stimulatory factor, a functional copy of a defective or mutated gene in a patient suffering from an inherited disease, a gene coding for a cytotoxic protein, including as, inter alia, TNF-α, p53an interfering RNA, interferon, an immune stimulatory protein, and/or a gene coding for cytostatic, apoptosis-inducing and/or cytotoxic gene products, wherein the gene is to be transduced into and expressed by the targeted cell.

A significant advantage of the pharmaceutical compositions based on the vector particles of the present invention is that, due to their high specificity for a particular targeted cell, the amount of the pharmaceutical composition that needs to be administered to the patient can thus be provided in a tailored amount. For example, in cancer therapies, a pharmaceutical composition based on vector particles comprising a gene coding for cytostatic, apoptosis-inducing and/or cytotoxic gene products can thus be administered systemically to the patient and, due to the high specificity of the vector particles, the concentration of the pharmaceutical composition at the site of the targeted cells, e.g. the treated tumor, is as high or even higher than in a situation where the cytostatic, apoptosis-inducing and/or cytotoxic gene products are directly administered in a systemic fashion. Thus, the amount of the pharmaceutical composition of the invention resulting in the formation of cytostatic, apoptosis-inducing and/or cytotoxic gene products at the site of treatment can be maintained at a level significantly lower than if the cytostatic, apoptosis-inducing and/or cytotoxic gene products were to be administered directly and systemically. As can be seen, the possibility of severe and adverse effects of the cytostatic, apoptosis-inducing and/or cytotoxic gene products can be significantly decreased or even prevented.

In a further embodiment the invention is directed to the use of the vector particles of the invention for the preparation of a medicament for the treatment or prevention of cancer, including, but not limited to, neoplasms, tumors, metastases, or any disease or disorder characterized by uncontrolled cell growth, and particularly multidrug resistant forms thereof. Examples of types of cancer and proliferative disorders to be treated with the therapeutics of the invention include, but are not limited to, leukemia (e.g. myeloblastic, promyelocytic, myelomonocytic, monocytic, erythroleukemia, chronic myelocytic (granulocytic) leukemia, and chronic lymphocytic leukemia), lymphoma (e.g. Hodgkin's disease and non-Hodgkin's disease), fibrosarcoma, myxosarcoma, liposarcoma, chondrosarcoma, osteogenic sarcoma, angiosarcoma, endotheliosarcoma, Ewing's tumor, colon carcinoma, pancreatic cancer, breast cancer, ovarian cancer, prostate cancer, squamous cell carcinoma, basal cell carcinoma, adenocarcinoma, renal cell carcinoma, hepatoma, Wilms' tumor, cervical cancer, uterine cancer, testicular tumor, lung carcinoma, small cell lung carcinoma, bladder carcinoma, epithelial carcinoma, glioma, astrocytoma, oligodendroglioma, melanoma, neuroblastoma, retinoblastoma, dysplasia and hyperplasia. In a particular embodiment, therapeutic compounds of the invention are administered to patients having prostate cancer (e.g., prostatitis, benign prostatic hypertrophy, benign prostatic hyperplasia (BPH), prostatic paraganglioma, prostate adenocarcinoma, prostatic intraepithelial neoplasia, prostato-rectal fistulas, and atypical prostatic stromal lesions). The treatment and/or prevention of cancer includes, but is not limited to, alleviating symptoms associated with cancer, the inhibition of the progression of cancer, the promotion of the regression of cancer, and the promotion of the immune response.

The pharmaceutical compositions of the present invention can be administered alone or in combination with other types of cancer treatment strategies (e.g., radiation therapy, chemotherapy, hormonal therapy, immunotherapy and anti-tumor agents). Examples of anti-tumor agents include, but are not limited to, cisplatin, ifosfamide, paclitaxel, taxanes, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, and taxol.

In a further embodiment, the invention is directed to the use of the presently disclosed pseudotyped vector particles for the preparation of a medicament. In another embodiment, the invention is directed to the use of the pseudotyped vector particles of the invention for the preparation of a medicament for the treatment or prevention of at least one condition in a subject, wherein the condition is selected from the group consisting of a chronical infection, an inherited monogenetic disease, a cardiovascular disease, a neurodegenerative disease, cancer, HIV, Alzheimer disease, Parkinson disease, diabetes, a neuroinflammatory disease, a rheumatic disease, an autoimmune disease, adipositas, acute lymphoblastic leukemia, myeloid leukemia, renal carcinoma, and disorders related to endothelialization or re-endothelialization. In yet another embodiment, the cancer is selected from the group consisting of leukemia, myeloblastic, promyelocytic, myelomonocytic, monocytic, erythroleukemia, chronic myelocytic (granulocytic) leukemia, and chronic lymphocytic leukemia, lymphoma, e.g. Hodgkin's disease and non-Hodgkin's disease, fibrosarcoma, myxosarcoma, liposarcoma, chondrosarcoma, osteogenic sarcoma, angiosarcoma, endotheliosarcoma, Ewing's tumor, colon carcinoma, pancreatic cancer, breast cancer, ovarian cancer, prostate cancer, squamous cell carcinoma, basal cell carcinoma, adenocarcinoma, renal cell carcinoma, hepatoma, Wilms' tumor, cervical cancer, uterine cancer, testicular tumor, lung carcinoma, small cell lung carcinoma, bladder carcinoma, epithelial carcinoma, glioma, astrocytoma, oligodendroglioma, melanoma, neuroblastoma, retinoblastoma, dysplasia and hyperplasia, prostate cancer, prostatitis, benign prostatic hypertrophy, benign prostatic hyperplasia (BPH), prostatic paraganglioma, prostate adenocarcinoma, prostatic intraepithelial neoplasia, prostato-rectal fistulas, and atypical prostatic stromal lesions.

Other medical conditions that can be treated with the pseudotyped lentiviral vector of this invention refer to all types of diseases being related to the hematopietic system. In this case the pseudotyped vector can be used for selective gene transfer into hematopoietic stem cells (HSC) or precursor cells. For selective gene transfer into HSC stem cell factor (SCF) or a single chain antibody directed against CD34 is displayed on the H protein. With such vectors the therapeutic gene can be transferred and stably inserted into the genome of HSC so that it will be present and expressed in any cell type that differentiated from the transduced HSC. For transduction bone marrow cells or leukapheresis cells can be used without the need for purification of HSC, which is necessary when conventional non-targeted retroviral vectors are being used. Alternatively, with these targeted vectors an in vivo application into the patient's bone marrow is possible. Types of diseases that can be treated by this approach include, but are not limited to, monogenetic inherited diseases, like immunodeficiencies as e.g. SCID-X1. In SCID-X1, the pseudotyped vector will transfer the γc-interleukin-receptor gene which is mutated in the patients. Moreover, also infectious diseases like AIDS can be treated this way. Then, anti-viral genes encoding e.g. HIV specific inhibitory RNA (RNAi), or cell entry inhibitors like membrane bound T20, will be packaged into the pseudotyped vector. Alternatively, an AIDS directed gene transfer can be performed when antibodies specific for the HIV gp120 protein which is exposed on the cell surface of HIV infected cells, is displayed on the vector particles. Packaged with suicide genes, such vectors selectively kill HIV infected cells when being systemically delivered into patients.

The liver is a very suited organ for the production of soluble factors of the blood. In hemophilia patients, clotting factors like factor VIII or factor IX are enzymatically inactive due to mutations in the corresponding genes, resulting in blood clotting failure and frequent bleedings. A gene therapy approach against hemophilia requires an efficient transfer of a functional copy of the defective gene into the liver of hemophilia patients. This can be achieved using a pseudotyped lentiviral vector, in which the H protein displays a single chain antibody directed against a liver cell surface marker, as e.g. the hepatocyte growth factor receptor or the asialoglycoprotein receptor. Such a vector can then be equipped with a functional copy of the factor VIII or factor IX gene and delivered into hemophilia patients via the liver portal vein. Likewise, the liver can be used for immunoglobuline production by such an approach, if the genetic information for a particular immunoglobuline, e.g. directed against an infectious agent, is packaged into the pseudotyped vector.

Dendritic cells are antigen-presenting cells that is cells capable of retaining antigen-antibody complexes for an extended period of time, which are involved in immune defense of the body. Dendritic cells differentiate from monocytes. Especially for vaccination strategies against cancer dendritic cells are the cell type of choice for the expression of tumor antigens. In vivo gene transfer of these cells can be achieved with a pseudotyped lentiviral vector displaying a single chain antibody directed against CD14 (for monocytes) or CD83 (for dendritic cells). Lentiviral vectors of the type SIVpbj or HIV-2 are used for this application as they allow efficient transfer of the tumor antigen encoding vector into resting monocytes.

The unique properties of the pseudotyped lentiviral vectors of this invention, i.e. gene delivery into resting cells and cell entry targeted delivery, will be of special importance for the treatment of many types of neurodegenerative diseases that require the delivery of genes encoding anti-apoptotic or neuro-protective factors into defined subpopulations of neurons. Parkinson's disease e.g., results from the loss of pigmented dopamine-secreting (dopaminergic) cells and subsequent loss of melanin, secreted by the same cells, in the pars compacta region of the substantia nigra. These neurons project to the striatum and their loss leads to alterations in the activity of the neural circuits within the basal ganglia that regulate movement, in essence an inhibition of the direct pathway and excitation of the indirect pathway. The direct pathway facilitates movement and the indirect pathway inhibits movement, thus the loss of these cells leads to a hypokinetic movement disorder. The lack of dopamine results in increased inhibition of the ventral lateral nucleus of the thalamus, which sends excitatory projections to the motor cortex, thus leading to hypokinesia. For treatment, the pseudotyped lentiviral vector of this invention display a single chain antibody directed against the dopamine receptor and have therapeutic genes coding e.g. for anti-apoptotic or neuro-protective factors packaged. In another embodiment, the lentiviral vector particles of the invention can be used for the gene transfer into cells, preferably resting cells and for gene therapy applications.

Cardiovascular disease refers to the class of diseases that involve the heart and/or blood vessels (arteries and veins). The symptoms and treatments depend on which set (or sets) of arteries are affected. In coronary heart disease, atherosclerotic plaques (inflamed fatty deposits in the blood vessel wall) obstruct the coronary arteries (blood vessels supplying the heart). When the blockages become severe enough, the blood flow to the heart is restricted (cardiac ischemia), especially during increased demand (i.e. during exertion or emotion), resulting in angina pectoris. Myocardial infarction occurs when one of the plaques ruptures, forming a thrombus (blood clot) that acutely occludes the whole artery. This may result in the death of the patient if the affected area is large enough. In peripheral artery disease, obstruction occurs in the arteries of the arms or legs. This results initially in pain, during temporary obstruction, and finally in tissue death and gangrene if not treated. There are many specific illnesses that may occur in association with these and other cardiovascular disease. In addition to the ones mentioned above, these include hypertension (high blood pressure), arterial aneurysms (arterial enlargement and weakening), cardiomegaly (abnormal enlargement of the heart), tachycardia/bradycardia/arrhythmia (fast/slow/irregular heart rates), cardiac arrest (heart stoppage), cardiomyopathy (heart muscle weakness), heart valve regurgitation (leakage), and heart valve stenosis (narrowing). The pseudotyped lentiviral vectors of this invention can be used for treatment upon in vivo application to the site of the affected artery. Being targeted to CD133 (endothelial precursor cells) or to VEGF receptor (expressed on activated endothelial cells), the vector selectively transfers therapeutic genes encoding factors which stimulate angiogenesis either directly (e.g. VEGF, FGF) or indirectly (e.g. endothelial nitric-oxide synthase) leading to the development of new blood vessels circumventing the blocked blood flow. In another embodiment, the lentiviral vector particles of the invention can be used for the treatment of cardiovascular diseases.

In a further embodiment, the invention is directed to the use of the pseudotyped vector particles of the invention for the preparation of a medicament. In a preferred embodiment, the invention is directed to the use of the pseudotyped vector particles of the invention for the preparation of a medicament for the treatment or prevention of cancer, chronical infections as e.g. AIDS, inherited monogenetic diseases, cardiovascular disease and neurodegenerative diseases. In a preferred embodiment, the cancer is selected from the group consisting of leukemia, myeloblastic, promyelocytic, myelomonocytic, monocytic, erythroleukemia, chronic myelocytic (granulocytic) leukemia, and chronic lymphocytic leukemia, lymphoma, e.g. Hodgkin's disease and non-Hodgkin's disease, fibrosarcoma, myxosarcoma, liposarcoma, chondrosarcoma, osteogenic sarcoma, angiosarcoma, endotheliosarcoma, Ewing's tumor, colon carcinoma, pancreatic cancer, breast cancer, ovarian cancer, prostate cancer, squamous cell carcinoma, basal cell carcinoma, adenocarcinoma, renal cell carcinoma, hepatoma, Wilms' tumor, cervical cancer, uterine cancer, testicular tumor, lung carcinoma, small cell lung carcinoma, bladder carcinoma, epithelial carcinoma, glioma, astrocytoma, oligodendroglioma, melanoma, neuroblastoma, retinoblastoma, dysplasia and hyperplasia, prostate cancer, prostatitis, benign prostatic hypertrophy, benign prostatic hyperplasia (BPH), prostatic paraganglioma, prostate adenocarcinoma, prostatic intraepithelial neoplasia, prostato-rectal fistulas, and atypical prostatic stromal lesions.

In a further embodiment the pharmaceutical compositions of the present invention are administered alone or in combination with other types of cancer treatment.

IV. Screening for Antibodies Using the Lentiviral Vector Particles of the Present Invention Phage display libraries represent a well-established methodology for the screening of antibodies. They are especially useful for the screening against purified plastic immobilized antigens. However, screening against complete cells or cell membranes is more challenging. For example, screening in living animals is impossible using phage displayed antibodies. Another known limitation of phage libraries is the expression and selection of antibodies in a prokaryotic environment. Therefore, translational problems are known to frequently occur when phage selected antibodies are intended for any kind of therapeutic use.

The present invention further provides a method for a mammalian virus-based screening system, allowing desired antibody selection in a mammalian or human system. More importantly, and in contrast to all known antibody screening platforms, the disclosed system couples antibody-antigen contact directly with infection or gene transfer. Therefore, a single binding event will be sufficient for antibody signal detection.

The scFv mediated targeting of vector particles of the present invention provides such a desired virus-based antibody screening system. By substituting a distinct scFv in the MeV H protein variants by a library of scFv, a library of HIV/MeV vector particles can be produced. The vector particles contained within this library are equipped with a bicistronic transfer vector encoding the scFv-H variant in addition to a selection marker including, for example, neomycin resistance. Thus, vector particles that enter the target cells via an antibody-antigen interaction will stably integrate their genetic information into the cell, which can then be selected and amplified under neomycin conditions. The genetic information for the selected antibody can then be readily cloned from the neomycin-resistant cells.

The presently disclosed library system is more desirable for the screening of antibodies for therapeutic or targeting use than known phage libraries. Furthermore, the design of particular screening methods is more flexible for such therapeutic or targeting use than with phage methodologies.

The present invention thus discloses a method for screening of antibodies in a mammalian system, wherein a library of pseudotyped lentiviral vector particles is provided that comprises a plurality of groups of different pseudotyped lentiviral vector particles, wherein the vector particles each have a truncated F and H protein of the invention. Furthermore, the truncated H protein is typically a chimeric protein that does not interact with CD46 or SLAM, and further contains a single chain antibody at its ectodomain (as explained, supra). In addition, the various groups of different vector particles comprised in the library differ in the single chain antibodies that are fused to the ectodomain of their H protein.

Furthermore, each of the vector particles of a given group of vector particles comprises a bicistronic lentiviral expression vector that encodes (a) for the single chain antibody that is fused to the H protein of the respective group of vector particles and (b) for an expressible reporter gene. This means that every vector particle of a given group carries the genetic information for the antibody that is fused to its truncated H proteins and furthermore, provides a means to transduce the targeted cell with the genetic information of the reporter gene. By "expressible" is meant that upon transduction, the reporter gene will be expressed by the targeted cell, i.e. that the complete genetic information is present that leads to the expression of the reporter gene (inter alia, promoter regions recognized by the targeted cell).

A population of cells expressing a known or unknown marker can be screened using the vector particles of the present library; the pseudotyped lentiviral vector particles will then only transduce those cells expressing a marker on their surface that corresponds to the single chain antibody fused to the truncated H protein that the vector particle is bearing. Consequently, such cells will, upon transduction, carry the genetic information of (a) the single chain antibody that is fused to the H protein of the respective vector particle and (b) the expressible reporter gene. As the expressible reporter gene is then expressed by the transduced cell, the reporter thus serves as a means for selecting those cells that have been transduced and, as a result, harbor the genetic information of the single chain antibody bound to the corresponding marker on the surface of the transduced cell.

As an example, the expressible reporter gene can encode the neomycin resistance gene or other antibiotic resistance genes, but also fluorescent markers, like GFP, eGFP or antibody detectable cell markers, allowing, inter alia, fluorescence activated cells sorting (FACS) of the transduced cells. Thus, in case of the expressible reporter gene encoding neomycin resistance, the transduced cells can then be selected by incubation with neomycin, which will lead to the killing of all non-transduced and thus neomycin susceptible cells. Consequently, only cells will be left that were transduced and thus carry and express the neomycin resistance gene.

In a subsequent step, the genetic content of the single chain antibody of the pseudotyped lentiviral vector particle that transduced the cell, and thus conferred the neomycin resistance, can be determined from the neomycin-resistant cells. This determination is typically done by known sequencing protocols. As an example, primers can be used that correspond to a universal sequence introduced into the library of the pseudotyped lentiviral vector particles, e.g. within the region or the C-terminal portion of the H protein adjacent to the region of fusion of H protein and single chain antibody. As another example, the sequence of a HIS-tag, which was generally added to all the fusion constructs comprising H protein and the single chain antibody of said library, can be used for the generation of such primers.

The population of cells that is screened using the library pseudotyped lentiviral vector particles can express a known cell marker or an unknown cell marker. In case of a known marker, the population of cells can naturally express the cell marker. This is the case if, for example, if screening takes place for a specific cell line or cells derived from a cancer biopsy that are known to express a particular cell marker. In such cases, the screening will be directed to determine novel antibodies to such markers that can exhibit novel and/or improved properties. However, the marker present on the population of cells subjected to the screening of the present invention need not be known. As an example, a cell population derived from the biopsy of an unknown cancer or lesion can be screened using this technique. In such cases, the screening will be directed to determining any novel antibodies that can be used, for example, for the classification and treatment of such cancer or lesion.

The cells subjected to the screening can furthermore express the markers transiently or stably. This means that antibodies for a given and known marker can specifically be screened for. This will be of particular interest for membrane proteins that are difficult to purify and to raise antibodies against by conventional methods. As an example, a mammalian cell line, e.g. a CHO or a HT1080 cell, is stably transfected to express a specific marker, for example, a human CD20 marker. Subsequently, the stably transfected cell line expressing the CD20 is then screened using the library of pseudotyped lentiviral vector particles in order to determine antibodies directed to human CD20. Other cell markers that can be subjected to the screening include, without being limited thereto, all known cluster of differentiation (CD) markers, as e.g. CD4, CD8, CD19, CD20, CD33, CD34, CD133, tumor antigens exposed on the cell surface, as e.g. mucin-1, surface molecules of cells of the nervous system, as e.g. neurotransmitter receptors, like the acetylcholine or GABA receptors, growth factor receptors, as e.g. EGF-R and VEGFR-2, olfactory receptors, and G-protein-coupled receptors as well as viral proteins exposed on the surface of chronically infected cells, as e.g. the HIV gp120 protein.

In a further embodiment, the invention is directed to a method for screening for antibodies in a mammalian system comprising: (a) providing a library of pseudotyped lentiviral vector particles comprising a plurality of different pseudotyped lentiviral vector particles according to the invention, wherein the truncated H proteins of the pseudotyped lentiviral particles have a different single chain antibody at their ectodomain and the particles further comprise a bicistronic lentiviral expression vector, wherein said expression vector encodes for the single chain antibody of the respective pseudotyped lentiviral particle and an expressible reporter gene; (b) contacting a population of cells expressing a cell marker with the library of step (a), under conditions to allow transduction of the cells by said vector particles; (c) selecting cells that express the expressible reporter gene transduced by a pseudotyped lentiviral vector particle of step (a); and (d) determining the genetic information of the single chain antibody of the pseudotyped lentiviral vector particle that transduced the cell from the selected cells of step (c).

In a preferred embodiment the expressible reporter gene is a gene coding for a gene product selected from the group of a selectable marker gene, a gene encoding a fluorescent protein, a gene conferring antibiotic resistance, neomycin, GFP and eGFP.

In another preferred embodiment the population of cells naturally expresses the cell marker, antigen or receptor, or wherein the population of cells has been transiently or stably transfected to express said cell marker, antigen or receptor.

In another preferred embodiment the cell marker, antigen or receptor is selected from the group consisting of CD4, CD8, CD34, CD20, CD19, CD33, CD133, EGF-R and VEGFR-2.

In another preferred embodiment the amount of truncated F protein of the pseudotyped lentiviral vector particles is higher than the amount of truncated H protein, preferably the amount of truncated F protein is 10-100% higher, is 100-250% higher, is 250-500% higher, is 500-750% higher, is 750-1000% higher, is more than 1000% higher and most preferably is 700% higher than the amount of truncated H protein.

V. Detection. Selection and/or Isolation of Specific Cells Using the Lentiviral Vector Particles of the Present Invention The present invention also provides means to select detect and/or isolate cells, which are bearing a specific cell marker.

This is especially desirable if, for example, tissues or cell populations from biopsies are examined for cancerous cells. A further example for the use of the vector particles of the present invention for detection, selection and/or isolation of specific cells in the field of neurobiology is given in the following.

In neurobiology protocols for organotypic slice cultures from mouse brain are well established that allow cultivation of the complete slices for several weeks and analysis of single cells within the tissue, as e.g. electrophysiology recordings. So far no method is available to identify defined types of neurons in the tissue slice under live conditions before the analysis is being performed. The selective marker gene transduction with the pseudotyped lentiviral vectors of this invention can label a single cell based on the expression of a cell surface marker of choice that is used for gene transfer.

Using the lentiviral vector particles of the present invention, for example, AMPA receptor positive neurons can be identified in hippocampal slice cultures. For this purpose a lentiviral pseudotype vector is generated that displays a scFv directed against the glutamate receptor-1 (GluR1) and further having an expression vector comprising the GFP gene. The hippocampal slice cultures can then be inoculated with said lentiviral vector particle and the GFP staining pattern can be observed to identify the AMPA receptor positive neurons.

In a further embodiment, the invention is directed to a method for the detection or selection of cells expressing a specific cell marker, the method comprising: (a) providing a pseudotyped lentiviral vector particle according to the invention, wherein the truncated H protein of the said vector particle has a single chain antibody or ligand for said specific cell marker at its ectodomain and said vector particle further comprises an expression vector, wherein said expression vector encodes for a expressible reporter gene; (b) contacting the pseudotyped lentiviral vector particle of step (a) with at least one cell under conditions to allow transduction of the at least one cell by said vector particle; and (c) detecting or selecting the cell(s) that express the expressible reporter gene.

In a preferred embodiment the expressible reporter gene is a gene coding for a gene product selected from the group of a selectable marker gene, a gene encoding a fluorescent protein, a gene conferring antibiotic resistance, neomycin, GFP and eGFP.

In another preferred embodiment the population of cells naturally expresses the cell marker, antigen or receptor, or wherein the population of cells has been transiently or stably transfected to express said cell marker, antigen or receptor.

In another preferred embodiment the cell marker, antigen or receptor is selected from the group consisting of CD4, CD8, CD34, CD20, CD19, CD33, CD133, EGF-R and VEGFR-2, mucin-1, the dopamine receptor, the acetylcholine receptor, the GABA receptor, EGF-R, VEGFR-2, the HIV gp120 protein, (HGF) and erythropoietin.

In another preferred embodiment the amount of truncated F protein of the pseudotyped lentiviral vector particles is higher than the amount of truncated H protein, preferably the amount of truncated F protein is 10-100% higher, is 100-250% higher, is 250-500% higher, is 500-750% higher, is 750-1000% higher, is more than 1000% higher and most preferably is 700% higher than the amount of truncated H protein.

VI. Identification of an Antigen of an Antibody or the Receptor of a Ligand Using the Lentiviral Vector Particles of the Present Invention The invention further provides means to identify an antigen for a given single chain antibody with unknown specificity or the receptor for a ligand.

For example, a single chain antibody (designated 7A5) has been previously identified by screening a phage display library for binding to the surface of human T-lymphocytes. Although it has been established that its antigen is present on the surface of human T-lymphocytes but absent from other human cell types, among these are HEK-293T cells and HT1080 cells, the identity of the antigen is unknown.

To identify the antigen, pseudotyped lentiviral vectors according to this invention are generated displaying the 7A5 on the H protein. Furthermore, a bicistronic transfer vector encoding a neomycin resistance (neo$^r$) gene and the GFP gene will be used, so that the resulting vector particles will transfer both marker genes into antigen positive cells.

In the next step, a cDNA expression library from human T-lymphocytes packagable in an MLV vector will be used to transduce and express the cDNA library in HT1080 or HEK-293T cells. Methods of preparing cDNA and of constructing cDNA expression libraries are well known in the art, and any such method can be used (see Sambrook et al., 1989). Alternatively, retroviral packagable cDNA libraries from human T-lymphocyte tissue can be purchased from commercial suppliers. The cDNA library transduced cells will then be incubated with the 7A5 pseudotyped lentiviral vector. Those cells expressing the 7A5 antigen in the transduced cell population will become GFP and neor positive. These cells can therefore be selected under neomycin or sorted by fluorescent activated cell sorting. Subsequently the cells are amplified under standard cell culture conditions. Finally, the cDNA expressed in the selected cells can be cloned and sequenced to identify the 7A5 antigen by gene bank search.

In a further embodiment the invention is directed to a method for identifying the antigen of an antibody or the receptor of a ligand, the method comprising: (a) providing a pseudotyped lentiviral vector particle according to the invention, wherein the truncated H protein of the said vector particle has a known single chain antibody or ligand at its ectodomain, directed against or binding to an antigen or receptor on a cell and said vector particle further comprises an expression vector, wherein said expression vector encodes a expressible reporter gene; (b) transducing cells with an expression library of the cell of step (a); (c) contacting the pseudotyped lentiviral vector particle of step (a) with transduced cells of step (b); (d) selecting cells expressing the expressible reporter gene; and (e) determining the genetic information of the antigen or receptor from the selected cells of step (d). In a preferred embodiment the expressible reporter gene is a gene coding for a gene product selected from the group of a selectable marker gene, a gene encoding a fluorescent protein, a gene conferring antibiotic resistance, neomycin, GFP and eGFP.

In another preferred embodiment the population of cells naturally expresses the cell marker, antigen or receptor, or wherein the population of cells has been transiently or stably transfected to express said cell marker, antigen or receptor.

In another preferred embodiment the cell marker, antigen or receptor is selected from the group consisting of CD4, CD8, CD34, CD20, CD19, CD33, CD133, EGF-R and VEGFR-2.

In another preferred embodiment the amount of truncated F protein of the pseudotyped lentiviral vector particles is higher than the amount of truncated H protein, preferably the amount of truncated F protein is 10-100% higher, is 100-250% higher, is 250-500% higher, is 500-750% higher, is 750-1000% higher, is more than 1000% higher and most preferably is 700% higher than the amount of truncated H protein.

EXAMPLES

Materials & Methods
Used Plasmids
Plasmids Encoding Envelope Proteins:
  pCG-H encoding the MV H gene
  pCG-HcΔ14 to pCG-HcΔ24 encoding the MV H gene with a truncated cytoplasmic tail of the indicated number of amino acids
  pCG-HcΔ21+A, pCG-HcΔ24+4A, pCG-HcΔ26+6A and pCG-HcΔ30+10A encoding the MV H gene with a truncated cytoplasmic tail of 21, 24, 26 and 30 amino acids, respectively, and one, four, six or ten added alanines after the start methionine of the MV H protein pCG-F encoding the MV F gene pCG-FcΔ24 and pCG-FcΔ30 encoding the MV F gene with a truncated cytoplasmic tail of the indicated number of amino acids pCG-HmutscFvCD20Δ18, pCG-HmutscFvCD20Δ19 and pCG-HmutscFvCD20Δ24+4A encoding the MV H gene with the four point mutations Y481A, R533A, S548L, F549S, a truncated cytoplasmic tail of the indicated number of amino acids and the scFvCD20 DNA sequence fused to the C terminal coding region of the HmutΔ protein.

pCG-HmutEGFΔ18, pCG-HmutEGFΔ19 and pCG-HmutEGFΔ24+4A encoding the MV H gene with the four point mutations Y481A, R533A, S548L, F549S, a truncated cytoplasmic tail of the indicated number of amino acids and the EGF DNA sequence fused to the C terminal coding region of the HmutΔ protein.

pCG-HmutscFvGluR4Δ18 encoding the MV H gene with the four point mutations Y481A, R533A, S548L, F549S, a truncated cytoplasmic tail of the indicated number of amino acids and the scFvGluR4 DNA sequence fused to the C terminal coding region of the HmutΔ protein.

pMDG encoding the VSV-G glycoprotein of the vesicular stomatitis virus pHIT123 encoding the envelope protein (Env) of the ecotropic MLV Plasmids Encoding the Gag and Pol Genes pCMVΔR8.9 encoding HIV-1 gag/pol pHIT60 encoding MLV gag/pol SIV10+ encoding SIVmac gag/pol Transfer Plasmids pHRCMVGFP is a HIV-1 packagable vector encoding the GFP reporter gene pSEW is a HIV-1 packagable vector encoding the GFP reporter gene pSFG-eGFP is a MLV packagable vector encoding the GFP reporter gene GAE-SFFV-GFP-WPRE is a SIVmac packagable vector encoding the GFP reporter gene pS-CD34TK39-W is a HIV-1 packagable vector encoding the CD34TK39 fusion protein gene Polymerase Chain Reaction The polymerase chain reaction (PCR) allows to amplify specific DNA sequences of different origins, such as plasmid, genomic or complementary DNA (Saiki et al., 1985; Mullis et al., 1987). The amplified fragment can subsequently be used for further molecular biological methods. Current PCR protocols make use of a DNA-dependent DNA polymerase isolated from *Thermophilus aquaticus* (Taq Polymerase), which shows a temperature optimum of 72° C. Using appropriate buffers, primers, deoxynucleotides and cycling conditions the Taq polymerase can amplify a DNA fragment bordered by the two primer sequences. Under optimal conditions this amplification takes place in an exponential manner.

A typical PCR cycle contains a denaturation step at 94° C., leading to the dissociation of the double stranded template. The following hybridization step allows primer annealing to the resulting single stranded template. The hybridization temperature $T_D$ is adjusted according to length and composition of the DNA template. It can be calculated roughly corresponding to the Wallace rule (Suggs et al., 1981) as follows: $T_D=4\times(G+C)+2\times(A+T)$. After hybridization, DNA elongation is performed at 70-75° C. The elongation time ($t_E$) is chosen in pursuance with the template length, approximately 1 min/1 kb DNA. By repeating the cycle sequence the template is amplified in an exponential manner.

- 1×PCR buffer (20 mM Tris/HCl, pH 7.5; 100 mM KCl; 1.5 mM $MgCl_2$; 1 mM DTT; 0.1 mM EDTA, 0.5% Tween 20; 0.5% Nonidet P40; 0.01% gelatine)
- 1-2 μM (+)-primer and (−)-primer, respectively
- 200 μM of each deoxynucleotide
- 5 units Taq DNA polymerase
- 0.1 μg plasmid or genomic DNA containing the fragment of interest PCR Conditions 95° C. 1 min
95° C. 30 sec
$T_D$° C. 30 sec — 15 cycles
72° C. $t_E$ sec
72° C. 7 min; subsequent cool down to 4° C.

Restriction and Ligation of Plasmid DNA

All DNA restrictions were performed using commercially available restriction endonucleases from New England Biolabs (NEB, Schwalbach, Germany) according to the manufacturers instructions.

Standard Restriction Reaction for Preparative Purposes

10 μg DNA

40 U restriction enzyme

10 μl 10× buffer (NEB buffer 1-4, corresponding to the used restriction enzyme)

10 μl 10×BSA (NEB; only if required by the applied enzyme)

ad 100 μl aqua bidest

The restriction sample was incubated at the temperature optimum of the used restriction enzyme/s for two hours or over night. Using two enzymes a buffer was chosen, which is adequate for both enzymes.

Standard Restriction Reaction for Analytic Purposes

1 μg DNA

10 U restriction enzyme

2 μl 10× Puffer (NEB buffer 1-4, corresponding to the used restriction enzyme)

2 μl 10×BSA (NEB; only if required by the applied enzyme)

ad 20 μl aqua bidest

Incubation for 90 min at the temperature optimum of the applied enzyme/s. Double digests were performed as described for preparative purposes.

Ligation of Digested Fragments

Recombination of DNA is usually performed by ligation of two double stranded nucleic acid molecules exhibiting complementary overhangs or blunt ends. This reaction can be accomplished using T4 DNA ligase which catalyzes the formation of phosphodiester bonds between the fragments under consumption of ATP. The following reaction mixture has been used as standard sample:

Approximately 0.3 µg DNA (molar ratio of backbone to insert=1:3)
2 µl ligase buffer (NEB)
0.5 µl T4-DNA-ligase (200 U)
ad 20 µl aqua bidest.

The reaction mix was incubated by 16° C. over night.

In Vitro Site-Directed Mutagenesis of Plasmid DNA

In vitro site directed mutagenesis allows to exchange desired nucleotides within a plasmid backbone.

For this purpose, the Stratagene Quick Change Site Directed Mutagenesis Kit (Stratagene, La Jolla, USA) has been used according to the manufacturers instructions. This method is based on Pfu polymerase mediated extension of phosphorylated primers, which contain the desired mutation. Double stranded supercoiled plasmids served as templates and were denatured at 95° C. for 30 seconds. Then, the temperature was lowered to 55° C. for 30 seconds to allow annealing of the primers. Subsequently, primer extension was performed at 68° C. for 12 min. Overall, 18 reaction cycles were performed. During this procedure, the newly synthesized strands were also ligated with the 5'-end of the applied primers due to heat stable ligases present in the enzyme mix. As a result, circularized DNA including the desired mutations was generated. Subsequently, the initial template strands were digested with DpnI. This enzyme specifically cuts methylated DNA, as isolated from bacteria, but does not affect the newly in vitro synthesized strands. Thus, the reaction mixture could be used for transformation of E. coli cells to specifically amplify the mutated plasmids.

Generation of Competent Bacteria and Transformation Thereof

Transformation of E. coli (K12-derived safety strains) is the method of choice to amplify plasmid DNA through cellular replication. For this purpose, bacteria have to be pretreated in a special manner to become competent, thus allowing introduction of foreign DNA.

2.5 ml of an over night culture were used to inoculate 100 ml of fresh LB-Media which was subsequently incubated at 37° C. in a bacteria shaker. Cells were allowed to grow up to an $OD_{550}$ of about 0.5-0.55 hence reaching the logarithmic growth phase. Then the culture was incubated on ice for 5 minutes, divided into two portions and pelleted at 6000 rpm for 10 minutes at 4° C. Then the cells were resuspended in 20 ml TFB1-buffer (sterile filtrated solution of 30 mM KOAc, 100 mM $RbCl_2$, 10 mM $CaCl_2$, 50 mM $MnCl_2$, 15% glycerin, pH adjusted to 5.8 with HAc) respectively, incubated on ice for 5 minutes and once again pelleted as above. Subsequently the cells were resuspended each in 2 ml TFB2-buffer (sterile filtrated solution of 10 mM MOPS, 75 mM $CaCl_2$, 10 mM $RbCl_2$, 15% glycerine, pH adjusted to 6.5 using KOH-solution) and incubated on ice for 15 minutes. Afterwards the suspension was portioned into Eppendorf tubes of 100 µl and frozen at −80° C.

For standard plasmid amplification, transformation of the chemically competent cells described above has been performed. For this purpose, the cells were thawed on ice and approximately 50 ng DNA were added. After further incubation on ice for 30 min, a heat shock at 42° C. for 45 sec was performed in a thermoblock. Then 500 µl of prewarmed (37° C.) SOC medium (Invitrogen, Carlsbad, USA) was added and the sample was incubated for 60 min at 37° C. Then the bacteria suspension was plated onto LB-AMP-plates (1% (w/v) Bacto-Trypton, 0.5% (w/v) yeast extract, 1% NaCl, 50 µg/ml ampicilin 1.5% (w/v) agar agar).

Plasmid Preparation

Preparation of plasmids from bacteria was performed using the Qiagen plasmid kits (Qiagen, Hilden, Germany) according to the manufacturers instructions. The basic principle of this method is binding of DNA to anion exchange columns. Thus, all cellular compounds such as proteins can be washed away whereas the DNA is retained within the columns.

For purification of low amounts of DNA (Miniprep), 5 ml over night cultures were inoculated using LB-AMP-Medium (1% (w/v) Bacto-Trypton, 0.5% (w/v) yeast extract, 1% NaCl, 50 µg/ml ampicilin). The next day, bacteria were harvested at 3000 rpm for 10 min (Minifuge RF, Heraeus, Hanau, Germany). The resulting pellet was lysed using solutions delivered by the manufacturer (P1 & P2). Chromosomal DNA and cellular fragments were excluded by centrifugation (13000 rpm for 5 min in an Eppendorf table centrifuge). Subsequently the supernatant was applied to anion exchange columns (Qiaprep-8-strips) according to the manual.

For extraction of larger amounts of DNA (Maxiprep) 200 µl LB-AMP-Media were inoculated and cultivated over night. Bacterial yield was performed at 7000 rpm for 15 min (JS-13.1-rotor, J2-21-centrifuge; Beckman, Munich, Germany). Afterwards cells were lysed and the remaining cell debris and chromosomal DNA was removed by centrifugation (10000 rpm for 20 min). The resulting supernatant was subsequently purified over an anion exchange column according to the manufacturer's instructions. Finally, concentration and purity of the DNA was determined photometrically.

Agarose Gel Electrophoresis

Agarose gel electrophoresis allows to separate DNA molecules by their size. The principle is based on the properties of polymerized agarose, which acts like a molecular sieve. Since DNA is negatively charged, it migrates through such gels upon application of electric current in a size dependent manner.

For fragments with a size of 1 kb-14 kb, 1% agarose gels were used, whereas 1.5-2% agarose gels were used for smaller fragments (according to the fragment of interest). The gels were generated by adding the corresponding amount of agarose to 130 ml TAE buffer. The resulting emulsion was then heated in a microwave oven until the solid agarose became solved. Then, 50 µg/ml ethidium bromide were added and the gel was casted into the tray. DNA samples were mixed with 0.2 volumes 5× sample buffer (30% glycerin and 1% brome phenol blue in 5×TAE buffer) and applied to the gel. As marker, either the 1 kb or the 100 bp ladder (NEB, Schwalbach, Germany) were used according to the fragment size. Electrophoresis was then performed at 130 V for approximately 45 minutes. Afterwards fragment bands were photographically documented under UV light and, if desired, bands were cut out for purification as described below.

| TAE buffer | |
|---|---|
| Tris-Acetat | 40 mM |
| EDTA | 1 mM | adjusted to pH 7.5

Isolation of DNA Fragments from Agarose Gels

Purification of DNA fragments from agarose gels was performed using the Jetsorb gel extraction kit (Genomed, Löhne, Germany) according to the manufacturers instructions. This method is based on the intrinsic adhesion of DNA to glass powder.

After electrophoretic separation the DNA band of interest was cut out of the gel and transferred into an Eppendorf tube. These samples were purified according to the manual with the following modification: Only 2 µl of the glass powder suspension were added to the samples and elution was performed using 10 µl $H_2O$. These modifications were invented to enhance the final DNA concentration which was determined photometrically. High DNA concentrations allow to enhance the ligation and transformation efficiencies which is especially important when generating plasmid libraries.

of complementary A/T overhangs and subsequent formation of phosphodiesterbonds through the T4 ligase. PCR fragments generated with the taq polymerase always exhibit 3'-A-overhangs and the pGEMTeasy vector is cut in a way that 5'-T-overhangs are left. Hence the kit provides an efficient tool to individualize DNA fragments composed of different sequence variants by transformation of *E. coli* with the resulting vectors. Miniprep DNA obtained from these clones was then used for sequencing.

Cell Culture

Cells were cultivated in an incubator (Heraeus, Hanau, Germany) at 37° C., 5% CO, and saturated water atmosphere. Adherent cells were trypsinized (0.25% trypsin in PBS) for passaging. A fraction of the resulting suspension was seeded into new culture flasks and fresh medium was added.

Used Cell Lines

| | |
|---|---|
| HEK-293T | DMEM with 4.5 g/l glucose, 3.7 g/l $NaHCO_3$, 10% FCS, 1% glutamine |
| HT1080 | DMEM with 4.5 g/l glucose, 3.7 g/l $NaHCO_3$, 10% FCS, 1% glutamine |
| HT1080-CD20 | HT1080 cells stably expressing human CD20 |
| | DMEM with 4.5 g/l glucose, 3.7 g/l $NaHCO_3$, 10% FCS, 1% glutamine, 3 µg/ml puromycin |
| A-431 | DMEM with 4.5 g/l glucose, 3.7 g/l $NaHCO_3$, 10% FCS, 1% glutamine |
| CHO-K1 | DMEM with 4.5 g/l glucose, 3.7 g/l $NaHCO_3$, 10% FCS, 1% glutamine |
| CHO-hSLAM | CHO cells stably expressing human SLAM |
| | RPMI 1640 with 2 g/l $NaHCO_3$, 10% FCS, 1% glutamine, 0.5 mg/ml G418 |
| CHO-BC1 | CHO cells stably expressing human CD46 |
| | DMEM with 4.5 g/l glucose, 3.7 g/l $NaHCO_3$, 10% FCS, 1% glutamine, 1.2 mg/ml G418 |
| U-87MG | MEM with 0.85 g $NaHCO_3$/l, 1 ml/100 ml glutamin, 1 ml/100 ml not essential amino acids, 10 ml/100 ml FCS, 1 ml/30 ml bicarbonate, 1 ml/100 ml pyruvate |
| A301 | RPMI 1640 with 2 g/l $NaHCO_3$, 10% FCS, 1% glutamin |
| Daudi | RPMI 1640 with 2 g/l $NaHCO_3$, 10% FCS, 1% glutamin |
| Raji | RPMI 1640 with 2 g/l $NaHCO_3$, 10% FCS, 1% glutamin |
| K-562 | RPMI 1640 with 2 g/l $NaHCO_3$, 10% FCS, 1% glutamin |
| HT1080-GluR4 | HT1080 cells stably expressing human glutamate receptor-4 |
| | DMEM with 4.5 g/l glucose, 3.7 g/l $NaHCO_3$, 10% FCS, 1% glutamine, 1.0 mg/ml G418 |

Preparation of Genomic DNA

Genomic DNA was isolated from cultured adherent cells using the DNeasy Tissue Kit (Qiagen, Hilden, Germany) according to the manufacturers instructions. This method is based on binding of nucleic acids to silica-gel-membrane columns. In addition, RNA is excluded from purification through RNAse H digestion. Thus, DNA is retained, whereas all other cellular components can be washed away.

Cells were trypsinized within the culture flasks and the resulting cell suspension was centrifuged at 3000 rpm in an Eppendorf table centrifuge. Approximately $2 \times 10^6$ cells were resuspended in 200 µl PBS-EDTA (these samples can be stored at $-20°$ C.) and applied to the purification procedure as described in the manual with the following modification: For elution of the DNA from the columns 80 µl of buffer AE were used instead of 200 µl to increase the DNA concentration for the subsequent PCR.

Nucleic Acid Sequencing

Nucleic Acid sequencing was performed at MWG Biotech (Ebersberg, Germany). For this purpose, DNA samples containing approximately 1 µg Plasmid DNA were vacuum dried using a speedvac centrifuge. The resulting dried samples were sent to the company via regular mail, where they were sequenced using an appropriate primers.

For sequencing of library variants, PCR fragments were ligated into pGEMTeasy vectors according to the manufacturers instructions. This ligation step is based on annealing Freezing and Thawing of Cultured Cells For storage, cells were kept at $-80°$ C. or, for long term storage, in liquid nitrogen.

Freezing

Cells were trypsinised and resuspended in appropriate medium. Subsequently a centrifugation step (800 rpm for 10 min at 4° C. in a Heraeus centrifuge) was carried out to pellet the cells. These were then resuspended in freezing medium (90% FCS, 10% DMSO), divided into cryotube aliquots of approximately $1.5 \times 10^6$ cells and frozen.

Thawing

Cryotubes were incubated in a water bath at 37° C. until the ice thawed. Then the cell suspension was immediately transferred into a falcon tube with 15 ml prewarmed medium. To exclude the cytotoxic DMSO, cells were subsequently centrifuged (1200 rpm for 6 min at room temperature) and resuspended in fresh medium and seeded into appropriate culture flasks.

Cell Transfection

To express plasmids within eucaryotic cells calcium phosphate transfection was performed.

For the generation of vector particles, 24 h before transfection, $6.5 \times 10^6$ HEK-293T cells (in DMEM with 4.5 g/l glucose, 3.7 g/l $NaHCO_3$, 10% FCS, 1% glutamine, 0.5% penicillin and streptomycin) were seeded into a T75 flask. 1 h before the transfection the medium of the cells was exchanged against 5 ml fresh medium. 4.0 µg of plasmid encoding a F protein variant and 4.0 μg of plasmid encoding a H protein variant, 6.72 μg of packaging plasmid, encoding HIV-1 and MLV gag/pol, respectively, and 11.27 μg of transfer plasmid, were co-transfected by calcium phosphate transfection. The plasmid DNA is filled up with $H_2O$ (Sigma; W-3500) to 450 μl. Then 50 μl 2.5 M $CaCl_2$ (Sigma, C7902) solution are added. While vortexing the DNA-$CaCl_2$, solution, 500 μl 2×HBS Buffer (281 mM NaCl (Sigma, S7653); 100 mM HEPES (Sigma, H3375); 1.5 mM $Na_2HPO_4$ (Sigma, S0876)) are added dropwise. The suspended precipitate is then transferred to the HEK-293T cells. 3-4 h later, 5 ml fresh medium is added and 15 h after this the medium is again replaced with 12 ml fresh medium.

24 h afterwards, the 12 ml cell supernatant containing the pseudotyped lentiviral vector particles, are filtered (0.45 μm filter) and 200 μl thereof were directly used for the transduction of HT1080 cells. The remaining supernatant was concentrated by centrifugation at 3600 rpm (Heraeus multifuge 3S-R) and 40° C. for at least 16 h. The pellet was then resuspended in 120 μl serum free medium (DMEM with 4.5 g/l glucose, 3.7 g/l $NaHCO_3$).

Transduction and Titration

For titration of the unconcentrated and the concentrated vector particle stocks, $1.0 \times 10^5$ HT1080 cells (in DMEM with 4.5 g/l glucose, 3.7 g/l $NaHCO_3$, 10% FCS, 1% glutamin, 0.5% penicillin/strepromycin) were seeded into a single well of a 24-well plate. On the next day, the vector stocks were serially diluted in 1:10 steps and a total of 180 μl of the dilutions, including 1.44 μg polybrene was then added to every well, incubated for 2.5-3h and replaced by 1 ml of fresh medium. After 48-72 h the titers were calculated by determining the number of green fluorescent cells per well by counting under the fluorescence microscope. For counting a dilution is selected where significantly less than every cell has been transduced. To figure out the number of transducing particles per ml the counted cells per well were multiplied by the dilution factor and the factor 5.6 (used 180 μl×5.6=1 ml).

The titers were also determined by FACS analysis.

Fluorescence Activated Cell Sorting (FACS)

FACS analysis allows to assay cell populations for surface expression of proteins. The method makes use of scattered light and fluorescence of labelled antibodies. In principle, FACS can also be used for intracellular stainings after membrane perfusion thus also allowing to analyse the expression of cytosolic proteins. Also the cytosolic expression of GFP can be detected.

The transduced cells of a well with an adequate dilution are detached by incubation with 100 μl PBS-Trypsin solution. Then 1 ml FACS washing buffer (PBS, 2% FCS, 0.1% $NaN_3$) is added and this cell solution is then centrifuged for 2 min by 3.500 rpm (Biofuge fresco Heraeus instruments) at 4° C. The pellet is resuspended in 1 ml FACS washing buffer and centrifuged as above. Then, the cell pellet is resuspended in 200 μl PBS/1% paraformaldehyde. With the FACS machine (Dako Galaxy flow cytometry system) 10,000 cells are counted and with the indicated percentage of green fluorescence cells the number of transducing particles per ml can be determined. The number of cells at the timepoint of transduction is multiplied by the percentage indicated and then divided by 100. This number of transduced cells is then multiplied by the dilution factor and the factor 5.6 (used 180 μl×5.6=1 ml)

Example 1: Truncated and Mutated MeV H and F Proteins

MeV F and H glycoproteins were inserted into the expression vector pCG under the control of the CMV early promoter as described by Cathomen et al. (1995) and various pCG-H and pCG-F vectors were constructed, wherein the H and F genes carried point mutations, deletions and insertions.

The truncated H protein genes were generated by PCR using pCG-H as a template. A forward primer complementary to coding region of the N terminus of the H protein gene was used. This primer encodes at its 5' end the nucleotide sequence for the PacI restriction site followed by the start methionine triplet and the nucleotide sequence of the H protein cytoplasmic tail but omitting those triplets coding for the amino acids to be deleted. The reverse primer was complementary to coding region of the transmembrane domain of the H protein and comprises at its 5' end the NheI restriction site sequence. For HcΔ18, for example, the primers were as follows: forward 5'-CCT-TAAITAAATGGGAAGTAGGATAGTC-3' (SEQ ID NO: 13); reverse 5'-CTAGCTAGCAACCCGATC-3' (SEQ ID NO: 14). In this way the PCR fragment with the truncated cytoplasmic tail of the H protein can be cloned PacI/NheI into the pCG-H plasmid leading to, for example, pCG-HcΔ18.

The PCR fragment and the pCG-H DNA is incubated with the enzymes PacI (commercially available at NEB) and NheI (commercially available at NEB) in the appropriate buffer at 37° C. over night. The restriction fragments are resolved in a 1.5% agarose gel. The adequate PCR fragment and vector DNA is extracted from the gel using the Jetsorb Gel extraction Kit (Genomed). The purified PCR fragment and vector DNA are then ligated at 16° C. over night using T4 DNA Ligase (commercially available at NEB).

The ligation reaction is then used to transform *E. coli* strain Top10 as follows. The ligation reaction is incubated with 100 μl chemical competent *E. coli* Top10 for 30 min on ice, followed by a heat shock at 42° C. for 45 s. Afterwards, 500 μl SOC Medium (Invitrogen) is added and the bacteria are then incubated at 37° C. and 600 rpm in an Eppendorf thermomixer for 1 h.

Figure 9:
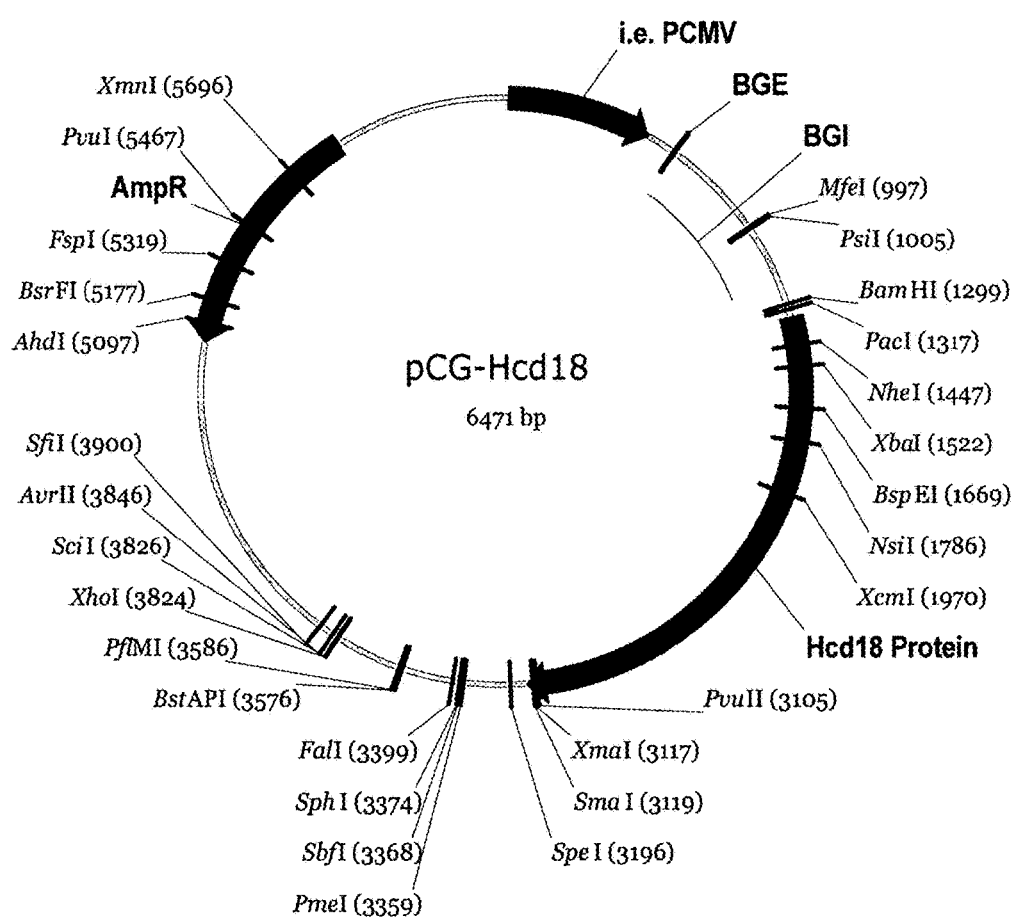

Subsequently, the transformed bacteria are plated out onto an LB-ampicillin plate and incubated over night at 37° C. The next day some clones are picked for a mini DNA preparation according to the protocol of the QIAprep® Spin Miniprep Kit (Qiagen). After identification of the isolated plasmid DNA, e.g. pCG-HcΔ18, through digestion with appropriate restriction enzymes, the plasmid DNA can be stored or directly used for further experiments. The plasmid map for pCG-HcΔ18 is depicted in FIG. 9.

In case of the truncated HcΔ21+A and HcΔ24+4A proteins, respectively, the same reverse primer as above can be used together with the following two forward primers: 5'-CCTTAATTAAATGGCTATAGTCATAACAGAGAAC-3' (SEQ ID NO: 15) and 5'-CCTTAATTAAATGGCTGC-CGCAGCGAACAGAGAACATCTTATG-3' (SEQ ID NO: 16), respectively.

Figure 10:
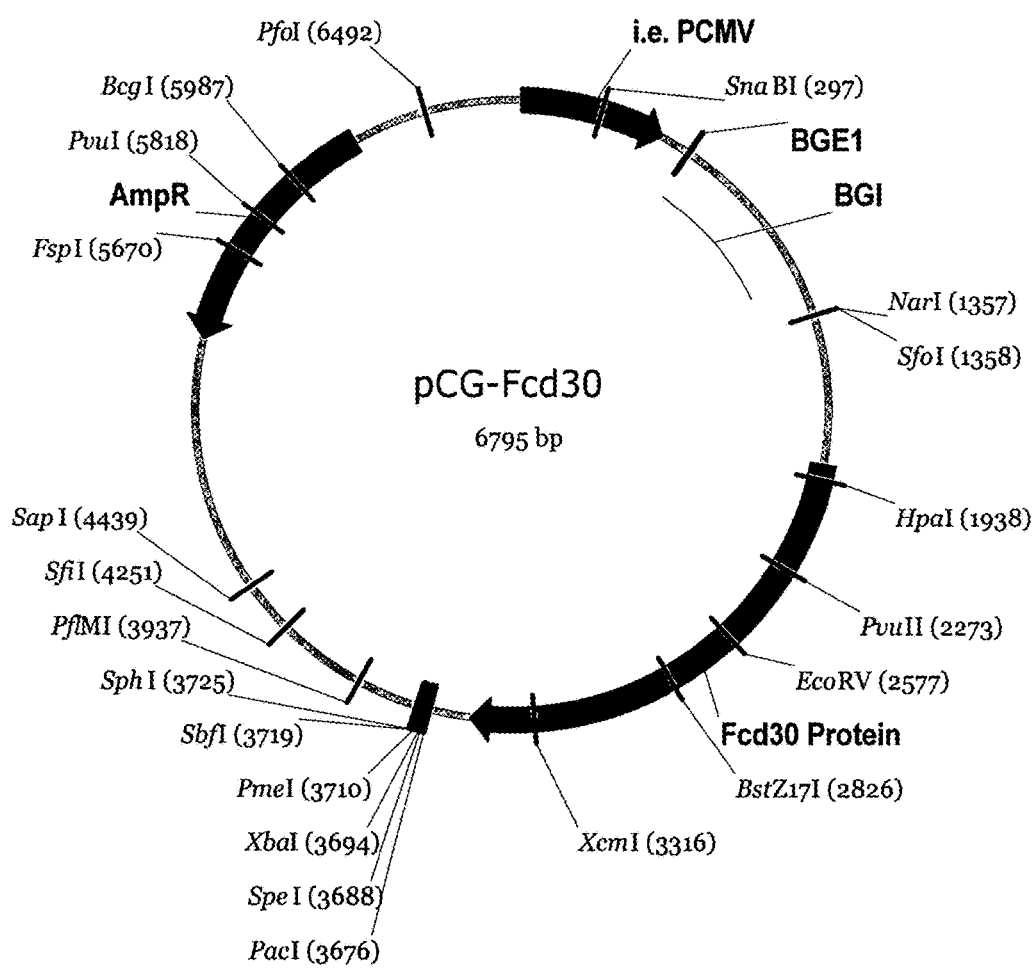

The truncated F proteins can be generated by introducing a premature stop codon by site directed mutagenesis according to the protocol of the QuikChange® Site-directed mutagenesis kit (Stratagene). As template the plasmid pCG-F is used. Exemplarily, primers 5'-GCTGCAGGGGGCGTTG A̲AATAAAAAGGGAGAAC-3' (SEQ ID NO: 17) (for FcΔ30) and 5'-GTAATAAAAAGGGAGAA T̲AAGTGGTATGTCAAG-3' (SEQ ID NO: 18) (for FcΔ24) can be used (the exchanged nucleotide is underlined). Exemplarily, the plasmid map for pCG-FcΔ30 is depicted in FIG. 10.

The introduction of the four point mutations Y481A, R533A, S548L, F549S into the truncated H proteins can also be performed by site directed mutagenesis, according to the protocol of the QuikChange® Site-directed mutagenesis kit (Stratagene). Such a mutagenesis is exemplarily described for pCG-HcΔ18, pCG-HcΔ19 and pCG-HcΔ24+4A in the following. As template in the first mutagenesis the plasmid pCG-HcΔ18, pCG-HcΔ19 and pCG-HcΔ24+4A, respectively, is used together with the primer 5'-GATTCAAGGTTAGTCCCGCACTCTCACTGTCCC-3' (SEQ ID NO: 19) (Y481A). In a second cycle of mutagenesis, the produced plasmid of the mutagenesis cycle one is used as template. The primer used is 5'-CCTACGATACTTCCGCGGTGAACATGCTGTGG-3' (SEQ ID NO: 20) (R533A). In the third mutagenesis cycle, the plasmid of mutagenesis two is used as template, together with the primer 5'-GTTTTACAGCCCAAGCCGCCTATCGTCTTACTTTTATCC-3' (SEQ ID NO: 21) (S548L, F549S). The exchanged nucleotides are underlined. The produced plasmid of mutagenesis three thus contains all four point mutation in the ectodomain of the truncated H protein of, for example, pCG-HmutΔ18.

In a next step, the SfiI site in the plasmids pCG-HmutΔ18, pCG-HmutΔ19 and pCG-HmutΔ24+4A is destroyed by site directed mutagenesis according to the protocol of the QuikChange® Site-directed mutagenesis kit (Stratagene). The following primer is used: 5'-CTGGAATAGCTCAGAATCCGAGGCATCCTCGGCCTCTGC-3' (SEQ ID NO: 22) (again, the exchanged nucleotides are underlined). In a next step the coding region for the scFvCD20 flanked by SfiI and NotI restriction sites can be introduced into the plasmids pCG-HmutΔ18, pCG-HmutΔ19 and pCG-HmutΔ24+4A. The scFvCD20 was PCR-amplified from cDNA encoding the murine anti-CD20 antibody B9E9 (GenBank sequence B9E9 $V_H$ AF277091 and B9E9 $V_L$ AF277092) with an 18-mer linker between the $V_H$ and $V_L$ domains. The scFvCD20 coding region is fused in frame to the C terminal end of the HmutΔ protein. This is done by fusion PCR using the following primers for the first amplification step of the C terminal portion of the HmutΔ protein: 5'-CCAATGCATTGGTGAACTCAAC-3' (SEQ ID NO: 23) (encoding an NsiI restriction site at the 5'end) and 5'-CCTTCCCTCGATGGCCGGCTGGGCCGCATIGGTTCCATCTCCCG-3' (SEQ ID NO: 24) (encoding a SfiI restriction site and a factor Xa cleavage site at the 5'end). For the first amplification step of the scFvCD20 DNA these two primers are used: 5'-GGCCCAGCCGGCCATCGAGGGAAGGATGGCTCAGGTTCAGCTG-3' (SEQ ID NO: 25) (having a SfiI restriction site and a factor Xa cleavage site at the 5'end) and 5'-CTAGACTAGTTAGTGATGGTGATGGTGATGAGAACCTCTTGCGGCCGCCTICAGCTCCAGCTITGG-3' (SEQ ID NO: 26). (having a NotI restriction site, a his-tag and a SpeI restriction site at the 5'end). In a fusion step, the isolated PCR fragments with an overlapping sequence of 25 nucleotides (underlined) were mixed and amplified with the external primers, also used for the first amplification round. The resulting PCR fragment was digested with NsiI and SpeI (commercially available at NEB) and subcloned into pCG-HmutΔ18, pCG-HmutΔ19 and pCG-HmutΔ24+4A with the destroyed SfiI site, respectively, as described for the production of the pCG-HΔ constructs.

FIGS. 1A and 1B depict the DNA and amino acid sequence of the MeV $H_{Edm}$ wildtype (wt) protein, wherein the portion of the cytoplasmic domain is shown in bold. FIGS. 2A and 2B show the DNA and amino acid sequence of the MeV $F_{Edm}$ wildtype (wt) protein, wherein the portion of the cytoplasmic domain is shown in bold.

Starting from the wt DNA, truncated and mutated derivates of the MeV $H_{Edm}$ and $F_{Edm}$ genes were designed. First, consecutive deletions in the cytoplasmic domain of varying length were introduced in both the H (deletions of 14 to 24 amino acids) and F protein (deletions of 24 and 30 amino acids). FIGS. 3A-3C exemplarily show the DNA sequence of three of the truncated H proteins derived from the $H_{Edm}$ wt DNA, namely, HcΔ18, HcΔ19 and HcΔ24+4A, respectively. FIG. 3D exemplarily depicts the amino acid sequence of HcΔ18. FIGS. 3E and 3F exemplarily depict the DNA and amino acid sequence of one of the truncated F proteins derived from the $F_{Edm}$ wt DNA, namely FcΔ30. The cytoplasmic portions are shown in bold.

Furthermore, 1 to 4 alanine residues were added to the truncated HcΔ21 and HcΔ24 proteins. FIG. 3G depicts the DNA sequence of the truncated HcΔ24 protein, wherein the additional four alanine residues were added to thus yield HcΔ24+4A. Again, the cytoplasmic portions are shown in bold.

FIGS. 4A and 4B provide an overview over some of the generated F and H mutant proteins in comparison to their respective wt molecules and indicating the deleted (or added) amino acid residues in the cytoplasmic portion of the proteins.

Figure 5C:
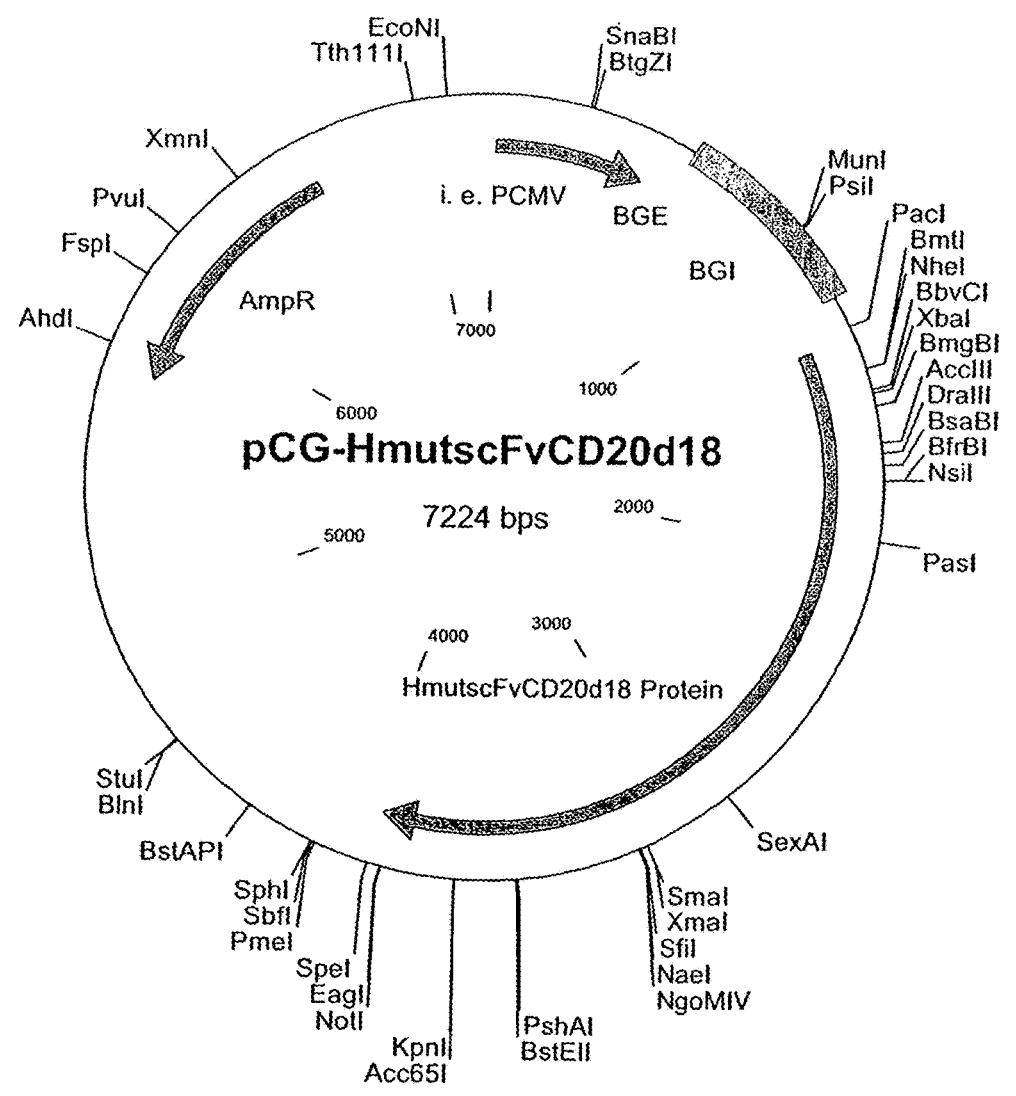

In addition, fusion constructs of mutated and truncated H proteins were constructed, two of which are exemplarily depicted in FIGS. 5 and 6. Starting from HcΔ18, wherein the cytoplasmic portion is shortened by 18 amino acid residues, four point mutations (Y481A, R533A, S548L, F549S) were introduced. In a subsequent step, a single chain antibody (scFv) directed to CD20 (scFvCD20) was fused to the C-terminus of the protein. FIGS. 5A and 5B depict the DNA (SEQ ID NO: 1) and amino acid sequences (SEQ ID NO: 2) of the resulting HmutscFvCD20Δ18 molecule. The four mutation sites are underlined, the SfiI and NotI restriction sites, flanking the scFvCD20 are designated in italics, the HIS-tag is designated underlined and in italics. FIG. 5C shows the plasmid map of the HmutscFvCD20Δ18 plasmid. Thus, the scFvCD20 can easily be removed by cleaving using the SfiI and NotI restriction enzymes, and afterwards be replaced by any other single chain antibody, ligand or cytokine. One example of a ligand is the EGF ligand, the DNA and amino acid sequence of which is depicted in FIGS. 6A and 6B (restriction sites are designated in italics), which was used to construct a corresponding HmutEGFΔ18 molecule (SEQ ID NOs: 3 and 4).

Figure 11:
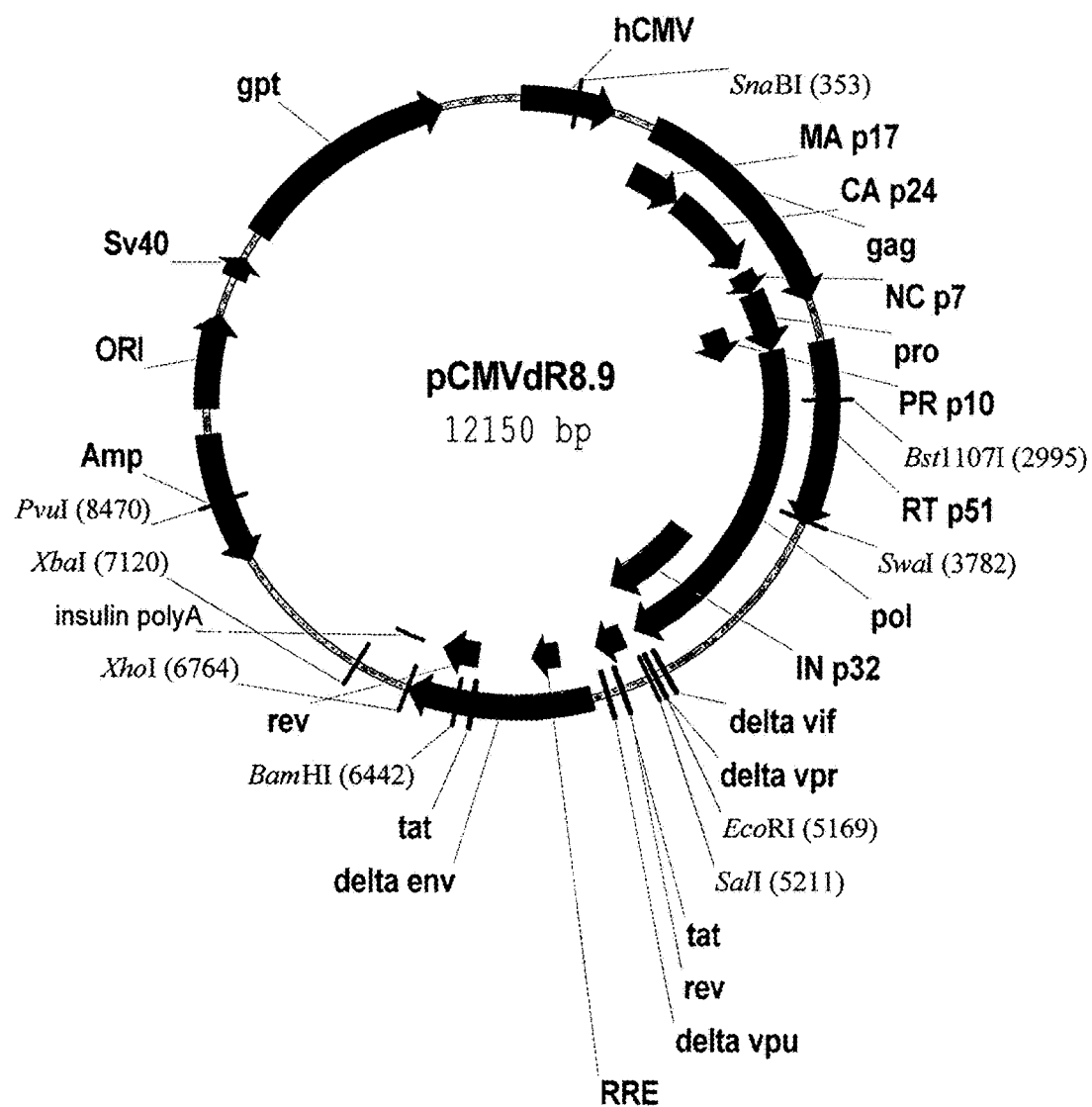
Figure 12:
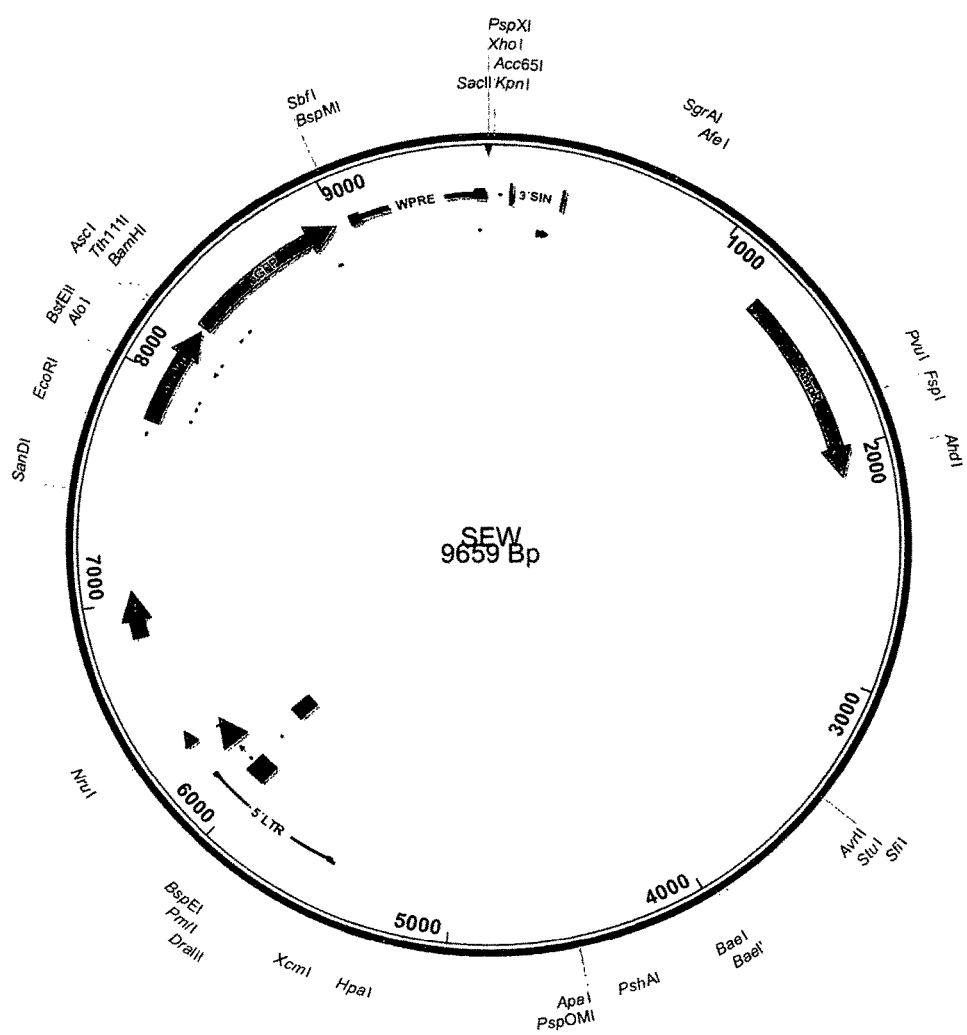

Example 2: Production, Isolation of Pseudotyped Lentiviral Virus Vector Particles and Titration Using HT1080 Cells Pseudotyped lentiviral vector particles were produced by co-transfection of HEK-293T cells with a packaging plasmid, a transfer vector and the two plasmids encoding the H and F protein variants, respectively. The packaging plasmid pCMVΔR8.9 encoding the HIV-1 gag and pol genes is depicted in FIG. 11, as an example the transfer plasmid SEW (encoding for the eGFP) is depicted in FIG. 12, however, as disclosed also other transfer plasmids, such as pHRCM-VGFP encoding a GFP reporter gene may be utilized.

Specifically, 24 h before transfection, $6.5 \times 10^6$ HEK-293T cells (in DMEM with 4.5 g/l glucose, 3.7 g/l $NaHCO_3$, 10% FCS, 1% glutamine, 0.5% penicillin and streptomycin) were seeded into a T75 flask. 1 h before the transfection the medium of the cells was exchanged against 5 ml fresh medium. 4.0 µg of plasmid pCG-FcΔ30, encoding the MeV FcΔ30 protein and 4.0 µg of the plasmid pCG-HcΔ18, encoding the MeV HcΔ18 protein, 6.72 μg of plasmid pCMVΔR8.9, encoding HIV-1 gag/pol and 11.27 μg of pHRCMVGFP, were co-transfected by calcium phosphate transfection. The plasmid DNA is filled up with H$_2$O (Sigma; W-3500) to 450 μl. Then 50 μl 2.5 M CaCl$_2$ (Sigma, C7902) solution are added. While vortexing the DNA-CaCl$_2$ solution, 500 μl 2×HBS Buffer (281 mM NaCl (Sigma, S7653); 100 mM HEPES (Sigma, H3375); 1.5 mM Na$_2$HPO$_4$ (Sigma, S0876)) are added dropwise. The suspended precipitate is then transferred to the HEK-293T cells. 3-4 h later, 5 ml fresh medium is added and 15 h after this the medium is again replaced with 12 ml fresh medium.

24 h afterwards, the 12 ml cell supernatant containing the pseudotyped lentiviral vector particles, are filtered (0.45 μm filter) and 200 μl thereof were directly used for the transduction of HT1080 cells. The remaining supernatant was concentrated by centrifugation at 3600 rpm (Heraeus multifuge 3S-R) and 40° C. for at least 16 h. The pellet was then resuspended in 120 μl serum free medium (DMEM with 4.5 g/l glucose, 3.7 g/l NaHCO$_3$).

For titration of the unconcentrated and the concentrated vector particle stocks, 1.0×10$^5$ HT1080 cells (in DMEM with 4.5 g/l glucose, 3.7 g/l NaHCO$_3$, 10% FCS, 1% glutamin, 0.5% penicillin/strepromycin) were seeded into a single well of a 24-well plate. On the next day, the vector stocks were serially diluted in 1:10 steps and a total of 180 μl of the dilutions, including 1.44 μg polybrene was then added to every well, incubated for 2.5-3h and replaced by 1 ml of fresh medium. After 48-72 h the titers were calculated by determining the number of green fluorescent cells per well by counting under the fluorescence microscope. For counting a dilution is selected where significantly less than every cell has been transduced. To figure out the number of transducing vector particles per ml the counted cells per well were multiplied by the dilution factor and the factor 5.6 (used 180 μl×5.6=1 ml).

The titers were also determined by FACS analysis. For this purpose, the cells of a well with an adequate dilution were detached by incubation with 100 μl PBS-Trypsin solution. Then 1 ml FACS washing buffer (PBS, 2% FCS, 0.1% NaN$_3$) is added and this cell solution is then centrifuged for 2 min by 3.500 rpm (Biofuge fresco Heraeus instruments) at 4° C. The pellet is resuspended in 1 ml FACS washing buffer and centrifuged as above. Then, the cell pellet is resuspended in 200 μl PBS/1% paraformaldehyde. With the FACS machine (Dako Galaxy flow cytometry system) 10,000 cells are counted and with the indicated percentage of green fluorescent cells the the number of transducing vector particles per ml can be determined. The number of cells at the timepoint of transduction is multiplied by the percentage indicated and then divided by 100. This number of transduced cells is then multiplied by the dilution factor and the factor 5,6 (used 180 μl×5.6=1 ml).

Figure 7A:
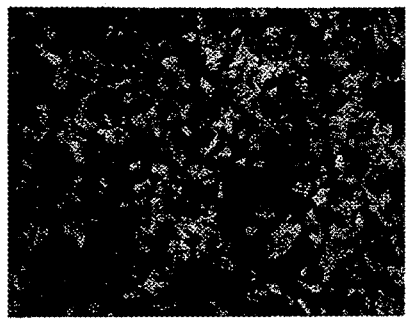
Figure 7B:
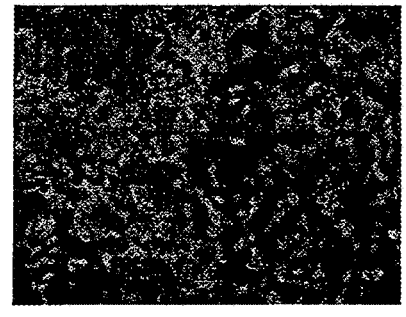
Figure 7C:
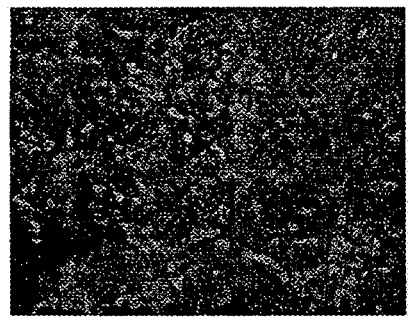
Figure 7D:
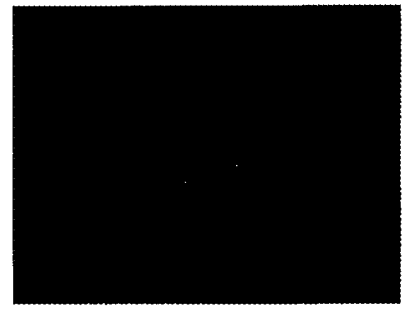
Figure 8A:
Figure 8B:
Figure 8C:
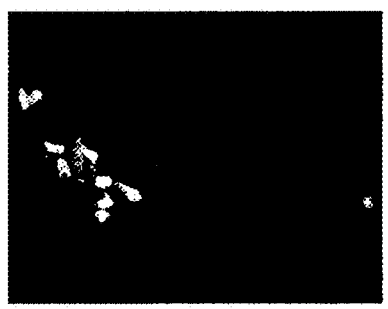
Figure 8D:
Figure 8E:
Figure 8F:

FIGS. 7A-7D show exemplary microscopic pictures of HT1080 cells transduced with the pseudotyped vector particles. In all cases, the HEK-293T cells were co-transfected with packaging plasmid pCMVΔR8.9 and the GFP reporter gene plasmid pHRCMVGFP as described above. FIG. 7A shows the result of an additional co-transfection with pCG-FcΔ30 and pCG-HcΔ18, FIG. 7B shows the result of an additional co-transfection with pCG-FcΔ30 and pCG-HcΔ19, FIG. 7C shows the result of an additional co-transfection with pCG-FcΔ30 and pCG-HcΔ24+4A and FIG. 7D shows the result of an additional co-transfection with the wt plasmids pCG-Fwt and pCG-Hwt. Thus, FIGS. 7A-7D depict the results of the GFP transduction of HT1080 cells by means of the lentiviral vector particles of the invention pseudotyped with FcΔ30/HcΔ18, FcΔ30/HcΔ19, FcΔ30/HcΔ24+4A, and Fwt/Hwt, respectively.

The results clearly show that those vector particles pseudotyped with the truncated versions of the MeV F and H proteins were able to efficiently transduce the GFP gene into the HT1080 cells (FIGS. 7A-7C), while vector particles pseudotyped with the respective wt proteins could not (FIG. 7D).

Furthermore, the titers of the produced pseudotyped vector particles of the invention were determined. Table 1 summarizes the results of the transduction of HT1080 cells by an exemplary selection of these pseudotyped lentiviral vector particles.

TABLE 1

Titers of MV F/H pseudotyped HIV-1 vector particles

| F/H variants | t.u./ml HT1080[1] | t.u./ml HT1080[2] | t.u./ml CHO-K1[2/3] |
|---|---|---|---|
| F$_{wt}$ H$_{wt}$ | 22.4[+] | 0[+] | 0 |
| F$_{wt}$ HcΔ14 | 16.8[+] | 40.0[+] | 0 |
| FcΔ24 H$_{wt}$ | 16.8[+] | 10.0[+] | 0 |
| FcΔ24 HcΔ14 | 1.2 * 10$^{3+}$ | 2.1 * 10$^{4+}$ | 0 |
| FcΔ24 HcΔ15 | 7.3 * 10$^2$ | 6.3 * 10$^3$ | 0 |
| FcΔ24 HcΔ17 | 7.5 * 10$^3$ | 1.4 * 10$^5$ | 0 |
| FcΔ24 HcΔ18 | 4.9 * 10$^{3+}$ | 5.2 * 10$^4$ | 0 |
| FcΔ24 HcΔ19 | 1.9 * 10$^{4+}$ | 6.0 * 10$^5$ | 0 |
| FcΔ24 HcΔ20 | 4.7 * 10$^3$ | 3.1 * 10$^4$ | 0 |
| FcΔ24 HcΔ21 + A | 1.8 * 10$^4$ | 2.7 * 10$^5$ | 0 |
| FcΔ24 HcΔ24 + 4A | 1.0 * 10$^3$ | 6.4 * 10$^4$ | 0 |
| FcΔ30 HcΔ14 | 2.5 * 10$^3$ | 1.0 * 10$^4$ | 0 |
| FcΔ30 HcΔ15 | 3.4 * 10$^3$ | 2.2 * 10$^4$ | 0 |
| FcΔ30 HcΔ17 | 1.6 * 10$^3$ | 2.0 * 10$^4$ | 0 |
| FcΔ30 HcΔ18 | 2.4 * 10$^{5+}$ | 6.2 * 10$^{6+}$ | 0 |
| FcΔ30 HcΔ19 | 1.5 * 10$^{5+}$ | 2.9 * 10$^{6+}$ | 0 |
| FcΔ30 HcΔ20 | 1.2 * 10$^4$ | 1.2 * 10$^5$ | 0 |
| FcΔ30 HcΔ24 + 4A | 2.1 * 10$^5$ | 5.3 * 10$^6$ | 0 |
| pos. control: VSV-G | — | — | 1.1 * 10$^8$ |
| neg. control: MLV Env$_{eco}$ | 30.8[++] | 40.9[++] | 90 |

[1]unconcentrated cell supernatants were used
[2]concentrated cell supernatants were used
[3]CHO-K1 cells do not express CD46 and SLAM
[+]average of 2 experiments
[++]average of 4 experiments
— experiment not carried out The results of the titration experiments thus demonstrate that the use of a combination of truncated MeV F and H proteins generates pseudotyped lentiviral vector particles which efficiently and selectively infect and transduce their target cells, i.e. cells which either express the CD46 or the SLAM surface marker. Significantly, CHO-K1 cells not expressing CD46 or SLAM are not targeted by the lentiviral vector particles of the invention.

Excluding Pseudotransduction by Reverse Transcriptase Inhibition

To verify, that the observed titers of the above described MeV pseudotyped HIV-1 vector particles were not due to pseudotransduction, which means protein transfer from the producer cells to the target cells, but due to viral gene transfer, HT1080 cells were transduced by the above described MeV pseudotyped HIV-1 vector particles either in the presence or absence of the reverse transcriptase inhibitor azido-thymidine (AZT). In the presence of AZT reverse transcription of the transfer vector will be prevented and thus GFP expression blocked in the transduced cells. Transfer of GFP protein in contrast will not be inhibited.

1.0*10$^5$ HT1080 cells were seeded per well of a 24-well plate. On the next day, one hour before transduction, half of the cells were incubated with medium containing 10 μM of the reverse transcriptase inhibitor azido-thymidine (AZT).

Meanwhile, the concentrated HIV-1 vector particles pseudotyped with the modified MeV H and F proteins were serially diluted in 1:10 steps in medium containing 10 μM AZT and in AZT-free medium, respectively. A total of 180 μl of the dilutions, including 1.44 μg polybrene were then added per well to the AZT pre-incubated and unincubated cells, respectively. After 2.5-3 h the transduction mixture was replaced by 1 ml of fresh medium with or without AZT. After 48-72 h the titers were calculated as described above. The titer reduction in the presence of AZT is depicted in FIG. 13.

As the titers of the HIV-1 vector particles pseudotyped with the modified MeV glycoproteins decreased by 90% to 97% in the presence of AZT (s. FIG. 13), pseudotransduction can be excluded.

Example 3: Titration of Lentiviral Vector Particles Using HEK-293T, U-87MG, A301 and A-431 Cells To determine, whether other cells but HT1080 could efficiently and specifically be transduced by the pseudotyped lentiviral vector particles of the present invention, a set of further titration experiments using four further cell lines was carried out. Four representatives of the pseudotyped lentiviral vector particles of Example 2 were tested and titration was carried out as described before. For the transduction of HEK-293T cells (in DMEM with 4.5 g/l glucose, 3.7 g/l NaHCO$_3$, 10% FCS, 1% glutamin, 0.5% penicillin/strepromycin) and U-87MG cells (in MEM with 0.85 g NaHCO$_3$/l, 1 ml/100 ml glutamin, 1 ml/100 ml not essential amino acids, 10 ml/100 ml FCS, 1 ml/30 ml bicarbonate, 1 ml/100 ml pyruvate), $1.5 \times 10^5$ and $7.2 \times 10^4$ cells per well of a 24 well plate were used. For the transduction of A301 cells (in RPMI 1640 with 2 g/l NaHCO$_3$, 10% FCS, 1% glutamin), A-431 cells (in DMEM with 4.5 g/l glucose, 3.7 g/l NaHCO$_3$, 10% FCS, 1% glutamin, 0.5% penicillin/strepromycin) and CHO-K1 cells (in DMEM with 4.5 g/l glucose, 3.7 g/l NaHCO$_3$, 10% FCS, 1% glutamin, 0.5% penicillin/strepromycin) $1.0 \times 10^5$, $1.25 \times 10^5$ and $7.5 \times 10^4$ cells per well of a 24 well plate were used. Otherwise the same conditions as for the HT1080 cells were used.

The titers of the suspension cell line A301 were just determined by FACS analysis. For this purpose the cells of a well with an adequate dilution were centrifuged as described in Experiment 2. The pellet was resuspended in FACS washing buffer and centrifuged as above. This step was repeated once more and the pellet was then resuspended in 200 μl PBS/1% paraformaldehyde. Otherwise the same procedure as described in Experiment 2.

Table 2 summarizes the results of the transduction of HEK-293T, U-87MG, A301 and A-431 cells using the pseudotyped lentiviral vector particles.

TABLE 2

Titers of MV F/H pseudotyped HIV-1 vector particles

| F/H variants | t.u./ml 293T[2] | t.u./ml U-87MG[2] | t.u./ml A301[2] | t.u./ml A-431[2] | t.u./ml CHO-K1[2/3] |
|---|---|---|---|---|---|
| $F_{wt} H_{wt}$ | 0 | 0 | — | — | 0 |
| FcΔ24 HcΔ14 | $2.9 * 10^3$ | $3.42 * 10^3$ | — | — | 0 |
| FcΔ30 HcΔ18 | $1.0 * 10^6$ | $\geq 1 * 10^{6\#}$ | $6.0 * 10^4$ | $3.9 * 10^{5+}$ | 0 |
| FcΔ30 HcΔ19 | $2.0 * 10^5$ | $\geq 1 * 10^{6\#}$ | $1.98 * 10^5$ | — | 0 |
| FcΔ30 HcΔ24 + 4A | $1.6 * 10^6$ | $\geq 1 * 10^{6\#}$ | — | — | 0 |
| pos. control: VSV-G | — | — | — | — | $1.1 * 10^8$ |
| neg. control: MLV Env$_{eco}$ | $60.0^+$ | $0^+$ | 0 | $8.4 * 10^{2+}$ | 90 |

[2]concentrated cell supernatants were used
[3]CHO-K1 cells do not express CD46 and SLAM
+average of 2 experiments
titers could not be calculated exactly
— experiment not carried out All cell lines but A301 only express CD46, A301 cells express CD46 and SLAM. Therefore, also various other cell types, at least carrying one of the two cell markers CD46 and SLAM, respectively, could be specifically transduced using the pseudotyped lentiviral vector particles of the present invention. Again, CHO-K1 cells neither displaying CD46 nor SLAM on their surface are not transduced by the presently disclosed pseudotyped lentiviral vector particles.

Example 4: Effect of the Ratio F:H on Transduction Efficiency

A series of experiments was carried out in order to determine, whether the ratio of F protein to H protein, incorporated into the pseudotyped lentiviral vector particles, has any effect on the transduction efficiency of said vector particles.

Pseudotyped lentiviral vector particles were basically generated as described in Example 2. However, the amount of plasmids pCG-HcΔ19 and pCG-FcΔ30 was varied. Briefly, HEK-293T cells were co-transfected with 6.72 μg packaging plasmid encoding HIV-1 gag/pol, 11.27 μg transfer plasmid encoding GFP and different amounts of the two plasmids encoding the HcΔ19 and FcΔ30 protein, respectively, e.g. 1 μg pCG-HcΔ19 and 7 μg pCG-FcΔ30. This was carried out by calcium phosphate transfection as described in Example 2. About 48 h after the transfection the cell supernatants, that contain the HcΔ19/FcΔ30 protein pseudotyped HIV-1 vectors were filtrated and used for the transduction of HT1080 cells as described in Example 2.

Table 3 summarizes the results of the HT1080 cell transduction experiments using the presently disclosed pseudotyped lentiviral vector particles having different ratios of F:H protein. The titer of the vector particles resulting from the transfection with the same amount of pCG-HcΔ19 and pCG-FcΔ30 plasmid was set as 100%. Other titers were then normalized to this value.

TABLE 3

Relative titers of HcΔ19/FcΔ30 pseudotyped HIV-1 vector particles using different amounts of pCG-HcΔ19 and pCG-FcΔ30 plasmid for vector particle production

| Amount of pCG-HcΔ19 [µg] | Amount of pCG-FcΔ30 [µg] | relative titer [%] |
|---|---|---|
| 4 | 4 | 100 |
| 5.5 | 2.5 | 0.16 |
| 6 | 2 | 0.08 |
| 7 | 1 | 0.39 |
| 7.8 | 0.2 | 0.47 |
| 3 | 5 | 106 |
| 2.5 | 5.5 | 494 |
| 2 | 6 | 514 |
| 1 | 7 | 2157 |
| 0.6 | 7.4 | 471 |
| 0.2 | 7.8 | 5.41 |

These results clearly demonstrate that the titer of the vector particles directly corresponds to the ratio of F:H plasmid used for the production of the vector particles, and thus directly corresponds to the ratio of F:H protein actually incorporated into the pseudotyped lentiviral vector particles. It is apparent that the titer can be drastically increased by an enhanced F protein concentration as incorporated into the resulting vector particles. A ratio of 7:1 (F:H protein) unexpectedly yielded especially good results.

Example 5: Cell Entry Targeted Lentiviral Vector Particles Directed to CD20-expressing Cells In the following series of experiments, the ability of the pseudotyped vector particles to target cells displaying certain surface markers (e.g. cell surface markers like clusters of differentiation, or receptors) other than CD46 and SLAM was investigated. The vector particles used for these studies were pseudotyped with a truncated F protein and further comprised a truncated, mutated, and chimeric fusion H protein that exemplarily displayed a single chain antibody against CD20 or the EGF ligand (Example 6) as its ectodomain. The mutation of the MeV H protein comprised the four point mutations Y481A, R533A, S548L and F549S which hinders productive interactions with CD46 and SLAM, respectively.

Thus, such pseudotyped lentiviral vector particles were not expected to successfully enter the cells via CD46 and SLAM, but rather to be targeted to and enter only those cells displaying the respective corresponding markers at their surface.

The pseudotyped lentiviral vector particles were generated as described in Example 2. Briefly, HEK-293T cells were co-transfected with the packaging plasmid encoding HIV-1 gag/pol, the transfer plasmid encoding GFP, and the two plasmids encoding HmutscFvCD20Δ18, HmutscFvCD20Δ19 and HmutscFvCD20Δ24+4A, respectively, and FcΔ30. After 48h the cell supernatant, containing the pseudotyped HIV-1 vector particles, was filtrated, concentrated, and then used for the transduction of HT1080-CD20 and HT1080 cells. HT1080-CD20 cells stably express human CD20. As positive and negative controls, concentrated cell supernatant from HEK-293T cells co-transfected with the packaging plasmid, the transfer plasmid, and the plasmid encoding VSV-G and MLV Enveco, respectively, was used.

FIGS. 8A-8F present the results of these experiments: While CD46 and SLAM expressing HT1080 cells are not transduced by the vector particles pseudotyped with HmutscFvCD20Δ19 and FcΔ30 (FIG. 8B), a clear and efficient transduction of HT1080-CD20 cells, additionally expressing CD20, is clearly evident (FIG. 8A). FIGS. 8C-F show the positive and negative controls of the experiment (FIG. 8C: positive control using HT1080-CD20 cells; FIG. 8D positive control using HT1080 cells; FIG. 8E negative control using HT1080-CD20 cells; FIG. 8F negative control using HT1080 cells).

Furthermore, the titers of three different HmutscFvCD20/FcΔ30 pseudotyped vector particles were determined for HT1080-CD20 cells in comparison to the HT1080 cells. Vector particles pseudotyped with FcΔ30 and HmutscFvCD20Δ18, HmutscFvCD20Δ19 and HmutscFvCD20Δ24+4A, respectively, were generated and tested on HT1080-CD20 and HT1080 cells as described above. Table 4 summarizes the result of these experiments.

TABLE 4

Titers of HIV-1 vector particles pseudotyped with HmutscFvCD20Δ18/FcΔ30, HmutscFvCD20Δ19/FcΔ30 and HmutscFvCD20Δ24 + 4A/FcΔ30, respectively, on HT1080 and HT1080-CD20 cells.

| envelope proteins | HT1080-CD20+ [t.u./ml]++ | HT1080 [t.u./ml]++ |
|---|---|---|
| HmutscFvCD20Δ18/FcΔ30 | $2.0 * 10^5$ | $9.8 * 10^2$ |
| HmutscFvCD20Δ19/FcΔ30 | $1.32 * 10^6$ | $3.9 * 10^3$ |
| HmutscFvCD20Δ24 + 4A/FcΔ30 | $8.6 * 10^3$ | $2.0 * 10^2$ |
| positive control: VSV-G | $6.9 * 10^9$ | $1.8 * 10^{10}$ |
| negative control: MLV $Env_{eco}$ | $4.8 * 10^2$ | $1.46 * 10^3$ |

+HT1080 cells that stably express human CD20

++titers of one experiment; concentrated cell supernatants were used

These results thus establish that lentiviral vector particles pseudotyped with a truncated MeV F protein and a fusion construct of a truncated and mutated MeV H protein displaying a single chain antibody at its ectodomain only enter those cells expressing the respective cell marker to the single chain antibody. In the present experiment, the vector particles pseudotyped with HmutscFvCD20Δ18, HmutscFvCD20Δ19, or HmutscFvCD20Δ24+4A, respectively, and FcΔ30 can effectively transduce those cells expressing CD20, however, titers and transduction are significantly reduced for cells not expressing CD20. Furthermore, transduction occurs irrespective of expression of either CD46 or SLAM by the targeted cell.

Selective Transduction of Lymphocytes that Naturally Express CD20 by HmutscFvCD20Δ18/FcΔ30 Pseudotyped HIV-1 Vector Particles.

Also lymphocytes, naturally expressing CD20, can be selectively and efficiently transduced by the anti-CD20 targeting vector particles. The above described HIV-1 particles, pseudotyped with HmutscFvCD20Δ18 and FcΔ30 were used for the transduction of CD20 positive Daudi cells (B cell line; ECACC 85011437) and CD20 negative K-562 cells (myeloid cell line; ATCC CCL-243). As positive control VSV-G pseudotyped HIV-1 vector particles were used for the transduction of these two cell lines.

For the transduction of the two cell lines an MOI of 0.5 was used (VSV-G pseudotyped vector particles: MOI 2). For pre-coating, one half of the concentrated HmutscFvCD20Δ18/FcΔ30 or VSV-G pseudotyped HIV-1 vector particles was diluted in 120 μl medium (RPMI 1640 with 2 g/l $NaHCO_3$, 10% FCS, 1% glutamine) and transferred to a single well of a fibronectin coated 48-well plate. This plate was then centrifuged by 860 g for 20 min at 4° C. Meanwhile the other half of the vector particles was diluted in 180 µl medium (supplemented with 1.2 µg protamine sulfate) containing 1*10⁵ Daudi (CD20+) or K-562 (CD20–) cells and added to the wells with the respective pre-coated vector particles. A centrifugation step at 860 g for 1 h at 32° C. followed. After further 2 h incubation at 37° C. in the incubator, 700 µl medium per well were added. The GFP fluorescence of transduced cells was detected by FACS (BD FACSCalibur; s. FIG. 14) 72 h after transduction.

Figure 14D:
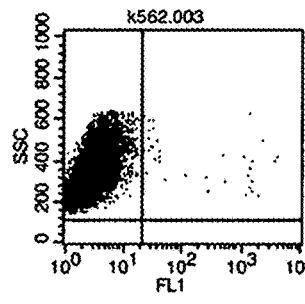

Whereas the VSV-G pseudotyped HIV-1 vector particles transduced both cell lines efficiently (s. FIG. 14A-14C), the HmutscFvCD20Δ18/FcΔ30 pseudotyped HIV vector particles selectively transduced CD20 positive Daudi cells (FIG. 14B), whereas the CD20 negative K-562 cells remained largely GFP negative (s. FIGS. 14C-14D). Accordingly, also cells that do naturally express the targeted receptor can be selectively transduced by the targeting vectors. Remarkably, the CD20 positive lymphocytes were transduced by the anti-CD20 targeting vector particles, at a similar efficiency as with the VSV-G pseudotyped vector particles.

Long-Term Cultivation of Transduced Cells

To verify the stability of the gene transfer by the targeting vectors, concentrated HmutscFvCD20Δ18/FcΔ30 pseudotyped HIV-1 vector particles (MOI 0.1) were added together with 4.0 μg protamine sulfate to 2*$10^5$ CD20 positive Raji cells (B cell line; ATCC CCL-86; RPMI 1640 with 2 g/l $NaHCO_3$, 10% FCS, 1% glutamine) in a single well of a 24-well plate resulting in 1 ml transduction mixture. Then this plate was centrifuged at 860 g for 1 h at 32° C.

The transduced cells were then cultivated for 19 days at 37° C. At different time points the percentage of GFP positive cells was determined by FACS analysis (Dako Galaxy flow cytometry system; s. FIG. 15). The data demonstrate that the level of GFP positive cells remained between 17% and 32% over the whole period of 19 days (s. FIG. 15), thus confirming the stability of gene transfer mediated by the anti-CD20 targeting vector particles.

Example 5.2: Effect of the Ratio HmutscFvCD20Δ18:FcΔ30 on Transduction Efficiency A series of experiments was carried out in order to determine, whether the ratio of FcΔ30 protein to HmutscFvCD20Δ18 protein, incorporated into the pseudotyped lentiviral vector particles, has the same effect on the transduction efficiency of said vector particles as demonstrated in Example 4 for the FcΔ30 to HcΔ19 ratio.

Pseudotyped lentiviral vector particles were basically generated as described in Example 5. However, the amount of plasmids pCG-HmutscFvCD20Δ18 and pCG-FcΔ30 was varied. Briefly, HEK-293T cells were co-transfected with 6.72 μg packaging plasmid encoding HIV-1 gag/pol, 11.27 μg transfer plasmid encoding GFP and different amounts of the two plasmids encoding the HmutscFvCD20Δ18 and FcΔ30 protein, respectively, e.g. 2 μg pCG-HmutscFvCD20Δ18 and 6 μg pCG-FcΔ30. This was carried out by calcium phosphate transfection as described in Example 2. About 48 h after the transfection the cell supernatants, containing the different HmutscFvCD20Δ18/FcΔ30 protein pseudotyped HIV-1 vector particles were filtrated and used for transduction of HT1080-CD20 cells as described in Example 5.

FIG. 16 summarizes the results of the HT1080-CD20 cell transduction experiments using the presently disclosed pseudotyped lentiviral vector particles produced with the indicated ratios of pCG-HmutscFvCD20Δ18 and pCG-FcΔ30. The titer of the vector particles resulting from the transfection with the same amount of pCG-HmutscFvCD20Δ18 and pCG-FcΔ30 plasmid was set as 100%. Other titers were then normalized to this value.

These results clearly demonstrate that the titer of the vector particles directly corresponds to the ratio of HmutscFvCD20Δ18:FcΔ30 plasmid used for the production of the vector particles, and thus directly corresponds to the ratio of HmutscFvCD20Δ18:FcΔ30 protein actually incorporated into the pseudotyped lentiviral vector particles. It is apparent that the titer can be increased by an enhanced FcΔ30 protein incorporation into the resulting vector particles. A ratio of 1:3 HmutscFvCD20Δ18:FcΔ30 protein yielded especially good results (s. FIG. 16). But in comparison to the results from the titration of HcΔ19:FcΔ30 described in Example 4, relatively more H protein is needed when a single chain antibody is fused to its ectodomain. Thus, titers of targeting vectors can be optimised by titrating the ratio for any H protein variant displaying a new type of single chain antibody or other polypeptide.

Example 5.3: Targeted Gene Transfer to SLAM Positive Cells Using HIV-1 Vector Particles Pseudotyped with the Modified Glycoproteins of a Measles Virus Wild Type Strain For the targeting of SLAM expressing cells HIV-1 vector particles that were pseudotyped with the modified glycoproteins of the wild type measles virus 323, a molecular clone of the IC-B strain, were used. This measles virus stain can only enter through SLAM but not through CD46 (Takeda et al. 2000, J Virol 74 (14) p. 6643-6647).

Upon truncation of the cytoplasmic tails of the wild type F and H proteins (identical cytoplasmic tail sequence as the Edmonston strain F/H proteins) as described in Example 1 pseudotyping of HIV-1 particles became possible.

The pseudotyped lentiviral vector particles were generated as described in Example 2. Briefly, HEK-293T cells were co-transfected with 6.72 μg packaging plasmid encoding HIV-1 gag/pol, 11.27 μg transfer plasmid encoding GFP, 1.0 μg plasmid encoding HwtΔ18 and 7.0 μg plasmid encoding FwtΔ30. This was carried out by calcium phosphate transfection as described in Example 2. After 48h the cell supernatants, containing the pseudotyped HIV-1 vector particles, were filtrated, concentrated (as described in Example 2), and then used for the transduction of a mixture of SLAM positive Raji and SLAM negative HT1080 cells.

For transduction 1.0×$10^5$ HT1080 and the same amount Raji cells were seeded into a single well of a 24-well plate. On the next day, the vector particle stocks were diluted 1:10, 1:50 and 1:500 and a total of 300 μl of the dilutions, including 1.2 μg protamine sulfate were added to the cell mixture. A centrifugation step at 860 g for 1 h at 32° C. followed. Then 700 μl medium (RPMI 1640 with 2 g/l $NaHCO_3$, 10% FCS, 1% glutamine) per well were added. 48 h after transduction the Raji cells were removed from the HT1080 cell layer and transferred into a reaction tube. The HT1080 cells were detached from the plate by incubation with 100 μl PBS-Trypsin solution and transferred into another reaction tube. The transduction pattern was then determined by measuring the GFP and CD20 positive cells by FACS. For this purpose cells were centrifuged for 2 min at 3.500 rpm (Biofuge fresco Heraeus instruments) at 4° C. The pellets were then resuspended in 1 ml FACS washing buffer (PBS, 1% FCS, 0.1% $NaN_3$) and centrifuged as above. Next, the pellets were incubated for 1 h at 4° C. in an appropriate dilution of anti-CD20 antibody (anti-human CD20 clone B9E9, Sigma-Aldrich, Taufkirchen, Germany). Afterwards the cells were centrifuged as above, washed twice with FACS washing buffer and incubated for 1 h at 4° C. in the dark in an appropriate dilution of anti-mouse IgG second antibody directly coupled to the fluorophore R-Phycoerythrin (PE) (anti-mouse IgG-PE F(ab')$_2$ Fragment, Sigma-Aldrich, Taufkirchen, Germany). Afterwards the cells were centrifuged as above, washed twice with FACS washing buffer and resuspended in 200 μl PBS/1% paraformaldehyde. Then the CD20 and GFP positive cells were measured by FACS (s. FIG. 17A-17F).

Figures 17A, 17B, 17C, 17D, 17E, 17F:
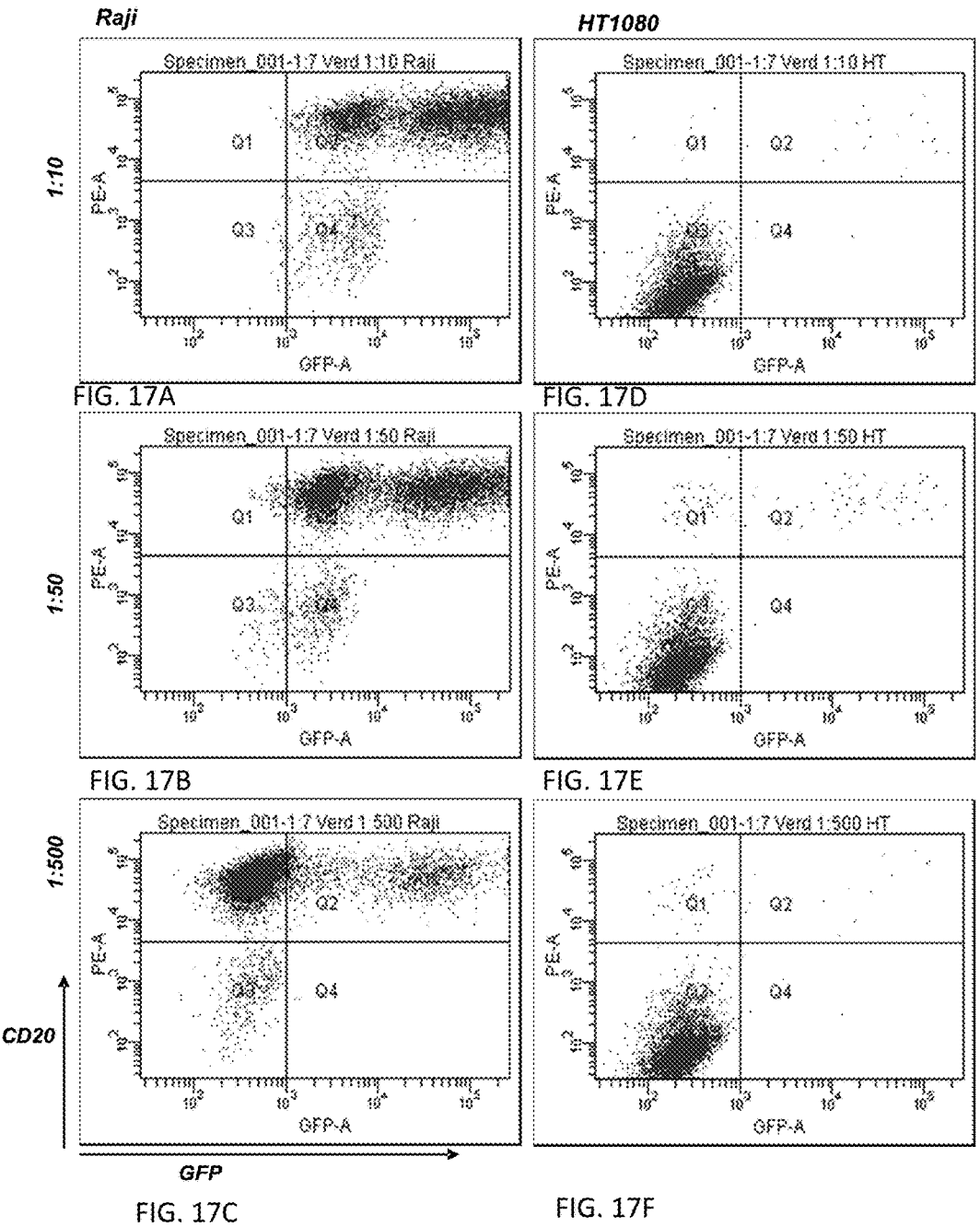

The FACS data show that the Raji and HT1080 cells had been successfully separated as in the Raji cell fraction nearly all cells were CD20 positive (s. FIG. 17A-17C), whereas in the HT1080 cell fraction nearly all cells were CD20 negative (s. FIG. 17D-17F). As demonstrated in FIG. 17B effectively all of the Raji cells were transduced by the HwtΔ18/FwtΔ30 pseudotyped HIV-1 vector particles also at the 1:50 dilution. In contrast, there were virtually no GFP positive HT1080 cells detectable (FIG. 17E). Only a few contaminating CD20+ cells were detectable (.). These data demonstrate that human lymphocytes can be efficiently transduced with HIV-1 vector particles pseudotyped with H and F proteins of a wildtype measles virus strain.

Example 6: Cell Entry Targeted Lentiviral Vector Particles Directed to EGFR-Expressing Cells In the following series of experiments, the ability of the vector particles to target cells displaying certain markers other than CD46 and SLAM was investigated using a second set of pseudotyped vector particles. The vector particles used for these studies were produced in a manner similar to those vector particles described in Example 5; however, they instead comprised a mutated and chimeric fusion H protein that exemplarily displayed the EGF ligand as its ectodomain.

Specifically, vector particles pseudotyped with FcΔ30 and HmutEGFΔ18, HmutEGFΔ19 and HmutEGFΔ24+4A, respectively, were generated and tested on A-431, CHO-hSLAM and CHO-BCl cell lines. A431 cells serve as a positive control for EGFR as they express high levels of EGFR. CHO-hSLAM and CHO-BCl cells stably express human SLAM and CD46, respectively. Table 5 summarizes the result of these experiments.

TABLE 5

Titers of HIV-1 vector particles pseudotyped with HmutEGFΔ18/FcΔ30, HmutEGFΔ19/FcΔ30 and HmutEGFΔ24 + 4A/FcΔ30, respectively, on A431, CHO-hSLAM and CHO-BC1 cells

| envelope proteins | A-431 [t.u./ml]$^{++}$ | CHO-hSLAM$^1$ [t.u./ml]$^{++}$ | CHO-BCl$^2$ [t.u./ml]$^{++}$ |
|---|---|---|---|
| HmutEGFΔ18/FcΔ30 | $2.7 * 10^{5+}$ | $2.8 * 10^{2+}$ | 0 |
| HmutEGFΔ19/FcΔ30 | $2.2 * 10^4$ | $1.6 * 10^2$ | 0 |
| HmutEGFΔ24 + 4A/FcΔ30 | $5.8 * 10^4$ | $9.6 * 10^2$ | $8 * 10^2$ |
| positive control: VSV-G | $3.9 * 10^{9+}$ | $5.7 * 10^{9+}$ | $9.3 * 10^9$ |
| negative control: MLV Env$_{eco}$ | $8.4 * 10^{2+}$ | $1.2 * 10^{3+}$ | $2.2 * 10^3$ |

$^1$CHO cells that stably express human SLAM
$^2$CHO cells that stably express human CD46
$^+$average of 2 experiments
$^{++}$concentrated cell supernatants were used According to the results of Example 5, the second set of pseudotyped cell entry targeted vector particles also markedly and specifically transduced the target cells. Thus, the vector particles pseudotyped with HmutEGFΔ18, HmutEGFΔ19, or HmutEGFΔ24+4A, respectively, and FcΔ30 can effectively transduce cells expressing the EGF-receptor as a cell marker. Notably, both titers and transduction are significantly reduced for cells not expressing this receptor.

To summarize, the lentiviral vector particles of the invention, when pseudotyped with a truncated MeV F protein and a fusion construct of a truncated and mutated MeV H protein displaying a single chain antibody, or a ligand to a cell marker at its ectodomain, specifically enter cells expressing the respective cell marker to the single chain antibody or the ligand. The vector particles of the present invention thus effectively enter and transduce cells expressing the corresponding marker proteins, and the titers and thus the transduction are highly reduced on cells not expressing these cell markers. Therefore, cell entry targeted transduction using the lentiviral vector particles of the present invention was clearly demonstrated to be a particularly effective tool for highly selective gene transfer into specific cells.

Example 7: Cell Entry Targeted Lentiviral Vector Particles Directed to CD34 Expressing Cells In the following series of experiments the ability to target cells displaying specific markers other than CD46 and SLAM was investigated using a third set of pseudotyped vector particles. They comprise a mutated and chimeric fusion H protein that exemplarily displays the scFvCD34 as its ectodomain, i.e. a single chain antibody directed against the CD34 molecule.

The scFvCD34 DNA is PCR-amplified from cDNA, which is reverse transcribed from mRNA extracted from the Hybridoma cell line anti-My-10 (ATCC HB-8483) producing a monoclonal antibody against CD34. The amplification is performed according to the protocol of the mouse scFv Module/Recombinant Phage Antibody System (Amersham Biosciences) whereas a SfiI and NotI restriction site, respectively, is introduced at the N and the C terminal coding region, respectively. This way the scFvCD20 coding region in the plasmid pCG-HmutscFvCD20Δ18 can be replaced by the scFvCD34 DNA. For this purpose the scFvCD34 and plasmid DNA is cleaved with the SfiI and NotI restriction enzymes (commercially available at NEB) in an appropriate buffer 5 h at 37° C. and 3 h at 50° C. The adjacent cloning steps are described in Example 1.

The pseudotyped lentiviral vector particles are basically generated as described in Example 2. Briefly, HEK-293T cells are co-transfected with the packaging plasmid encoding HIV-1 gag/pol, the transfer plasmid encoding GFP and the two plasmids encoding HmutscFvCD34Δ18 and FcΔ30, respectively. After 48 h the cell supernatant, that contains the pseudotyped HIV-1 vectors, is filtrated, concentrated and used for the transduction of KG-la cells, expressing CD34 at their cell surface and A301 cells, expressing CD46 and SLAM but not CD34. The transduction is basically done as described in Experiment 3. As positive and negative controls, concentrated cell supernatant from HEK-293T cells co-transfected with the packaging plasmid, the transfer plasmid and the plasmid encoding VSV-G and MLV Enveco, respectively, is used.

For analysis of the gene transfer, the transduced cells will be analysed for GFP fluorescence and for CD34 antigen expression by FACS analysis. In accordance with the results of Example 5 and 6, also the third set of pseudotyped cell entry targeted vector particles should highly specifically transduce the target cells. Thus, the vector particles pseudotyped with HmutscFvCD34Δ18 and FcΔ30 should transduce cells expressing CD34 but titers and transduction should be highly reduced on cells not expressing said surface marker. It is thus expected, that CD46 and SLAM expressing A301 cells remain untransduced by the vector particles pseudotyped with HmutscFvCD34Δ18 and FcΔ30 proteins while a clear and efficient transduction of the CD34-positive KG-1a cells will become evident.

CD34 is a stem cell marker which is currently used to isolate and purify hematopoietic stem cells. In another experiment primary cells are targeted using human leucapheresis cells, which contain less than 1% CD34 positive hematopoietic stem cells. For this purpose the leucapheresis cells are transduced with the HmutscFvCD34Δ18 and FcΔ30 pseudotyped vector particles. 48 h later the cells are stained for CD34 expression using an antibody directed against CD34 directly coupled to an appropriate fluorophore. For this purpose the transduced cells are centrifuged for 2 min by 3.500 rpm (Biofuge fresco Heraeus instruments) at 4° C. The pellet is then resuspended in 1 ml FACS washing buffer (PBS, 2% FCS, 0.1% $NaN_3$) and centrifuged as above. Next, the pellet is incubated for 1 h at 4° C. in the dark in an appropriate dilution of the anti-CD34 antibody. Afterwards the cells are centrifuged as above and washed twice with FACS washing buffer. Then the cells are resuspended in 200 μl PBS/1% paraformaldehyde and analyzed by FACS for GFP and CD34 expression. It is expected, that only CD34-positive cells will be GFP positive, whereas all other types of blood present in the leucapheresis cells remain untransduced.

To demonstrate that the transduced cells were indeed hematopoietic stem cells having the capability of differentiating into all types of blood cells, a bone marrow reconstitution experiment will be performed. For this purpose, SCID mice will be lethally irradiated and then transplanted with the transduced CD34-positive cells. Starting at 3.5 weeks after transplantation and continuing for at least 16 weeks after transplantation, peripheral blood will be collected from the tail vein and analyzed by FACS for GFP expression. It is expected, that most of the blood cells have been reconstituted from the transduced CD34-positive cells which can be followed by the GFP marker gene.

Thus, also a third set of pseudotyped vector particles, comprising a mutated and chimeric fusion H protein that exemplarily displays the scFvCD34 as its ectodomain, can be used as an effective tool for highly selective gene transfer into specific cells.

Example 8: Targeted Cell Killing by Using Lentiviral Vector Particles Directed to CD20 Expressing Cells The described experiment demonstrates that by using the targeted lentiviral vector particles of this invention it is possible to specifically kill target cells in a mixture of different cells.

The vector particles used for this experiment were pseudotyped with a truncated F protein and further comprised a truncated mutated and chimeric fusion H protein that exemplarily displayed a single chain antibody against CD20 as its ectodomain. The mutation of the MeV H protein comprises the four point mutations Y481A, R533A, S548L and F549S which ablates productive interactions with CD46 and SLAM, respectively. For the cell killing, these vector particles have packaged a gene coding for a fusion protein of a hypersensitive mutant of the herpes simplex virus thymidine kinase (TK39) and a cytoplasmic truncated version of the cell surface antigen CD34 (CD34TK39). The thymidine kinase metabolises the inactive drug Gancyclovir into a chemical derivate, which is toxic for dividing cells. Furthermore, transduced cells can be detected by CD34 expression. In parallel, as a control, the same vector particles having packaged the go gene were applied.

For the generation of the vector particles calcium phosphate transfection was performed. 24 h before transfection, $6.5*10^6$ HEK-293T cells were seeded into a T75 flask. 1 h before transfection the medium of the cells was exchanged against 7 ml fresh medium (DMEM with 4.5 g/l glucose, 3.7 g/l $NaHCO_3$, 10% FCS, 1% glutamin). 2.0 μg of the plasmid encoding HmutscFvCD20Δ18 and 6.0 μg of the plasmid encoding FcΔ30 were co-transfected with 6.72 μg of packaging plasmid and 11.27 μg of transfer plasmid. Whereas the latter was either SEW or S-CD34TK39-W, in which the gfp gene of SEW was replaced by the cd34tk39 gene derived from the plasmid M71tCD34tk39m (Junker et al. 2003, Gene Therapy 10 p. 1189-1197). The plasmid DNA was filled up with $H_2O$ (Sigma-Aldrich, Taufkirchen, Germany) to 450 μl. Then 50 μl 2.5 M $CaCl_2$ (Sigma-Aldrich, Taufkirchen, Germany) solution were added. While vortexing the DNA-$CaCl_2$ solution, 500 μl 2×HBS Buffer (281 mM NaCl; 100 mM HEPES; 1.5 mM $Na_2HPO_4$ (Sigma-Aldrich, Taufkirchen, Germany)) were added dropwise. The suspended precipitate was then transferred to the HEK-293T cells. After about 17 h incubation the medium was replaced with 12 ml fresh medium. 24 h afterwards, the 12 ml cell supernatant, containing the pseudotyped lentiviral vector particles, were filtered (0.45 μm filter) and concentrated by centrifugation at 3063 g and 40° C. for at least 24 h. The pellet was resuspended in 120 μl FCS-free medium and used for the transduction of a mixture of CD20 positive Raji (ATCC CCL-86) and CD20 negative K-562 (ATCC CCL-243) cells.

The HmutscFvCD20Δ18/FcΔ30 pseudotyped HIV-1 vector particles either with packaged go gene or with packaged cd34tk39 gene were 1:5 diluted in 300 μl medium (RPMI 1640 with 2 g/l $NaHCO_3$, 10% FCS, 1% glutamine) containing a mixture of $2*10^3$ CD20+ Raji and $2*10^3$ CD20− K-562 cells. This transduction mixture including also 1.2 μg protamine sulfate was transferred to a single well of a 48-well plate and was then centrifuged at 860 g for 1 h at 32° C. After further 2 h incubation at 37° C., 700 μl medium per well were added. Five days after transduction, gfp transduced cells were stained against CD20 (mouse anti-human CD20/PE-Cy5; BD Pharmingen™, Heidelbeg, Germany) and cd34tk39 transduced cells against CD20 and CD34 (mouse anti-human CD34/PE; EuroBioSciences GmbH, Friesoythe, Germany). For this purpose the cells were centrifuged for 2 min at 3.500 rpm (Biofuge fresco Heraeus instruments) at 4° C. The pellets were then resuspended in 1 ml FACS washing buffer (PBS, 1% FCS, 0.1% $NaN_3$) and centrifuged as above. Next, the pellets were incubated for 1 h at 4° C. in the dark in an appropriate dilution of anti-CD20 (cells transduced by the vector particles with packaged gfp gene) or anti-CD20 and anti-CD34 (cells transduced by the vector particles with packaged cd34tk39 gene) antibody directly coupled to an appropriate fluorophore. Afterwards the cells were centrifuged as above, washed twice with FACS washing buffer and resuspended in 200 μl PBS/1% paraformaldehyde. Afterwards the percentages of CD20/GFP and CD20/CD34 double positive cells, respectively, were measured by FACS (time point 0 h in FIG. 18). Next, half of the transduced cells were incubated in 10 μM Gancyclovir (GCV; Cymeven, Roche) containing medium (exchange with fresh GCV containing medium every 24 h)

while the other half was left as control in GCV-free medium. At different time points the cells were stained with the respective antibodies and the double positive cells were measured by FACS (Dako Galaxy flow cytometry system; s. FIGS. 18A-18B).

FIG. 18 shows, that using the anti-CD20 targeting vector particles either with packaged gfp gene (FIG. 18A) or with packaged cd34tk39 gene (FIG. 18B), the CD20 positive cell fraction was selectively transduced. There were about 20% CD20/GFP and 30% CD20/CD34 double positive cells whereas only about 1-2% CD20 negative cells were transduced. Over the time, there was no great change in the transduction pattern visible, demonstrating the stable integration of the transferred genes and the viability of transduced cells. It is also verified that the transduced cells had no growth advantage or disadvantage. As expected, the GCV incubation had no influence on the CD20/GFP double positive cell fraction, demonstrating that GCV by its own had no toxic effect on the cells. In contrast, the CD20 positive cell fraction transduced with the CD34TK39 fusion protein was very efficiently and selectively killed by the GCV incubation (s. FIG. 18b). From about 30% double positive cells at the beginning only about 12% were left after 48 hours and after 6 days nearly all double positive cells were killed.

Thus, the pseudotyped vector particles of the invention are an effective tool to selectively kill specific target cells in a mixture of different cells. Preferably, the pseudotyped vector particles of the invention can thus be used for cancer therapy, as e.g. Burkitt lymphoma.

Moreover, selective killing of CD20 positive tumor cells can be demonstrated in vivo in a murine tumor model. For this purpose, SCID-X1 mice will be injected subcutaneously with $1 \times 10^6$ HT1080 cells on their left flank and $1 \times 10^6$ HT1080-CD20 cells on their right flank. About one week later, $10^8$ CD20-directed pseudotyped vector particles will be injected intravenously, followed by daily systemic injection of Gancyclovir. Tumor growth will be followed daily by determining the tumor volume. It is expected that the CD20 positive tumor will be significantly inhibited in cell growth while the CD20-negative tumor will grow unaffectedly.

Example 9: Identification of AMPA Receptor Positive Neurons in Hippocampal Slices Under Live Conditions In neurobiology protocols for organotypic slice cultures from mouse brain are well established that allow cultivation of the complete slices for several weeks and analysis of single cells within the tissue, as e.g. electrophysiology recordings. So far no method is available to identify defined types of neurons in the tissue slice under live conditions before the analysis is being performed. The selective marker gene transduction with the pseudotyped lentiviral vectors of this invention can label a single cell based on the expression of a cell surface marker of choice that is used for gene transfer.

In this example AMPA receptor positive neurons are being identified in hippocampal slice cultures. For this purpose a lentiviral pseudotype vector particle was generated that displays a scFv directed against the glutamate receptor-4 (GluR4). The single chain antibody was generated by PCR amplification of the coding regions for the light and the heavy chains of a Fab fragment directed against GluR4. This Fab fragment is encoded by the plasmid Fab7-Origami (Jespersen et al. 2000, Eur J Biochem. 267 (5) p. 1382-9). The primers Fab7VL(+) 5'-ATCCCTCGGGTGGCGGAGCTCGGACATTGTGATGACCC-3' (SEQ ID NO: 27) and Fab7VL(−) 5'-TTTTTCCTTTTGCGGCCGCAGCCCGTTTATTTC-3' (SEQ ID NO: 28) were used for the amplification of the light chain and the primers Fab7VH(+) 5'-GCTTGGCCCAGCCGGCCATGGAGGTGAAGCTGGTG-3' (SEQ ID NO: 29) and Fab7VH(−) 5'-TCCCCCGAGCCACCTCCGCCGGATCCACCGCCACCTGAGGAGACGGTGAC-3' (SEQ ID NO: 30) were used for the amplification of the heavy chain. Thus, an AvaI restriction site and a Glycin-Serin linker was introduced at the 3'end of the heavy and the 5'end of the light chain, respectively. The two fragments were ligated and cloned into the SfiI/NotI restriction sites of pCG-HmutscFvCD20Δ18 (described in Example 1), thereby replacing the single chain antibody directed against CD20 and resulting in the plasmid pHmutscFvGluR4Δ18.

The pseudotyped lentiviral vector particles were generated as described in Example 5. Briefly, 10 HEK-293T cells were co-transfected with 6.72 μg packaging plasmid encoding HIV-1 gag/pol, 11.27 μg transfer plasmid encoding GFP, 2.0 μg plasmid encoding HmutscFvGluR4Δ18 and 6.0 μg plasmid encoding FcΔ30. This was carried out by calcium phosphate transfection as described in Example 2. After 48h cell supernatants, containing the pseudotyped HIV-1 vector particles, were filtrated and concentrated, as described in Example 2.

To verify a GluR4 dependent gene transfer of these vectors, the vector particles were used for transduction of HT1080-GluR4 cells, which stably express the GluR4, and the parental HT1080 cells as control. For transduction $1.0 \times 10^5$ HT1080 cells and $1.0 \times 10^5$ HT1080-GluR4 cells were seeded into separate wells of a 24-well plate. On the next day, the vector stocks were serially diluted in 1:10 steps and a total of 250 μl of the dilutions, including 2.0 μg polybrene were then added to every well, incubated for 2.5-3h and replaced by 1 ml of fresh medium (DMEM with 4.5 g/l glucose, 3.7 g/l NaHCO$_3$, 10% FCS, 1% glutamin). After 48 h the cells were analyzed under the fluorescence microscope (FIGS. 19A-19B) and by FACS (FIGS. 19C-19E). For this purpose, cells were detached by incubation with 100 μl PBS-trypsin solution. Then 1 ml FACS washing buffer (PBS, 1% FCS, 0.1% NaN$_3$) was added and cells were then pelted by centrifugation for 2 min at 3.500 rpm (Biofuge fresco Heraeus instruments) at 4° C. Next, the pellets were incubated for 1 h at 4° C. in an appropriate dilution of anti-c-myc antibody (anti-c-myc Clone 9E10, Roche) which detects the c-myc tag at the ectodomain of the GluR4. Afterwards the cells were centrifuged as above, washed twice with FACS washing buffer and incubated for 1 h at 4° C. in the dark in an appropriate dilution of anti-mouse IgG second antibody directly coupled to the fluorophore R-Phycoerythrin (PE) (anti-mouse IgG-PE F(ab')$_2$ Fragment, Sigma-Aldrich, Taufkirchen, Germany). Afterwards the cells were centrifuged as above, washed twice with FACS washing buffer and resuspended in 200 μl PBS/1% paraformaldehyde. Then, the GluR4/GFP double positive cell population were determined by FACS.

The data demonstrate that the GluR4 targeted vectors indeed enter cells through the glutamate receptor. HT1080 cells expressing GluR4 were efficiently transduced, whereas the parental HT1080 cells that were transfected with the empty pcDNA3.1(−) plasmid (Invitrogen), therefore not expressing the receptor, could not be transduced by the anti-GluR4 targeting vector (s. FIG. 19a). The FACS data confirmed the microscopic picture. Thus, a vector targeted to an AMPA receptor is available.

Next, this vector will be used for the transduction of hippocampal slice cultures. For preparation of hippocampal slice cultures a detailed protocol has been published by Gogolla et al., 2006 (Nature Protocols 1, 1165). The hippocampal slices prepared from 6-9 day old mice are cultivated in MEM supplemented with penicillin/streptomycin, 25% inactivated horse serum, 10 mM Tris, and 25% HBSS buffer in a cell culture incubator at 35° C. and 5% $CO_2$. For transduction, $10^6$ t.u. of the vector particle stock will be added to the tissue culture and incubated over night. On the next day medium will be changed. After another 24h GFP expression in the slice culture will be analysed under the fluorescent microscope. The GFP staining pattern observed is then compared to the staining pattern obtained by immunohistochemical staining using an anti-GluR4 polyclonal antibody (rabbit anti-Glutamate receptor 4 polyclonal antibody, Chemicon). It is expected that the pattern of GFP positive cells will largely overlap with the pattern of GluR4 positive cells obtained by immunohistochemical staining.

Thus, the pseudotyped vector particles of the invention are expected to be an effective tool to identify defined cell types in cell populations, for example the tissue slices, under live conditions.

Example 10: Construction of the Library of Pseudotyped Lentiviral Vector Particles with Differing H-Single Chain Antibody Fusions The generation of the scFv library displayed on the pseudotyped lentiviral vector particles is essentially a two step procedure, including i) cloning of the plasmid library pHmutΔ19-scFvlib and ii) generation of the vector particle library. An essential prerequisite for selection of a retroviral display library is the coupling of genotype and phenotype, which in this case means that the coding region for each scFv-H fusion protein must be packaged by the vector particle having the particular scFv-H protein incorporated into its membrane. The scFv-H library must therefore be cloned into a lentiviral transfer vector, which in addition encodes a selectable marker as e.g. the neomycin-resistance gene.

Thus, a first step in cloning the library will be the construction of a lentiviral transfer vector encoding a scFv-H fusion protein and the neomycin resistance gene. As transfer vector plasmid pHGIN, which has been previously generated in our laboratory (Merten et al. 2005), can be used. In pHGIN, the retroviral Env protein coding sequence can be exchanged against the coding sequence for CD20-HmutΔ19 which can be removed from the plasmid pHmutCD20Δ19 by restriction digestion with PacI and SpeI. The resulting plasmid pHmutCD20Δ19IN serves as starting plasmid for cloning of the library.

The scFv repertoire can be subcloned from the phage display library Griffin.1, which encodes a large repertoire of synthetically diversified human single chain antibodies (Griffiths et al., 1994; EMBO J., 13, 3245-3260). About 33 μg of the plasmid DNA of this library which is available from the MRC in Cambridge (UK) will be digested with 150 U NotI and 75 U SfiI in a total volume of 225 μl in NEB buffer 2 and 1×BSA for 4h at 37° C. and 3h at 50° C. The scFv library encoding fragment will be purified from a 1.5% agarose gel with the QiaexII kit according to the manufacturer's (Qiagen) instructions, with the exception that the final elution will be performed in totally 80 μl of $H_2O$. The amount of purified fragment will be estimated on an agarose gel. In parallel, pHmutCD20Δ19IN will be digested under the same conditions with SfiI and NotI and the plasmid backbone purified by agarose gel chromatography as described for the scFv repertoire. Both DNA fragments will then be ligated in a 1:3 ratio (scFv:backbone) in a total volume of 150 μl including 2 μl T4 ligase, 18 μl PEG 8000 (40%), and 15 μl 10× Ligase buffer for 17h at 16° C. On the next morning add 10 μl T4 ligase and incubate for another 3h at 16° C. The ligation product is then purified by phenol/chloroform extraction followed by ethanol precipitation (add 15 μl 3M NaAc and 825 μl Ethanol and incubate at −20° C. overnight). The precipitated ligation product is washed in 1 ml ice-cold 70% Ethanol, dried and resuspended in 15 μl $H_2O$. For electroporation into *E. coli* bacteria (ElectroTenblue, available at Stratgene) mix 1 μl ligation with 40l electrocompetent cells and electroporate in 0.1 cm cuvettes at 1.8 kV, 25 μF, 200Ω (time constant around 4.2 ms). This procedure is repeated 10 times. After electroporation recover cells in 1 ml SOC and incubate for 1.5 h at 30° C. A small aliquot from the bacterial suspension is used to determine the number of transformed cells and thus the repertoire size that the library is covering. A minimum number of $10^7$ clones should be obtained in this step. The remaining cells are plated on large agar dishes (LB medium with kanamycin and ampicillin). On the next about 50 clones are picked and used for plasmid preparation and sequence analysis of the scFv coding regions to demonstrate the diversity of the library. The remaining colonies are scraped and resuspend into 24 ml of LB medium supplemented with ampicillin. Generate 8 glycerol stocks of 300 μl each and use the remaining bacteria to inoculate two cultures of 250 ml volume each. On the next day, the bacteria are harvested and the plasmid library is prepared using the Qiagen Maxi-Kit according to the manufacturer's instructions.

For generation of the vector particle library in a first step library producer cells are generated such that each cell will encode only a single scFv-H variant. For this purpose, approximately $7 \times 10^7$ 293T cells are transfected with plasmids pHmutΔ19-scFvlib (11.27 μg) and plasmid pCMVΔR8.9 (6.72 μg), by calcium phosphate transfection under the conditions described in Example 2 but replacing the FcΔ30 encoding plasmid by the VSV G protein encoding plasmid pMDG (8 μg). Two days post transfection the supernatant containing the pseudotype vector particle library are harvested and filtrated through a 0.45 μm filter. Polybrene is added to the filtrate to a final concentration of 8 μg/ml before it is incubated with $7 \times 10^7$ HEK293 cells for 2 h. Then, the supernatant is exchanged against fresh medium. On day two post transduction, the HEK293 cells are incubated with medium containing 1 mg/ml G418 and 20% FCS for 7 days. The surviving cells carry the genetic information for the scFv displaying lentiviral vector library which can be packaged into vector particles being released into the cell culture supernatant upon transfection of the cells with plasmids pCG-FcΔ30 and pCMVΔR8.9 (see Example 11 for details).

Example 11: Screening of CD20-Expressing HT1080 Cells Using the Library

To screen the lentiviral scFv vector particle library for antibodies directed against CD20, $5 \times 10^7$ library transduced cells, generated as described in Example 10, are seeded onto the bottom of a transwell chamber (Corning). The next day, the cells are transfected with 10 μg pCMVd8.9 and 14 μg pCG-FcΔ30 to initiate vector particle release. After one further day, $5 \times 10^6$ HT1080-CD20 cells (see Example 5) cells, seeded onto a permeable membrane the day before, are applied to the transwell chamber to initiate cocultivation with the library producer cells. After 3 days of coculture, HT1080-CD20 cells are detached from the permeable membrane by extended trypsinization (incubation for 6 min) and seeded into a T175 culture flask. After 24 h, cells are treated with neomycin containing medium for another 7 days. Surviving colonies are then used to initiate the next selection cycle by seeding them onto the bottom of a transwell chamber as described above. After the final selection round, genomic DNA from the neomycin resistant cells is prepared and the scFv coding regions are cloned and sequenced. Pseudotyped lentiviral vector particles are then generated with the cloned scFv as described in Example 1. The lentiviral vector particles pseudotyped with the selected scFv-H proteins are then tested for transduction of HT1080 versus HT1080-CD20 cells. Those scFv proteins that mediate efficient transduction of HT1080-CD20 cells but not of HT1080 cells must be directed against the CD20 antigen.

Example 12: Identification of the 7A5 Single Chain Antibody Antigen

In the following series of experiments the ability to identify an antigen for a given single chain antibody with unknown specificity will be demonstrated. The single chain antibody 7A5 has been previously identified by screening a phage display library for binding to the surface of human T-lymphocytes (Engelstaedter et al., 2000; Human Gene Therapy 11, 293). Although it has been established that its antigen is present on the surface of human T-lymphocytes but absent from other human cell types, among these are HEK-293T cells and HT1080 cells, the identity of the antigen is unknown.

To identify the antigen, pseudotyped lentiviral vectors according to this invention are generated displaying the 7A5 on the H protein. The 7A5 cDNA is available in expression plasmids from which it can be easily subcloned into pCG-HmutscFvCD20Δ19 thereby exchanging the CD20 scFv against 7A5. The vectors will then be generated according to Example 5 but a bicistronic transfer vector encoding a neomycin resistance (neo) gene and the GFP gene will be used, so that the resulting vector particles will transfer both marker genes into antigen positive cells. Briefly, HEK-293T cells are co-transfected with the packaging plasmid encoding HIV-1 gag/pol, the transfer plasmid encoding GFP/neo$^r$ and the two plasmids encoding Hmut7A5Δ19 and FcΔ30. After 48 h the cell supernatant, that contains the pseudotyped HIV-1 vectors, is filtered and concentrated. To test selective transduction of the neo$^r$ gene into T-lymphocytes, A301 cells and antigen negative cell lines like HT1080 and HEK-293T will be incubated with the vector particles and transfer of the neo$^r$ and GFP genes will be assayed by adding neomycin into the cell culture medium (0.5-1 mg/ml) or by analyzing the cells for GFP expression under the fluorescent microscope. It is expected that HT1080 and HEK-293T cells will remain negative for expression of both markers, while A301 cells will become positive.

In the next step, a cDNA expression library from human T-lymphocytes packagable in an MLV vector will be used to transduce and express the cDNA library in HT1080 or HEK-293T cells. Methods of preparing cDNA and of constructing cDNA expression libraries are well known in the art, and any such method can be used (see Sambrook et al., 1989). Alternatively, retroviral packagable cDNA libraries from human T-lymphocyte tissue can be purchased from commercial suppliers. The cDNA library transduced cells will then be incubated with the 7A5 pseudotyped lentiviral vector. It is expected that those cells expressing the 7A5 antigen in the transduced cell population will become GFP and neo$^r$ positive. These cells can therefore be selected under neomycin or sorted by fluorescent activated cell sorting. Subsequently the cells are amplified under standard cell culture conditions. Finally, the cDNA expressed in the selected cells can be cloned and sequenced to identify the 7A5 antigen by gene bank search.

Example 13: Production. Isolation and Titration of Lentiviral Vector Particles Pseudotyped with F and H Proteins with Further Truncated Cytoplasmic Tails Pseudotyped lentiviral vector particles were produced by co-transfection of HEK-293T cells with the packaging plasmid pCMVΔR8.9 encoding the HIV-1 gag and pol genes, the transfer plasmid pSEW encoding a gfp reporter gene and the two plasmids encoding the differently truncated H and F protein variants, respectively. In case of the H protein starting from HcΔ20, variants with serially further truncated C-tails were generated by PCR mutagenesis of pCG-H as described in Example 1.

For generation of the pseudotyped vectors, 6.5×10$^6$ HEK-293T cells (in DMEM with 4.5 g/l glucose, 3.7 g/l NaHCO$_3$, 10% FCS, 1% glutamine) were seeded into a T75 flask 24 h before transfection. 1 h before transfection the medium of the cells was exchanged against 5 ml fresh medium. 7 μg of plasmid pCGFcΔ30, 1.0 μg of the plasmid encoding the respective H protein variant (pCGHcΔ21 to pCGHcΔ24, pCGHcΔ26+6A or pCGHcΔ30+10A), 6.72 μg of plasmid pCMVΔR8.9, and 11.27 μg of pSEW were co-transfected by calcium phosphate transfection.

The plasmid DNA was filled up with H$_2$O (Sigma; W-3500) to 450 μl. Then 50 μl 2.5 M CaCl$_2$ (Sigma, C7902) solution were added. While vortexing the DNA-CaCl$_2$ solution, 500 μl 2×HBS Buffer (281 mM NaCl (Sigma, S7653); 100 mM HEPES (Sigma, H3375); 1.5 mM Na$_2$HPO$_4$ (Sigma, S0876)) were added dropwise. The suspended precipitate was then transferred to the HEK-293T cells. 3-4 h later, 5 ml fresh medium were added and 15 h after this the medium was replaced with 12 ml fresh medium.

24 h afterwards, the 12 ml cell supernatant containing the pseudotyped lentiviral vector particles, were filtered (0.45 μm filter) and 300 μl thereof were directly used for the transduction of HT1080 cells. The remaining supernatant was concentrated by centrifugation at 3600 rpm (Heraeus multifuge 3S-R) and 40° C. for at least 16 h. The pellet was then resuspended in 120 μl serum free medium (DMEM with 4.5 g/l glucose, 3.7 g/l NaHCO$_3$).

For titration of the unconcentrated vector particle stocks, 1.0×10$^5$ HT1080 cells (in DMEM with 4.5 g/l glucose, 3.7 g/l NaHCO$_3$, 10% FCS, 1% glutamin) were seeded into a single well of a 24-well plate. On the next day, the vector stocks were serially diluted in 1:10 steps and a total of 250 μl of the dilutions, including 2.0 μg polybrene were then added to every well, incubated for 2.5-3h and replaced by 1 ml of fresh medium. After 48-72 h the titers were calculated by determining the number of green fluorescent cells per well by counting under the fluorescence microscope. For counting a dilution was selected where significantly less than every cell has been transduced. To figure out the number of transducing particles per ml the counted cells per well were multiplied by the dilution factor and the factor 4 (used 250 μl×4=1 ml).

The titers are summarized in Table 6.

TABLE 6

Titers of HIV-1 particles pseudotyped with MeV FcΔ30 and MeV H proteins with further truncated cytoplasmic tails on HT1080 cells

| envelope proteins | HT1080 [t.u./ml][a] |
|---|---|
| FcΔ30 HcΔ21 | 1.5 * 10³ |
| FcΔ30 HcΔ22 | 1.4 * 10² |
| FcΔ30 HcΔ23 | 1.3 * 10² |
| FcΔ30 HcΔ24 | 88 |
| FcΔ30 HcΔ26 + 6A | 0 |
| FcΔ30 HcΔ30 + 10A | 0 |

[a]not concentrated cell supernatants were used

The vector particles produced in the presence of FcΔ30 and a H protein variant with a further truncated cytoplasmic tail show no or only very low titers on the HT1080 cells. Accordingly, further truncation of the cytoplasmic tail of the H protein leads to lower titers of pseudotypes.

This could be due to the fact, that the fusion helper function of the H protein gets lost when the cytoplasmic tail is truncated by more than 14 amino acids (Moll et al. 2002, J Virol 76 (14) p. 7174-7186).

In case of the F protein a stop codon is introduced by point mutagenesis into pCG-F (as described in Example 1) to result in a F protein with just one single amino acid (arginine) left as cytoplasmic tail (FcΔ32) and then this further truncated F protein variant is tested for enhanced pseudotyping.

Example 14: Transduction of Primary Human B Cells by HIV-1 Vector Particles Pseudotyped with HmutscFvCD20Δ18 and FcΔ30

For clinical use it is important, that the vector particles of this invention can transduce not only cell lines but also primary human cells. This example demonstrates that HIV-1 vector particles pseudotyped with HmutscFvCD20Δ18/FcΔ30 can efficiently transduce primary human CD20 positive B cells.

The pseudotyped lentiviral vector particles were generated as described in Example 5. Briefly, HEK-293T cells were co-transfected with 6.72 μg packaging plasmid encoding HIV-1 gag/pol, 11.27 μg transfer plasmid encoding GFP, 2.0 μg plasmid encoding HmutscFvCD20Δ18 and 6.0 μg plasmid encoding FcΔ30. This was carried out by calcium phosphate transfection as described in Example 2. As positive control vector particles pseudotyped with VSV-G were produced. For this purpose 4.55 μg of plasmid encoding the VSV-G envelope protein, 8.45 μg of packaging plasmid and 13.00 μg of transfer plasmid were co-transfected.

After 48h the cell supernatants, containing the pseudotyped HIV-1 vector particles, were filtrated, concentrated (as described in Example 2), and then used for the transduction of primary human CD20 positive B cells.

Primary B cells were isolated out of fresh human PBMCs with the Dynal® B-Cell negative isolation kit (Invitrogen) following the instruction manual. Afterwards the isolated B cells were transferred to a single well of a 24-well plate and incubated for 48 h in RPMI 1640 supplemented with 2 g/l NaHCO₃, 10% FCS, 1% glutamin, 0,5% SP, 25 mM Hepes as well as 300 ng/ml CD40 Ligand, 50 ng/ml IL-2, 10 ng/ml IL-4 and 10 ng/ml IL-10. By incubation with these cytokines the B cells become activated, which makes them susceptible for transduction by lentiviral vector particles.

For the transduction of the primary human B cells an MOI of 2 was used, for VSV-G pseudotyped vector particles in addition an MOI of 150. For pre-coating, half of the concentrated HmutscFvCD20Δ18/FcΔ30 or VSV-G pseudotyped HIV-1 vector particles was diluted in 120 μl medium (medium+ cytokines s. above) and transferred to a single well of a fibronectin coated 48-well plate. This plate was then centrifuged at 860 g for 20 min at 4° C.

Meanwhile the other half of the vector particles was diluted in 180 μl medium (supplemented with 1.2 μg protamine sulphate) containing 5*10⁴ isolated primary human B cells and was added to the well with the respective pre-coated vector particles. A centrifugation step at 430 g for 90 min at 32° C. followed. After further 2 h incubation at 37° C. in the incubator, 700 μl medium+ cytokines (s. above) per well were added. To verify that the isolation had worked well and the transduced cells were really CD20 positive B cells, 72 h after transduction the cells were stained against CD20 (mouse anti-human CD20/PE-Cy5; BD Pharmingen™, Heidelbeg, Germany) and CD19 (mouse anti-human CD19/PE; DakoCytomation, Glostrup, Denmark), which are both B cell markers. For this purpose the cells were centrifuged for 2 min at 3.000 rpm (Biofuge fresco Heraeus instruments) at 4° C. The pellets were then resuspended in 1 ml FACS washing buffer (PBS, 1% FCS, 0.1% NaN₃) and centrifuged as above. Next, the pellets were incubated for 1 h at 4° C. in the dark in an appropriate dilution of anti-CD20 and anti-CD19 antibody directly coupled to an appropriate fluorophore. Afterwards the cells were centrifuged as above, washed twice with FACS washing buffer and resuspended in 200 μl PBS/1% paraformaldehyde. Afterwards the fraction of CD20/CD19/GFP triple positive cells was determined by FACS (Dako Galaxy flow cytometry system; s. FIG. 20A-20C).

The isolation of the B cells out of fresh human PBMCs with the Dynal® B Cell negative isolation kit (Invitrogen) had worked well, as nearly all cells were CD20/CD19 double positive and therefore B cells (s. FIG. 20A-20C). With the VSV-G pseudotyped HIV-1 vector particles about 20% of these CD20/CD19 positive B cells became GFP-positive when an MOI of 2 was used (s. FIG. 20A). Remarkably, the HmutscFvCD20Δ18/FcΔ30 pseudotyped HIV-1 vector particles transduced the CD20/CD19 double positive B cells with an efficiency of about 70% (s. FIG. 20B). Even when an MOI of 150 was used, FIG. 20C only about 40% GFP positive cells were obtained with the VSV-G pseudotyped HIV-1 vector particles (s. FIG. 20C), demonstrating that the HmutscFvCD20Δ18/FcΔ30 pseudotyped HIV-1 vector particles described in this invention can transduce primary human B cells even with a higher efficiency than VSV-G pseudotyped vectors. This suggests the application of these vectors for example for the treatment of Burkitt-Lymphoma or other diseases, where a high transduction efficiency of CD20 positive B cells is important.

Example 15: Selective Transduction of B Cells in Primary Human Lymphocyte by HmutscFvCD20Δ18/FcΔ30 Pseudotyped HIV-1 Vector Particles This example illustrates that the invented vector particles are able to mediate a selective gene transfer into a subpopulation of primary human lymphocytes. The HmutscFvCD20Δ18/FcΔ30 pseudotyped HIV-1 vector particles were used for the transduction of a mixture of primary human CD20 positive B cells and primary human CD3 positive T cells.

The pseudotyped lentiviral vector particles were generated as described in Example 5. Briefly, HEK-293T cells were co-transfected with 6.72 µg packaging plasmid encoding HIV-1 gag/pol, 11.27 µg transfer plasmid encoding GFP, 2.0 µg plasmid encoding HmutscFvCD20Δ18 and 6.0 µg plasmid encoding FcΔ30. This was carried out by calcium phosphate transfection as described in Example 2. As positive control vector particles pseudotyped with VSV-G were produced. For this purpose 4.55 µg of plasmid encoding the VSV-G envelope protein, 8.45 µg of packaging plasmid and 13.00 µg of transfer plasmid were co-transfected.

After 48h the cell supernatants, containing the pseudotyped HIV-1 vector particles, were filtrated, concentrated (as described in Example 2), and then used for transduction.

A mixture of primary human CD20+/CD19+B and CD3+ T cells was isolated from a human blood donation. Then, the cells were incubated for 48 h in RPMI 1640 with 2 g/l NaHCO$_3$, 10% FCS, 1% glutamine, 0.5% SP, 25 mM Hepes as well as 300 ng/ml CD40 Ligand, 50 ng/ml IL-2, 10 ng/ml IL-4 and 10 ng/ml IL-10. By incubation with these cytokines the primary cells become activated, which makes them susceptible for transduction by lentiviral vector particles.

For the transduction of the primary human cell mixture an MOI of 2 was used. For pre-coating, half of the concentrated HmutscFvCD20Δ18/FcΔ30 or VSV-G pseudotyped HIV-1 vector particles was diluted in 120 µl medium (medium+ cytokines s. above) and transferred to a single well of a fibronectin coated 48-well plate. This plate was then centrifuged at 860 g for 20 min at 4° C. Meanwhile the other half of the vector particles was diluted in 180 µl medium (supplemented with 1.2 µg protamine sulphate) containing 4*10$^4$ primary human cells and added to the well with the respective pre-coated vector particles. A centrifugation step at 860 g for 1 h at 32° C. followed. After further 2 h incubation at 37° C. in the incubator, 700 µl medium including the cytokines specified above were added per well. To label the B cells, the cells were stained against CD20 (mouse anti-human CD20/PE-Cy5; BD Pharmingen™, Heidelbeg, Germany) and CD19 (mouse anti-human CD19/PE; DakoCytomation, Glostrup, Denmark) 48 h after transduction. For this purpose the cells were centrifuged for 2 min at 3.000 rpm (Biofuge fresco Heraeus instruments) at 4° C. The pellets were then resuspended in 1 ml FACS washing buffer (PBS, 1% FCS, 0.1% NaN$_3$) and centrifuged as above. Next, the pellets were incubated for 1 h at 4° C. in the dark in an appropriate dilution of anti-CD20 and anti-CD19 antibody directly coupled to an appropriate fluorophore. Afterwards the cells were centrifuged as above, washed twice with FACS washing buffer and resuspended in 200 µl PBS/1% paraformaldehyde. Afterwards the GFP positive cells were measured by FACS (Dako Galaxy flow cytometry system; s. FIG. 21).

Figure 21A:
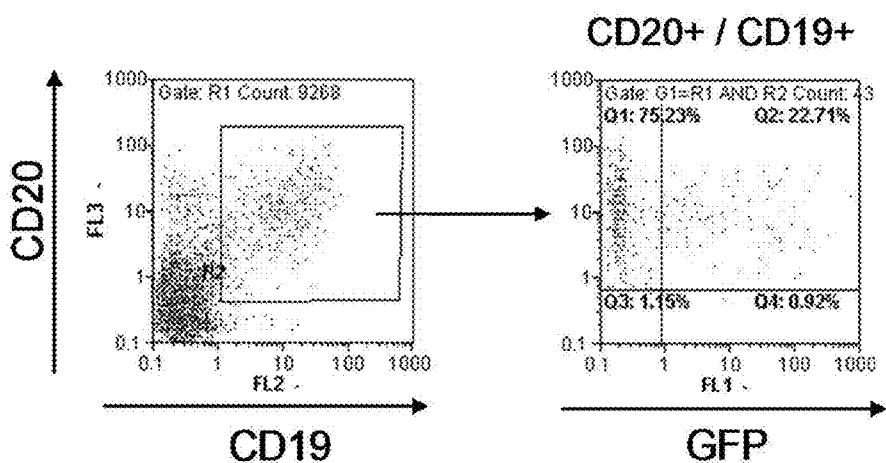
Figure 21B:
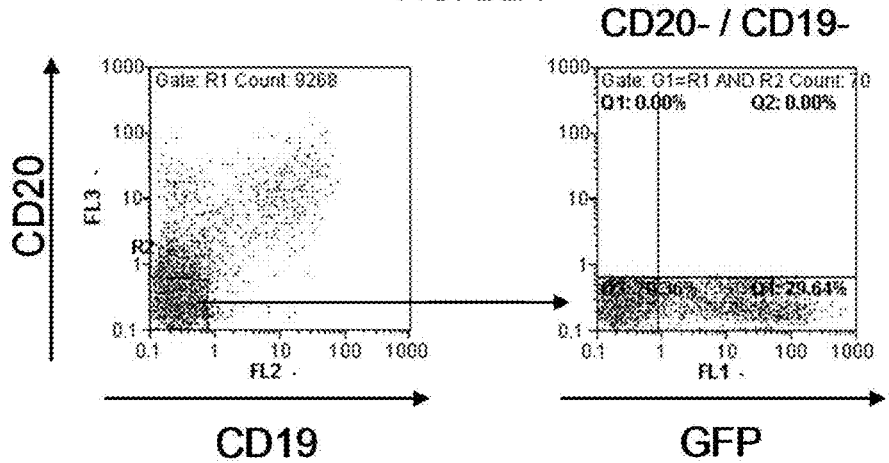
Figure 21C:
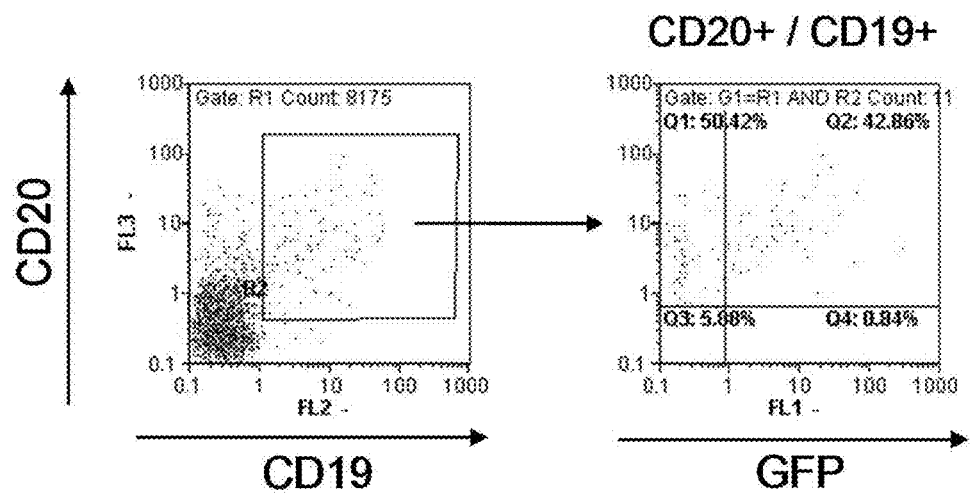
Figure 21D:
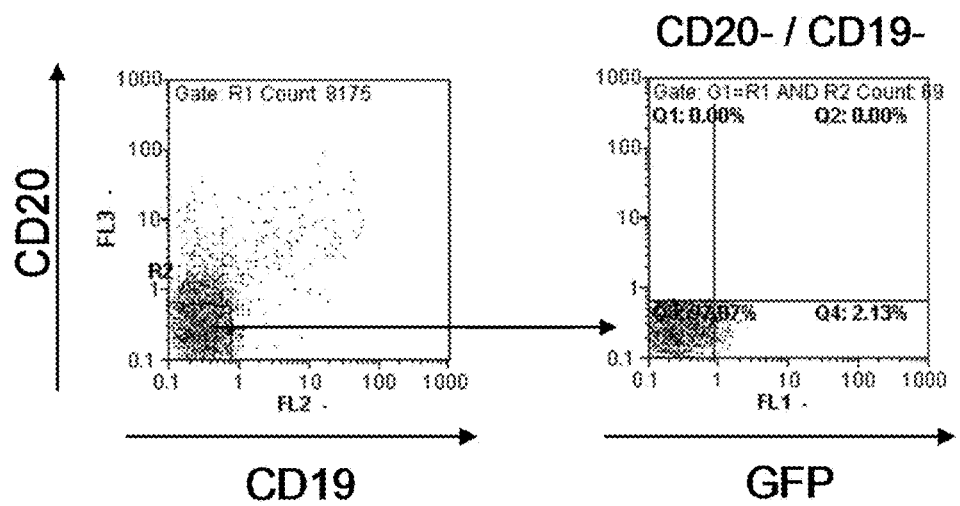

The VSV-G pseudotyped HIV-1 vector particles transduced both, FIGS. 21A, 21B the CD20+/CD19+B cells with an efficiency of about 20% and FIG. 21B the CD20−/CD19− cell fraction mainly consisting of T cells, with an efficiency of about 30% (s. FIGS. 21A-21D). Thus, the VSV-G pseudotyped vector particles did not discriminate between the two cell fractions. In contrast, the HmutscFvCD20Δ18/ FcΔ30 pseudotyped HIV-1 vector particles transduced the CD20 positive B cells with an efficiency of about 40%, FIG. 21C while the CD20−/CD19− cell fraction remained untransduced (s. FIGS. 21B, 21D). This demonstrates the effective targeting of primary human cells with the invented vector system.

Example 16: Production of Pseudotyped SIVmac Vector Particles

This example demonstrates that the same variants of the MeV F and H proteins used for pseudotyping of HIV-1 vector particles can also be used for pseudotyping of other lentiviral vectors.

Pseudotyped SIVmac vector particles were produced by co-transfection of HEK-293T cells with a packaging plasmid, a transfer vector and the two plasmids encoding the H and F protein variants, respectively. The packaging plasmid SIV10+ encoding the SIVmac gag and pol genes is depicted in FIG. 22 (Negre et al. 2000, Gene Ther 7 p. 1613-1623), as an example the transfer plasmid GAE-sffv-gfp-wpre (encoding GFP) is depicted in FIG. 23 (Negre et al. 2000, Gene Ther 7 p. 1613-1623), however, also other transfer plasmids may be utilized.

Pseudotyped SIVmac vector particles were basically generated as described in Example 2. Briefly, HEK-293T cells were co-transfected with 6.72 μg packaging plasmid encoding SIVmac gag/pol, 11.27 μg transfer plasmid encoding GFP, 1 μg of the plasmid encoding the modified MeV H protein and 7 μg of the plasmid encoding the modified MeV F protein. This was carried out by calcium phosphate transfection as described in Example 2. About 48 h after the transfection the cell supernatants, that contain the HcΔ18/FcΔ30 protein and HcΔ19/FcΔ30 protein pseudotyped SIVmac vector particles, respectively, were filtrated, concentrated (as described in Example 2) and used for the transduction of HT1080 cells.

For titration of the concentrated vector particle stocks, $1.0\times10^5$ HT1080 cells (in DMEM with 4.5 g/l glucose, 3.7 g/l $NaHCO_3$, 10% FCS, 1% glutamin) were seeded into a single well of a 24-well plate. On the next day, the vector stocks were serially diluted in 1:10 steps and a total of 250 μl of the dilutions, including 2.0 μg polybrene was then added to every well, incubated for 2.5-3h and replaced by 1 ml of fresh medium. After 48-72 h the titers were calculated by determining the number of green fluorescent cells per well by counting under the fluorescence microscope. For counting a dilution was selected where significantly less than every cell has been transduced. To figure out the number of transducing vector particles per ml the counted cells per well were multiplied by the dilution factor and the factor 4 (used 250 μl×4=1 ml).

Photos of the transduced HT1080 cells are shown in FIG. 24. The HcΔ18/FcΔ30 pseudotyped particles had a titer of $1.7*10^6$ t.u./ml and the HcΔ19/FcΔ30 pseudotyped particles a titer of $3.3*10^5$ t.u./ml on HT1080 cells.

The results of this experiment demonstrate that SIVmac particles can be efficiently pseudotyped with the modified MeV glycoproteins.

REFERENCES CITED

Altschul, S. F., Gish, W., Miller, W., Myers, E. W. & Lipman, D. J., J. Mol. Biol. 215:403-410 (1990).
Cattaneo and Rose, 1993; J Virol 67, 1493-1502.
Cathomen T., et al., Virology 214:628-632 (1995).
Engelstaedter et al., 2000; Human Gene Therapy 11, 293.
Griffiths et al., 1994; EMBO J., 13, 3245-3260.
Jespersen et al. 2000, Eur J Biochem. 267 (5) p. 1382-9

Junker et al. 2003, Gene Therapy 10 p. 1189-1197
Laemmli U K, "Cleavage of structural proteins during the assembly of the head of bacteriophage T4," Nature 227:680-685 (1970).
Masse et al. (2002) J Virol 76 (24) p. 13034-13038.
Masse et al. (2004) J Virol 78 (17) p. 9051-9063.
Moll et al. 2002, J Virol 76 (14) p. 7174-7186
Nakamura et al. (2004) Nat. Biotech. 22 (3) p. 331-336.
Nakamura et al. (2005) Nat. Biotech. 23 (2) p. 209-214.
Negre et al. 2000, Gene Ther 7 p. 1613-1623
Patterson et al. (1999) Virology 256 p. 142-151.
Pearson W R and Lipman D J, "Improved tools for biological sequence comparison", Proc Natl Acad Sci USA 85:2444-2448 (1988).
Plemper R K, Hammond A L, Cattaneo R., "Measles virus envelope glycoproteins hetero-oligomerize in the endoplasmic reticulum", J Biol Chem. 2001, 23; 276(47):44239-46.
Saiki R K, Gelfand D H, Stoffel S, Scharf S J, Higuchi R, Horn G T, Mullis K B, and Erlich H A, Science 239:487 (1988).
Sambrook J, Fritsch E F, and Maniatis T, Molecular Cloning. A Laboratory Manual, 2d ed., Cold Spring Harbor Laboratory, Cold Spring Harbor (1989).
Takeda et al. 2000, J Virol 74 (14) p. 6643-6647
Toennes et al., J. Neurochem. 73, 2195 (1999).
Vongpunsawad et al. (2004) J Virol 78 (1) p. 302-313.
Xu K, Ma H, McCown T J, Verma I M, Kafri T., Mol. Ther. 3:97-104 (2001).
Yanagi et al. (2006) Jpn J Infect Dis. 59 (1) p. 1-5
Zoller M J, and Smith M, Nucleic Acids Res 10:6487-6500 (1982).
Zoller M J, Methods Enzymol 100:468-500 (1983).
Zoller M J, DNA 3(6):479-488 (1984). DMS AOM 11966284v1

---

The invention claimed is:

1. A pseudotyped lentiviral vector particle comprising a fusion (F) protein and a hemagglutinin (H) protein of a *morbillivirus*, wherein the cytoplasmic portions of said F and H proteins are truncated by deletion of amino acid residues from said cytoplasmic portions, and wherein the truncated cytoplasmic portion of the F protein comprises at least 1 positively charged amino acid residue and no more than 9 consecutive amino acid residues as counted from the N-terminal end of the cytoplasmic portion of the F protein, the truncated cytoplasmic portion of the H protein is truncated to allow efficient pseudotyping and has fusion support function, wherein the truncated cytoplasmic portion of the H protein comprises at least 13 and no more than 19 consecutive amino acid residues as counted from the C-terminal end of the cytoplasmic portion of the H protein plus an additional methionine at the N-terminus, wherein the amount of truncated F protein is 250-750% higher than the amount of truncated H protein, wherein the *morbillivirus* is the Edmonston strain of measles virus, wherein the truncated H protein is a chimeric protein that does not interact with CD46 or SLAM and further has a single chain antibody or ligand at its ectodomain for selective gene transfer into target cells.

2. The pseudotyped lentiviral vector particle of claim 1, wherein the target cells are hematopoietic stem cells (HSC) or precursor cells expressing CD34 and/or CD133, and
wherein the single chain antibody binds to CD34 or CD133.

3. The pseudotyped lentiviral vector particle of claim 1, wherein said single chain antibody or ligand is directed against or binding a molecule selected from the group consisting of CD4, CD8, CD34, CD20, CD19, CD33, CD133, EGF-R and VEGFR-2, a mucin-1, a dopamine receptor, an acetylcholine receptor, a GABA receptor, VEGFR-2, an HIV gp120 protein, an epidermal growth factor receptor, a vascular endothelial growth factor receptor, a hepatocyte growth factor receptor, an interleukin receptor, a cytokine receptor and an erythropoietin receptor.

4. A pseudotyped lentiviral vector particle comprising a fusion (F) protein and a hemagglutinin (H) protein of a *morbillivirus*,
wherein the cytoplasmic portions of said F and H proteins are truncated by deletion of amino acid residues from said cytoplasmic portions, and
wherein the truncated cytoplasmic portion of the F protein comprises at least 1 positively charged amino acid residue and no more than 9 consecutive amino acid residues as counted from the N-terminal end of the cytoplasmic portion of the F protein, the truncated cytoplasmic portion of the H protein is truncated to allow efficient pseudotyping and has fusion support function,
wherein the truncated cytoplasmic portion of the H protein comprises at least 13 and no more than 19 consecutive amino acid residues as counted from the C-terminal end of the cytoplasmic portion of the H protein plus an additional methionine at the N-terminus,
wherein the amount of truncated F protein is 250-750% higher than the amount of truncated H protein,
wherein the *morbillivirus* is the Edmonston strain of measles virus,
wherein said vector particle is capable to transduce cells expressing at least one of CD46 and SLAM or is capable to selectively transduce cells expressing SLAM,
wherein said pseudotyped lentiviral vector particle selectively transfers a gene coding for a cytotoxic protein or an immune-stimulatory factor or an immune stimulatory protein or a functional copy of a defective or mutated gene in a patient suffering from an inherited disease into a target cell for the preparation of a medicament.

5. The pseudotyped lentiviral vector particle of claim 4, wherein the target cell is a T cell.

6. The pseudotyped lentiviral vector particle of claim 4, wherein the amount of truncated F protein is 700% higher than the amount of truncated H protein.

* * * * *